(12) United States Patent
Shim et al.

(10) Patent No.: US 9,891,590 B2
(45) Date of Patent: Feb. 13, 2018

(54) REVERSE BATTERY PROTECTION DEVICE AND OPERATING METHOD THEREOF

(71) Applicant: LG ELECTRONICS INC., Seoul (KR)

(72) Inventors: Hongjo Shim, Seoul (KR); Gukchan Lim, Seoul (KR); Youngho Sohn, Seoul (KR); Seonghyok Kim, Seoul (KR); Chohee Kwon, Seoul (KR); Hyunwoo Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 14 days.

(21) Appl. No.: 14/872,852

(22) Filed: Oct. 1, 2015

(65) Prior Publication Data
US 2016/0103985 A1 Apr. 14, 2016

(30) Foreign Application Priority Data

Oct. 8, 2014 (KR) ........................ 10-2014-0135746

(51) Int. Cl.
*G06F 3/041* (2006.01)
*G06F 3/0487* (2013.01)
(Continued)

(52) U.S. Cl.
CPC .......... *G04B 47/063* (2013.01); *A61B 5/0015* (2013.01); *A61B 5/02427* (2013.01); *A61B 5/02438* (2013.01); *A61B 5/681* (2013.01); *A61B 5/684* (2013.01); *A61B 5/742* (2013.01); *G04G 21/00* (2013.01); *G06F 1/163* (2013.01); *G06F 3/01* (2013.01); *G06F 3/0346* (2013.01);
(Continued)

(58) Field of Classification Search
CPC ....... A61B 5/021; A61B 5/024; A61B 5/6898; A61B 5/6887; H04N 21/42201; H04N 21/42202; G06F 21/32; G06F 1/163; G06F 1/32; G06F 1/3231; G06F 3/04883; G06F 3/0487; H04W 12/08; H04M 1/72533; H04M 1/72569
See application file for complete search history.

(56) References Cited

U.S. PATENT DOCUMENTS 8,219,840 B1  7/2012  Nanda et al.
8,223,024 B1  7/2012  Petrou
(Continued)

OTHER PUBLICATIONS

European Patent Office Application No. 16182252.3, Search Report dated Oct. 20, 2016, 8 pages.
(Continued)

*Primary Examiner* — Tae Kim
(74) *Attorney, Agent, or Firm* — Lee Hong Degerman Kang & Waimey

(57) ABSTRACT

A wearable device includes: a touch screen; an acceleration sensor configured to generate an acceleration signal; an optical sensor using a light source and configured to generate a touch interrupt signal; and a control unit configured to detect a wearing state of the wearable device, the wearing state of the wearable device including a not-wearing state for the wearable device, a wrist wearing state, and a hand gripping state on the basis of the acceleration signal and the touch interrupt signal, and to execute a function corresponding to the wearing state of the wearable device.

19 Claims, 38 Drawing Sheets

(51) Int. Cl.

| | |
|---|---|
| *G06F 3/0488* | (2013.01) |
| *G06F 3/01* | (2006.01) |
| *H04N 21/414* | (2011.01) |
| *G06F 21/32* | (2013.01) |
| *A61B 5/00* | (2006.01) |
| *A61B 5/024* | (2006.01) |
| *G04B 47/06* | (2006.01) |
| *H04N 21/422* | (2011.01) |
| *G06F 3/0346* | (2013.01) |
| *G06F 1/16* | (2006.01) |
| *G06F 3/042* | (2006.01) |
| *G04G 21/00* | (2010.01) |
| *H05K 5/00* | (2006.01) |
| *G06F 3/0481* | (2013.01) |

(52) U.S. Cl.
CPC ............ *G06F 3/042* (2013.01); *G06F 3/0414* (2013.01); *G06F 21/32* (2013.01); *H04N 21/41407* (2013.01); *H04N 21/42201* (2013.01); *H04N 21/42202* (2013.01); *H05K 5/0017* (2013.01); *A61B 2562/0219* (2013.01); *G06F 3/0416* (2013.01); *G06F 3/04817* (2013.01)

(56) References Cited

U.S. PATENT DOCUMENTS

| | | | |
|---|---|---|---|
| 8,355,698 B2 | 1/2013 | Teng et al. | |
| 8,560,004 B1 | 10/2013 | Tsvetkov et al. | |
| 8,854,925 B1 | 10/2014 | Lee et al. | |
| 9,606,721 B2 | 3/2017 | Park et al. | |
| 2005/0289363 A1 | 12/2005 | Tsirkel et al. | |
| 2007/0085157 A1 | 4/2007 | Fadell et al. | |
| 2010/0001967 A1 | 1/2010 | Yoo | |
| 2010/0306718 A1 | 12/2010 | Shim et al. | |
| 2011/0014956 A1 | 1/2011 | Lee et al. | |
| 2012/0007713 A1* | 1/2012 | Nasiri .................. G06F 1/1694 340/5.81 |
| 2012/0235790 A1 | 9/2012 | Zhao et al. | |
| 2012/0280917 A1 | 11/2012 | Toksvig et al. | |
| 2013/0045037 A1* | 2/2013 | Schaffer .................. G06F 1/163 400/472 |
| 2013/0081133 A1 | 3/2013 | Hetroy | |
| 2013/0222270 A1 | 8/2013 | Winkler et al. | |
| 2014/0125619 A1 | 5/2014 | Panther et al. | |
| 2014/0135612 A1* | 5/2014 | Yuen .................. A61B 5/02405 600/407 |
| 2014/0160078 A1 | 6/2014 | Seo et al. | |
| 2014/0176422 A1 | 6/2014 | Brumback et al. | |
| 2014/0239065 A1 | 8/2014 | Zhou et al. | |
| 2014/0275850 A1 | 9/2014 | Venkatraman et al. | |
| 2014/0275852 A1* | 9/2014 | Hong .................. A61B 5/02427 600/301 |
| 2014/0275854 A1 | 9/2014 | Venkatraman et al. | |
| 2014/0292641 A1 | 10/2014 | Cho et al. | |
| 2014/0371601 A1 | 12/2014 | Fei | |
| 2015/0190094 A1 | 7/2015 | Lee et al. | |
| 2015/0324181 A1 | 11/2015 | Segal | |
| 2016/0004393 A1 | 1/2016 | Faaborg et al. | |
| 2016/0036996 A1* | 2/2016 | Midholt ................ G06F 1/3206 455/567 |
| 2016/0063850 A1* | 3/2016 | Yang ..................... G08B 23/00 340/539.22 |
| 2016/0073954 A1 | 3/2016 | Meitav | |

OTHER PUBLICATIONS

European Patent Office Application Serial No. 15186115.0, Search Report dated Feb. 18, 2016, 8 pages.

U.S. Appl. No. 15/208,491, Office Action dated Dec. 27, 2016, 16 pages.

U.S. Appl. No. 15/208,491, Notice of Allowance dated May 22, 2017, 14 pages.

U.S. Appl. No. 15/167,874, Office Action dated Jul. 11, 2017, 24 pages.

United States Patent and Trademark U.S. Appl. No. 15/670,804, Office Action dated Nov. 17, 2017, 8 pages.

* cited by examiner

FIG.21
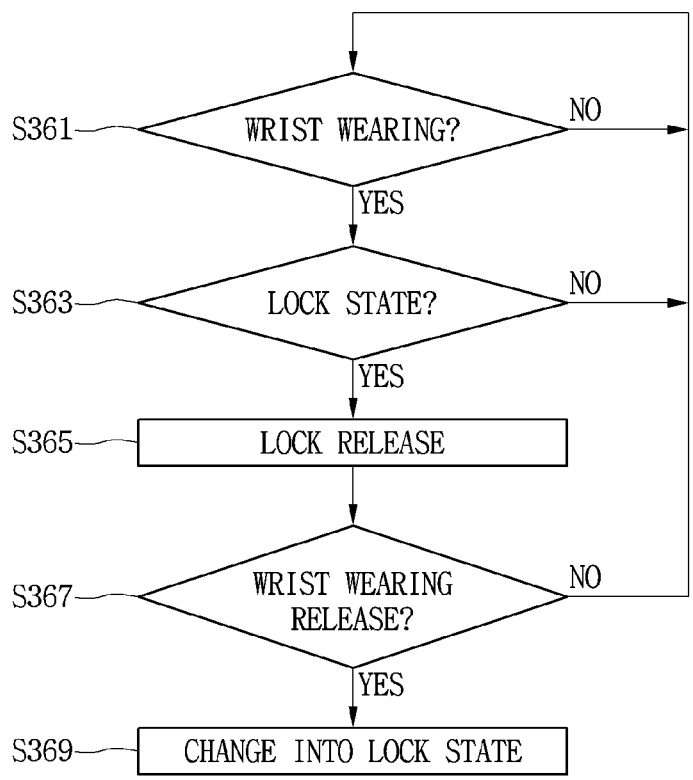
FIG.22A  FIG.22B
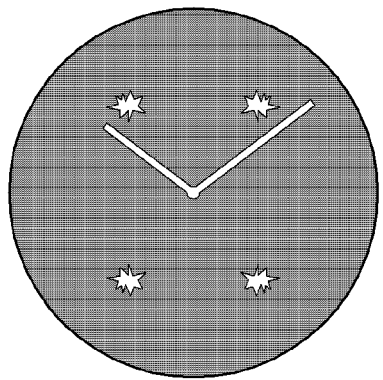 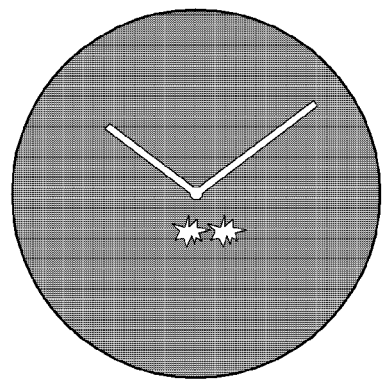

FIG.28
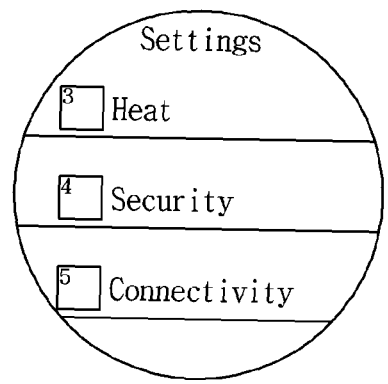
FIG.29A  FIG.29B
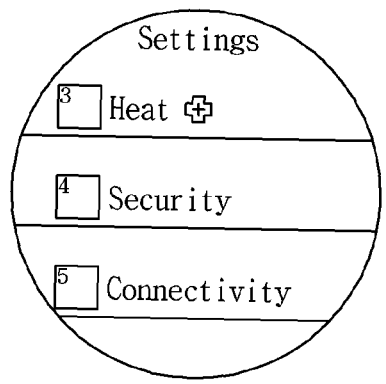 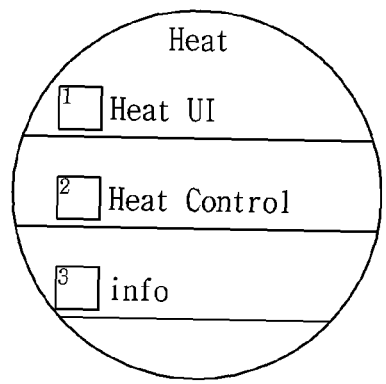

REVERSE BATTERY PROTECTION DEVICE AND OPERATING METHOD THEREOF

CROSS-REFERENCE TO RELATED APPLICATIONS

Pursuant to 35 U.S.C. § 119(a), this application claims the benefit of earlier filing date and right of priority to Korean Patent Application No. 10-2014-0135746, filed on Oct. 8, 2014, the contents of which are hereby incorporated by reference herein in its entirety.

BACKGROUND

The present disclosure relates to a wearable device for further maximizing the user's convenience.

Functions of the mobile terminals become diversified. Mobile terminals may include devices being worn on a user's body, neck, head, or wrist in addition to devices being gripped by a user's hand like mobile phones. Such a device that is wearable by a user is called a wearable device.

As an example of a wearable device, there is a neckband-type device worn on a user's neck, a headset-type device worn on a user's head, or a watch-type device worn on a user's wrist.

For example, a mobile terminal may have functions such as data and voice communication, picture and video capturing through a camera, voice recording, music file playback through a speaker system, and image or video output to a display unit. Mobile terminals may further include an electronic game play function or may perform a multimedia player function. Especially, recent mobile terminals may receive multicast signals for providing visual contents such as broadcast programs and videos.

As functions of a terminal are diversified, such a terminal may be implemented in a form of a multimedia player with multi-functions, for example, photo or video capturing, playback of music or video files, game plays, and broadcast reception.

Moreover, a watch-type device may be usually used as a watch and if necessary, may implement various functions mentioned above, and its weight is light. Furthermore, since a watch-type device has functions that are mostly linked with a mobile phone and there are more rooms to absorb most of the functions of the mobile phone, it is expected for watch-type devices to replace mobile phones and accordingly, research to commercialization for the watch type devices are being actively in progress.

However, various function implementations or user interface implementations for watch type devices are not widely developed so that there are limitations in commercialization.

Especially, a user interface depending on whether a watch-type device is worn is not yet implemented.

SUMMARY

Embodiments provide a wearable device for improving user's convenience with the implementation of a user interface depending on whether a user wears it.

Embodiments also provide a wearable device for improving user's convenience by varying a security degree depending on whether a user wears it.

Embodiments also provide a wearable device for improving product reliability by improving the detection performance of a heartbeat sensor used for detecting whether a user wears it.

In one embodiment, a wearable device includes: a touch screen; an acceleration sensor configured to generate an acceleration signal; an optical sensor using a light source and configured to generate a touch interrupt signal; and a control unit configured to detect a wearing state of the wearable device, the wearing state of the wearable device including a not-wearing state for the wearable device, a wrist wearing state, and a hand gripping state on the basis of the acceleration signal and the touch interrupt signal, and execute a function corresponding to the wearing state of the wearable device. The control unit is configured, when the wearable device is in a not-wearing state, to executes a function in the not-wearing state, when the wearable device is in a wrist wearing state, to executes a function in the wrist wearing state, and when the wearable device is in the hand gripping state, to executes a function in the hand gripping state. The control unit is configured to control the touch screen to display a black screen or an ambient screen as the function in the hand gripping state.

In another embodiment, provided is a control method of a wearable device. The method includes: detecting a wearing state of the wearable device, the wearing state including a not-wearing state for the wearable device, a wrist wearing state, and a hand gripping state on the basis of an acceleration signal and a touch interrupt signal; and executing a function corresponding to the wearing state of the wearable device, wherein the executing of the function includes: when the wearable device is in a not-wearing state, executing a function in the not-wearing state; when the wearable device is in a wrist wearing state, executing a function in the wrist wearing state; and when the wearable device is in the hand gripping state, executing a function in the hand gripping state, wherein a black screen or an ambient screen is displayed on a touch screen as a function in the hand gripping state.

The details of one or more embodiments are set forth in the accompanying drawings and the description below. Other features will be apparent from the description and drawings, and from the claims.

BRIEF DESCRIPTION OF THE DRAWINGS

FIG. 21 is a flowchart illustrating a lock releasing method depending on whether a watch type device is worn according to an embodiment of the present invention.

FIGS. 22(a) and 22(b) are screen views illustrating a method of changing a black screen into a standby screen.

FIG. 28 is a screen view illustrating a setting screen displaying method in a wearing state.

FIGS. 29(a) and 29(b) are screen views illustrating a method of setting heat displayed on a setting screen in a wearing state.

DETAILED DESCRIPTION OF THE EMBODIMENTS

Figure 1:
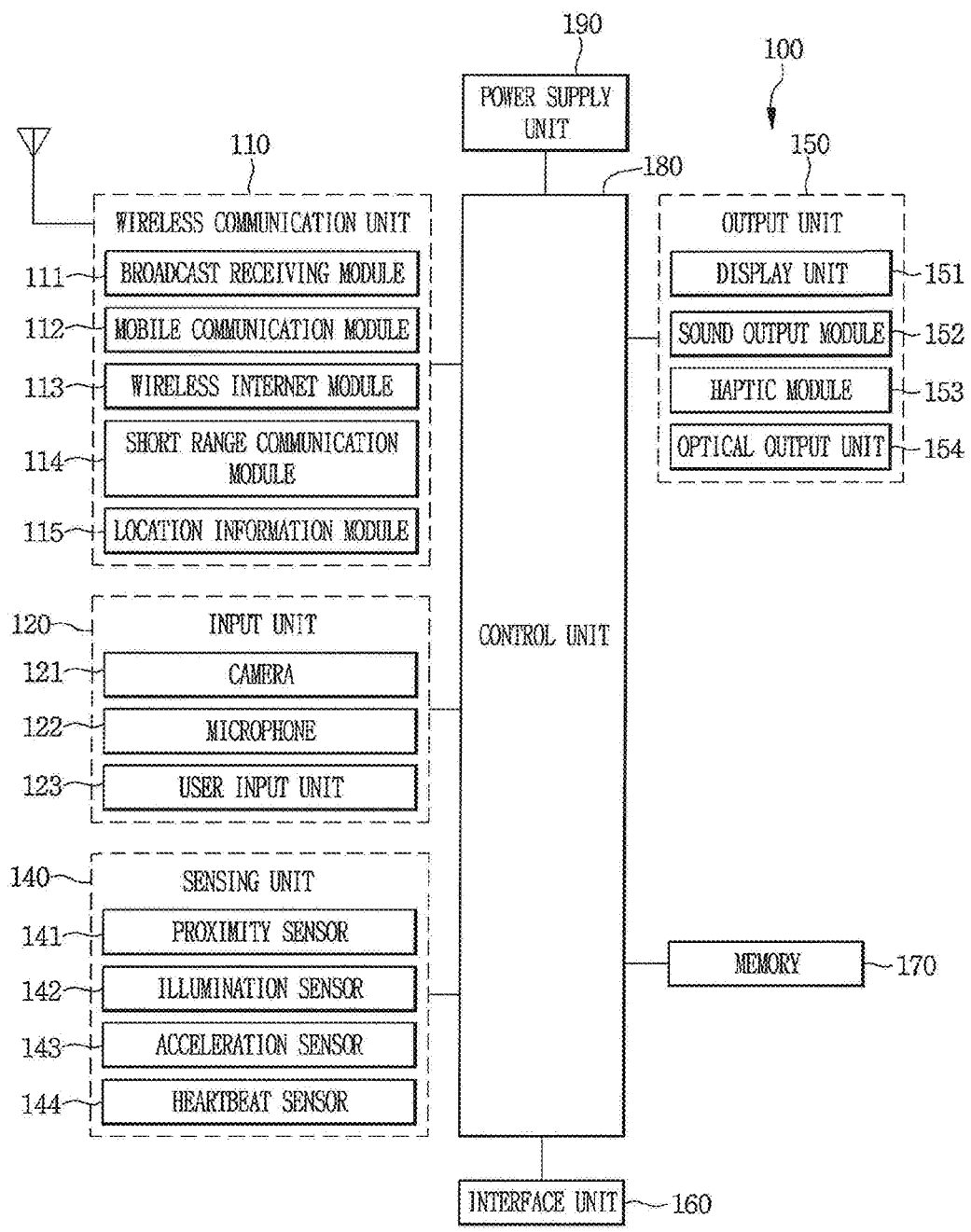
FIG. 1 is a block diagram illustrating a watch-type device.

Hereinafter, embodiments of the present invention are described in more detail with reference to accompanying drawings and regardless of the drawings symbols, same or similar components are assigned with the same reference numerals and thus overlapping descriptions for those are omitted. The suffixes "module" and "unit" for components used in the description below are assigned or mixed in consideration of easiness in writing the specification and, do not have distinctive meanings or roles by themselves. In the following description, detailed descriptions of well-known functions or constructions will be omitted since they would obscure the invention in unnecessary detail. Additionally, the accompanying drawings are used to help easily understanding embodiments disclosed herein but the technical idea of the present invention is not limited thereto. It should be understood that all of variations, equivalents or substitutes contained in the concept and technical scope of the present invention are also included.

It will be understood that the terms "first" and "second" are used herein to describe various components but these components should not be limited by these terms. These terms are used only to distinguish one component from other components.

In this disclosure below, when one part (or element, device, etc.) is referred to as being 'connected' to another part (or element, device, etc.), it should be understood that the former can be 'directly connected' to the latter, or 'electrically connected' to the latter via an intervening part (or element, device, etc.). It will be further understood that when one component is referred to as being 'directly connected' or 'directly linked' to another component, it means that no intervening component is present.

The terms of a singular form may include plural forms unless they have a clearly different meaning in the context.

Additionally, in this specification, the meaning of "include," "comprise," "including," or "comprising," specifies a property, a region, a fixed number, a step, a process, an element and/or a component but does not exclude other properties, regions, fixed numbers, steps, processes, elements and/or components.

FIG. 1 is a block diagram illustrating a watch-type device.

Referring to FIG. 1, the watch type device 100 may include a wireless communication unit 110, an input unit 120, a sensing unit 140, an output unit 150, an interface unit 160, a memory 170, a control unit 180, and a power supply unit 190. In implementing a watch type device, components shown in FIG. 1 are not necessary, so that a watch type device described in this specification may include components less or more than the components listed above.

In more detail, the wireless communication unit 110 in the components may include at least one module allowing wireless communication between the watch type device 100 and a wireless communication system, between the watch type device 100 and another watch type device 100, or between the watch type device 100 and an external server. Additionally, the wireless communication unit 110 may include at least one module connecting the watch type device 100 to at least one network.

The wireless communication unit 110 may include at least one of a broadcast receiving module 111, a mobile communication module 112, a wireless internet module 113, a short-range communication module 114, and a location information module 115.

The input unit 120 may include a camera 121 or an image input unit for image signal input, a microphone 122 or an audio input unit for audio signal input, and a user input unit 123 (for example, a touch key and a mechanical key)) for receiving information from a user. Voice data or image data collected by the input unit 120 are analyzed and processed as a user's control command.

The sensing unit 140 may include at least one sensor for sensing at least one of information in a watch type device, environmental information around a watch type device, and user information. For example, the sensing unit 140 may include at least one of a proximity sensor 141, an illumination sensor 142, an acceleration sensor 143, a heartbeat sensor 144, a touch sensor, a magnetic sensor, a G-sensor, a gyroscope sensor, a motion sensor, an RGB sensor, an infrared (IR) sensor, a finger scan sensor, an ultrasonic sensor, an optical sensor (for example, a camera 121), a microphone 122, a battery gauge, an environmental sensor (for example, a barometer, a hygrometer, a thermometer, a radiation sensor, a thermal sensor, and a gas sensor), and a chemical sensor (for example, an electronic noise, a healthcare sensor, and a biometric sensor). Moreover, a watch type device disclosed in this specification may combines information sensed by at least two or more sensors among such sensors and may then utilize it.

The output unit 150 is used to generate a visual, auditory, or haptic output and may include at least one of a display unit 151, a sound output unit 152, a haptic module 153, and an optical output unit 154. The display unit 151 may be formed with a mutual layer structure with a touch sensor or formed integrally, so that a touch screen may be implemented. Such a touch screen may serve as the user input unit 123 providing an input interface between the watch type device 100 and a user and an output interface between the watch type device 100 and a user at the same time.

The interface unit 160 may serve as a path to various kinds of external devices connected to the watch type device 100. The interface unit 160 may include at least one of a wired/wireless headset port, an external charger port, a wired/wireless data port, a memory card port, a port connecting a device equipped with an identification module, an audio Input/Output (I/O) port, a video I/O port, and an earphone port. In correspondence to that an external device is connected to the interface unit 160, the watch type device 100 may perform an appropriate control relating to the connected external device.

Additionally, the memory 170 may store data supporting various functions of the watch type device 100. The memory 170 may store a plurality of application programs or applications running on the watch type device 100, and data and commands for operations of the watch type device 100. At least part of such an application program may be downloaded from an external server through a wireless communication. Additionally, at least part of such an application program may be included in the watch type device 100 from the time of shipment in order to perform a basic function (for example, an incoming call, a calling function, and a message reception) of the watch type device 100. Moreover, an application program may be stored in the memory 170 and installed on the watch type device 100, so that it may run to perform an operation (or a function) of the watch type device 100 by the control unit 180.

The control unit 180 may control overall operations of the mobile terminal 100 generally besides an operation relating to the application program. The control unit 180 may provide appropriate information or functions to a user or process them by processing signals, data, and information inputted/outputted through the above components or executing application programs stored in the memory 170.

Additionally, in order to execute an application program stored in the memory 170, the control unit 180 may control at least part of the components shown in FIG. 1. Furthermore, in order to execute the application program, the control unit 180 may combine at least two of the components in the watch type device 100 and may then operate it.

The power supply unit 190 may receive external power or internal power under a control of the control unit 180 and may then supply power to each component in the watch type device 100. The power supply unit 190 includes a battery and the battery may be a built-in battery or a replaceable battery.

At least part of the each component may operate cooperatively in order to implement operations, controls, or control methods of a watch type device according to various embodiments of the present invention described below. Additionally, the operations, controls, or control methods of a watch type device may be implemented on the mobile terminal 100 by executing at least one application program stored in the memory 170.

Hereinafter, prior to examining various embodiments implemented through the watch type device 100, the above-listed components are described in more detail with reference to FIG. 1.

First, in describing the wireless communication unit 110, the broadcast receiving module 111 of the wireless communication unit 110 may receive a broadcast signal and/or broadcast related information from an external broadcast management server through a broadcast channel. The broadcast channel may include a satellite channel and a terrestrial channel. At least two broadcast receiving modules for simultaneous broadcast reception for at least two broadcast channels or broadcast channel switching may be provided to the watch type device 100.

The mobile communication module 112 may transmit/receive a wireless signal to/from at least one of a base station, an external terminal, and a server on a mobile communication network established according to the technical standards or communication methods for mobile communication (for example, Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), and Long Term Evolution-Advanced (LTE-A)).

The wireless signal may include various types of data according to a voice call signal, a video call signal, or text/multimedia message transmission.

The wireless internet module 113 refers to a module for wireless internet access and may be built in or external to the watch type device 100. The wireless internet module 113 may be configured to transmit/receive a wireless signal in a communication network according to wireless internet technologies.

The wireless internet technology may include Wireless LAN (WLAN), Wireless-Fidelity (Wi-Fi), Wi-Fi Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), and Long Term Evolution-Advanced (LTE-A) and the wireless internet module 113 transmits/receives data according at least one wireless internet technology including internet technology not listed above.

The short-range communication module 114 may support short-range communication by using at least one of Bluetooth™, Radio Frequency Identification (RFID), Infrared Data Association (IrDA), Ultra Wideband (UWB), ZigBee, Near Field Communication (NFC), Wireless-Fidelity (Wi-Fi), Wi-Fi Direct, and Wireless Universal Serial Bus (USB) technologies. The short-range communication module 114 may support wireless communication between the watch type device 100 and a wireless communication system, between the watch type device 100 and another watch type device 100 or between networks including the watch type device 100 and another watch type device 100 (or an external server) through wireless area networks. The wireless area networks may be wireless personal area networks.

The location information module 115 is a module for obtaining the location (or the current location) of a watch type device and its representative examples include a global positioning system (GPS) module or a Wi-Fi module. For example, a watch type device may obtain its location by using a signal transmitted from a GPS satellite through the GPS module. As another example, a watch type device may obtain its location on the basis of information of a wireless access point (AP) transmitting/receiving a wireless signal to/from the Wi-Fi module, through the Wi-Fi module. If necessary, the position information module 115 may perform a function of another module in the wireless communication unit 110 in order to obtain data on the location of a watch type device substitutionally or additionally. The location information module 115 is a module for obtaining the position (or the current position) of a watch type device and is not limited to a module directly calculating and obtaining the position of a watch type device.

Then, the input unit 120 is used for inputting image information (or signal), audio information (or signal), data, or information inputted from a user and the watch type device 100 may include at least one camera 121 in order for inputting image information. The camera 121 processes image frames such as a still image or a video obtained by an image sensor in a video call mode or a capturing mode. The processed image frame may be displayed on the display unit 151 or stored in the memory 170. Moreover, a plurality of cameras 121 equipped in the watch type device 100 may be arranged in a matrix structure and through the camera 121 having such a matrix structure, a plurality of image information having various angles or focuses may be inputted to the watch type device 100. Additionally, the plurality of cameras 121 may be arranged in a stereo structure to obtain the left and right images for implementing a three-dimensional image.

The microphone 122 processes external sound signals as electrical voice data. The processed voice data may be utilized variously according to a function (or an application program being executed) being performed in the watch type device 100. Moreover, various noise canceling algorithms for removing noise occurring during the reception of external sound signals may be implemented in the microphone 122.

The user input unit 123 is to receive information from a user and when information is inputted through the user input unit 123, the control unit may control an operation of the watch type device 100 to correspond to the inputted information. The user input unit 123 may include a mechanical input means (or a mechanical key, for example, a button, a dome switch, a jog wheel, and a jog switch at the front, back or side of the watch type device 100) and a touch type input means. As one example, a touch type input means may include a virtual key, a soft key, or a visual key, which is displayed on a touch screen through software processing or may include a touch key disposed at a portion other than the touch screen. Moreover, the virtual key or visual key may have various forms and may be disposed on a touch screen and for example, may include graphic, text, icon, video, or a combination thereof.

Moreover, the sensing unit 140 may sense at least one of information in a watch type device, environmental information around a watch type device, and user information and may then generate a sensing signal corresponding thereto. On the basis of such a sensing signal, the control unit 180 may control the drive or control of the watch type device 100 or may perform data processing, functions, or operations relating to an application program installed in the watch type device 100. Representative sensors among various sensors included in the sensing unit 140 will be described in more detail.

First, the proximity sensor 141 refers to a sensor detecting whether there is an object approaching a predetermined detection surface or whether there is an object around by using the strength of an electromagnetic field or infrared, without mechanical contact. The proximity sensor 141 may disposed in an inner area of a watch type device surrounded by the touch screen or around the touch screen.

Examples of the proximity sensor 141 may include a transmission-type photoelectric sensor, a direct reflective-type photoelectric sensor, a minor reflective-type photoelectric sensor, a high-frequency oscillation-type proximity sensor, a capacitive-type proximity sensors, a magnetic-type proximity sensor, and an infrared proximity sensor. If the touch screen is a capacitive type, the proximity sensor 141 may be configured to detect the proximity of an object by changes in an electric field according to the proximity of the object having conductivity. In this case, the touch screen (or a touch sensor) itself may be classified as a proximity sensor.

Moreover, for convenience of description, an action for recognizing the position of an object on the touch screen as the object is close to the touch screen without contacting the touch screen is called "proximity touch" and an action that the object actually contacts the touch screen is called "contact touch". A position that an object is proximity-touched on the touch screen is a position that the object vertically corresponds to the touch screen when the object is proximity-touched. The proximity sensor 141 may detect a proximity touch and a proximity touch pattern (for example, a proximity touch distance, a proximity touch direction, a proximity touch speed, a proximity touch time, a proximity touch position, and a proximity touch movement state). Moreover, the control unit 180 processes data (for information) corresponding to a proximity touch operation and a proximity touch pattern, detected through the proximity sensor 141, and furthermore, may output visual information corresponding to the processed data on the touch screen. Furthermore, depending on whether a touch for the same point on the touch screen is a proximity touch or a contact touch, the control unit 180 may control the watch type device 100 to process different operations or data (or information).

The touch sensor detects a touch (or a touch input) applied to the touch screen (or the display unit 151) by using at least one of various touch methods, for example, a resistive film method, a capacitive method, an infrared method, an ultrasonic method, and a magnetic field method.

For example, the touch sensor may be configured to convert a pressure applied to a specific portion of the touch screen or changes in capacitance occurring at a specific portion into electrical input signals. The touch sensor may be configured to detect a position and area that a touch target applying a touch on the touch screen touches the touch sensor, a pressured when touched, and a capacitance when touched. Here, the touch target, as an object applying a touch on the touch sensor, may be a finger, a touch pen, a stylus pen, or a pointer, for example.

In such a manner, when there is a touch input on the touch sensor, signal(s) corresponding thereto are sent to a touch controller. The touch controller processes the signal(s) and then transmits corresponding data to the control unit 180. Therefore, the control unit 180 may recognize which area of the display unit 151 is touched. Herein, the touch controller may be an additional component separated from the control unit 180 or may be the control unit 180 itself.

The heartbeat sensor 144 detects a light emitted from a light emitting unit (for example, a light emitting diode) from a light receiving unit (for example, a photo diode) and measures a heartbeat by using the detected result.

A structure of the heartbeat sensor 144 and a user interface implementation using the heartbeat sensor 144 are described in more detail later.

Moreover, the control unit 180 may perform different controls or the same control according to types of a touch target touching the touch screen (or a touch key equipped separated from the touch screen). Whether to perform different controls or the same control according to types of a touch target may be determined according to a current operation state of the watch type device 100 or an application program in execution.

Moreover, the above-mentioned touch sensor and proximity sensor are provided separately or combined and may thus sense various types of touches, for example, short (or tap) touch, long touch, multi touch, drag touch, flick touch, pinch-in touch, pinch-out touch, swipe touch, and hovering touch for the touch screen.

The display unit 151 may display (output) information processed in the watch type device 100. For example, the display unit 151 may display execution screen information of an application program running on the watch type device 100 or user interface (UI) and graphic user interface (GUI) information according to such execution screen information.

Additionally, the display unit 151 may be configured as a three-dimensional display unit displaying a three-dimensional image.

The sound output unit 152 may output audio data received from the wireless communication unit 110 or stored in the memory 170 in a call signal reception or call mode, a recording mode, a voice recognition mode, or a broadcast reception mode. The sound output unit 152 may output a sound signal relating to a function (for example, a call signal reception sound and a message reception sound) performed by the mobile terminal 100. The sound output unit 152 may include a receiver, a speaker, and a buzzer.

The haptic module 153 generates various haptic effects that a user can feel. A representative example of a haptic effect that the haptic module 153 generates is vibration. The intensity and pattern of vibration generated by the haptic module 153 may be controlled by a user's selection or a setting of a control unit. For example, the haptic module 153 may synthesize and output different vibrations or output different vibrations sequentially.

The optical output unit 154 outputs a signal for notifying event occurrence by using light of a light source of the watch type device 100. An example of an event occurring in the watch type device 100 includes message reception, call signal reception, missed calls, alarm, schedule notification, e-mail reception, and information reception through an application.

The interface unit 160 may serve as a path to all external devices connected to the watch type device 100. The interface unit 160 may receive data from an external device, receive power and deliver it to each component in the watch type device 100, or transmit data in the watch type device 100 to an external device. For example, the interface unit 160 may include a wired/wireless headset port, an external charger port, a wired/wireless data port, a memory card port, a port connecting a device equipped with an identification module, an audio I/O port, a video I/O port, and an earphone port.

Moreover, the identification module, as a chip storing various information for authenticating usage authority of the watch type device 100, may include a user identity module (UIM), a subscriber identity module (SIM), and a universal subscriber identity module (USIM). A device equipped with an identification module (hereinafter referred to as an identification device) may be manufactured in a smart card form. Accordingly, the identification device may be connected to the terminal 100 through the interface unit 160.

Moreover, as mentioned above, the control unit 180 may control operations relating to an application program and overall operations of the watch type device 100 in general. For example, if a state of a watch type device satisfies set conditions, the control unit 180 may execute or release a lock state limiting an output of a control command of a user for applications.

Additionally, the control unit 180 may perform a control or processing relating to a voice call, data communication, and a video call may perform pattern recognition processing for recognizing handwriting input or drawing input on the touch screen as a text and an image, respectively. Furthermore, the control unit 180 may use at least one or a combination of the above components to perform a control in order to implement various embodiments described below on the watch type device 100.

The power supply unit 190 may receive external power or internal power under a control of the control unit 180 and may then supply power necessary for an operation of each component. The power supply unit 190 includes a battery. The battery is a rechargeable built-in battery and may be detachably coupled to a terminal body in order for charging.

Additionally, the power supply unit 190 may include a connection port and the connection port may be configured as one example of the interface unit 160 to which an external charger supplying power for charging of the battery is electrically connected.

As another example, the power supply unit 190 may be configured to charge a battery through a wireless method without using the connection port. In this case, the power supply unit 190 may receive power from an external wireless power transmission device through at least one of an inductive coupling method based on a magnetic induction phenomenon, and a magnetic resonance coupling method based on an electromagnetic resonance phenomenon.

Figure 2A:
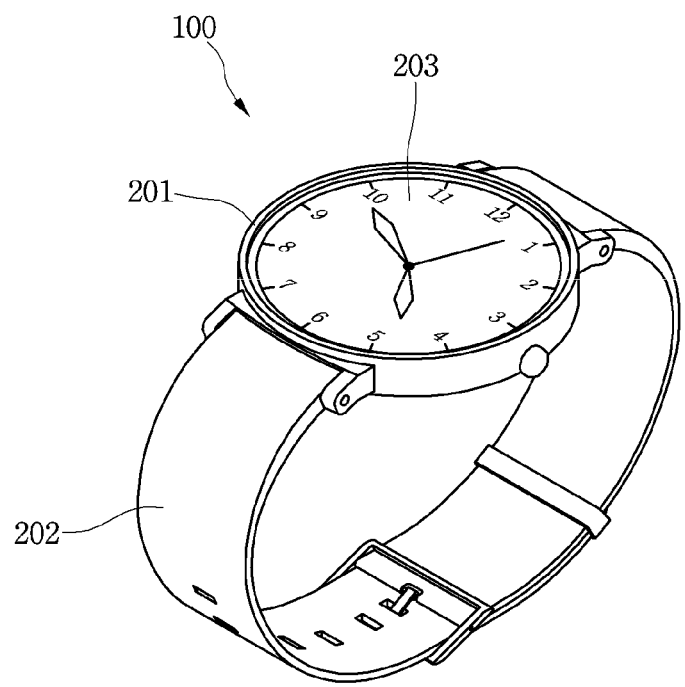
FIG. 2(a) and FIG. 2(b) are conceptual diagrams when a watch type device is seen in different directions according to an embodiment of the present invention.
Figure 2B:
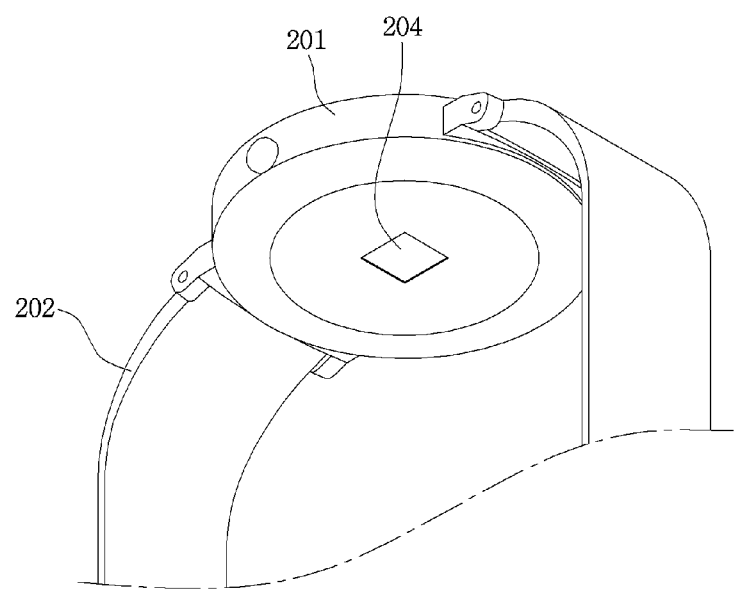

FIG. 2A and FIG. 2B are conceptual diagrams when a watch type device is seen in different directions according to an embodiment of the present invention.

Referring to FIG. 2, the watch type terminal 100 includes a main body 201 with a display unit 203 and a strap 202 connected to the main body 201 to be worn on a wrist.

The main body 201 includes a case for forming the appearance.

The main body 201 is separated into a first case and a second case for preparing an inner space to receive various electronic components and they may be coupled to each other.

As another example, the main body 201 may have an integral form without being separated into first and second cases.

The watch type device 100 may be configured to allow wireless communication and an antenna may be installed at the main body 201 in order for the wireless communication. Moreover, the antenna may expand its performance by using a case. For example, a case including a conductive material may be configured to be electrically connected to an antenna in order to expand a ground area or a radiation area.

The display unit 203 may be disposed at the front of the main body 201 to output information. A touch sensor may be provided at the display unit 203 to be implemented as a touch screen.

The display unit 203 may be the display unit 151 shown in FIG. 1 but is not limited thereto.

The main body 201 may include a sound output unit 152, a camera 121, and a microphone 122. When the display unit 203 is implemented as a touch screen, it may function as a user input unit and accordingly, there is no additional key required at the main body 201.

The strap 202 is worn on a wrist to wrap it and may be formed of a flexible material in order for easy wearing. As such an example, the strap 202 may be formed of leather, rubber, silicon, and synthetic resin. Additionally, the strap 202 may be configured to be detachable from the main body 201, so that it may be replaced with various forms of straps according to user preferences.

Moreover, the strap 202 may be used to expand the performance of an antenna. For example, a ground expansion unit (not shown) electrically connected to an antenna to expand a ground area may be built in a strap.

The strap 202 may include a fastener. The fastener may be implemented by a buckle, a snap-fit available hook structure, or Velcro (a brand name) and may include a stretchable interval or material. This drawing illustrates an example that the fastener is implemented in a buckle form.

As another example, the strap 202 may have an integrated form formed of a flexible material without a fastener so that it may be worn on a wrist through a user's hand.

Moreover, a heartbeat sensor 204 may be disposed at the rear of the main body 201.

Figure 3:
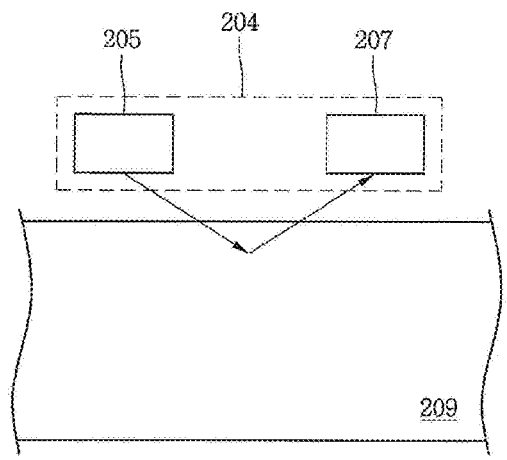
FIG. 3 is a view illustrating the principle of a heartbeat sensor.

The heartbeat sensor 204, as shown in FIG. 3, may include a light emitting unit 205 for emitting light and a light receiving unit 207 for receiving light.

The light emitting unit 205, for example, may include at least one green light emitting device but the present invention is not limited thereto. A light emitting device, for example, may include a semiconductor light emitting device but the present invention is not limited thereto.

Light is emitted on/off periodically from the light emitting unit 205 but the present invention is not limited thereto. For example, an on time for which light is outputted may be about 40 μs.

Figure 4:
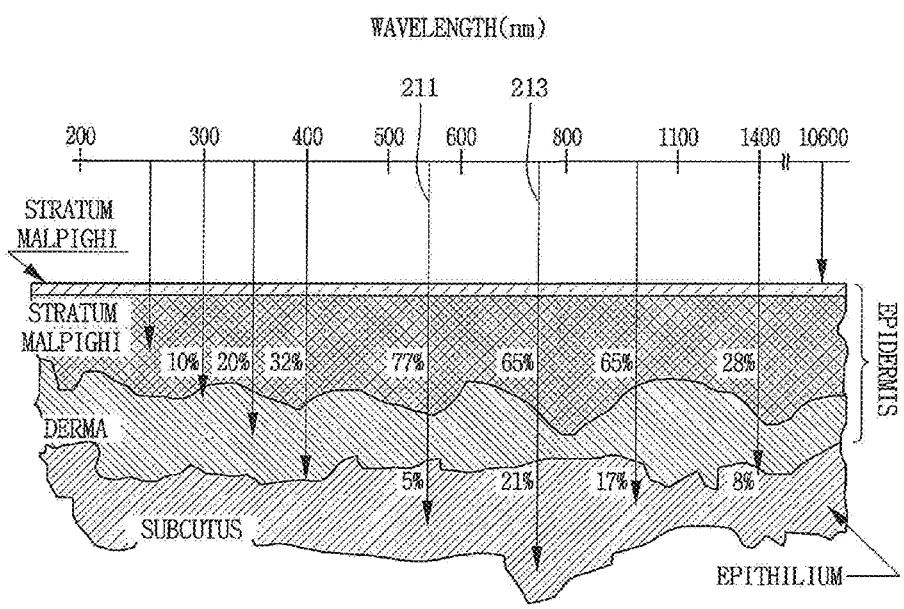
FIG. 4 is a view illustrating a skin penetration rate according to wavelength.

As shown in FIG. 4, except for the light 213 of a red peak wavelength, the light 211 of a green peak wavelength has an excellent skin penetration rate in comparison to the light of another peak wavelength. Herein, a red peak wavelength, for example, is about 656 nm and a green peak wavelength, for example, may be about 555 nm but the present invention is not limited thereto. Accordingly, a green light emitting device for emitting the light of a green peak wavelength may be used as the light emitting unit 205 of the heartbeat sensor 204 shown in FIG. 3. As a skin penetration rate is excellent, the accuracy of heartbeat measurement becomes higher. However, the blood vessels used for measuring a heartbeat are located deep inside the skin. Accordingly, in order to accurately measure a heartbeat from blood vessels located deep inside a skin, the light 211 of a green peak wavelength having an excellent skin penetration rate may be used.

As another example, the present invention is not limited thereto, and a red light emitting device for emitting the light of a red peak wavelength having a more excellent skin penetration rate than the light of a green peak wavelength may be used as the light emitting unit 205.

As another example, the light emitting unit 205 may include both a red light emitting device and a green light emitting device. In such a case, a red light emitting device or a green light emitting device may be selectively used according to the thickness of a skin. Whereas blood vessels are located relatively deep inside a skin in a finger having a thick skin, blood vessels are located relatively near a wrist having a thin skin. Accordingly, when the heartbeat sensor 204 contacts a finger having a relatively thick skin, that is, when the watch type device 100 is gripped by a user's hand, a red light emitting device may operate and the light of a red peak wavelength emitted from a red light emitting device may be used for detecting a touch interrupt signal. When the heartbeat sensor 204 contacts a wrist 209 having a relatively thin skin, that is, when the watch type device 100 is worn on a user's wrist 209, a green light emitting device may operate and the light of a green peak wavelength emitted from a green light emitting device may be used for detecting a touch interrupt signal.

Referring to FIG. 3 again, the light receiving unit 207 may include a plurality of photo diodes but the present invention is not limited thereto. A photo diode may covert light into current and output it.

Accordingly, when the light, which penetrates the skin of the user's wrist 209 and is reflected after emitting from a red light emitting device, is incident to a photo diode, the photo diode may generate and provide a current corresponding to the amount of the incident light.

As mentioned above, the light of a green peak wavelength may be outputted periodically for an on time. Such an outputted light may be reflected on the inside of a skin of the user's wrist 209 and may be incident to a photo diode. A photo diode generates a current corresponding to the amount of a light outputted at each on time and reflected by the user's wrist 209.

A plurality of blood vessels exist in the user's wrist 209. Blood vessels are a passage through which blood flows and the blood flows into all the blood vessels of a body by the pumping of a heart. Since blood flows in blood vessels by the pumping of a heart, the blood vessels are bouncing up and down with a waveform such as a wave.

In such a way, since blood vessels in the user's wrist 209 are bouncing up and down like a wave, the amount of a light reflected by the user's wrist 209 for each on time may vary. By the amount of a light that is changed in this way, a current generated from a photo diode may also vary.

Accordingly, a heartbeat may be measured through a current waveform generated from a photo diode.

In a typical heartbeat sensor, errors may occur during heartbeat measurement due to crosstalk phenomenon.

Figure 5:
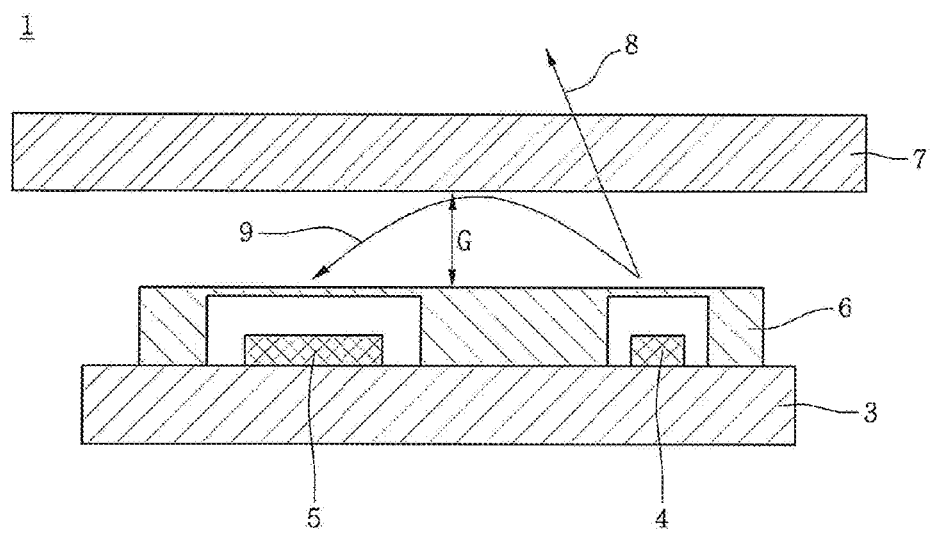
FIG. 5 is a sectional view illustrating a structure of a typical heartbeat sensor.

FIG. 5 is a sectional view illustrating a structure of a typical heartbeat sensor.

Referring to FIG. 5, a typical heartbeat sensor 1 may have a gap G between a cover 6 protecting a light emitting device 4 and a photo diode 5 and a window 7. That is, the window 7 is spatially spaced from the cover 6.

The gap may be 0.1 mm to 1 mm typically.

In such a case, a part of light generated from a light emitting device penetrates the window 7 and progresses toward a user's wrist but another part of light is reflected by the window 7 and incident to a photo diode.

The light progressing toward the user's wrist is reflected by blood vessels in the user's wrist and is incident to the photo diode 5 through the window 7 again.

The photo diode 5 generates a current on the basis of a light (for example, a second light 9) reflected by the window 7 and incident without passing through the user's wrist in addition to a light (for example, a first light 8) passing through the user's wrist. In such a case, since the second light is a light not passing through the user's wrist and is a parameter irrelevant to a heartbeat, the second light is reflected for the current generation, an accurate heartbeat measurement is impossible due to the generated current.

In such a case, in the typical heartbeat sensor 1, by the gap G between the cover 6 and the window 7, a light generated from the light emitting device 4 does not pass through the user's wrist and is directly incident to the photo diode 5, so that crosstalk phenomenon generating errors of a heartbeat measurement may occur.

FIGS. 6 to 9 are views illustrating a heartbeat sensor for preventing a crosstalk phenomenon by disposing a member having a partition between a light receiving unit and a light emitting unit according to an embodiment of the present invention.

Figure 6A:
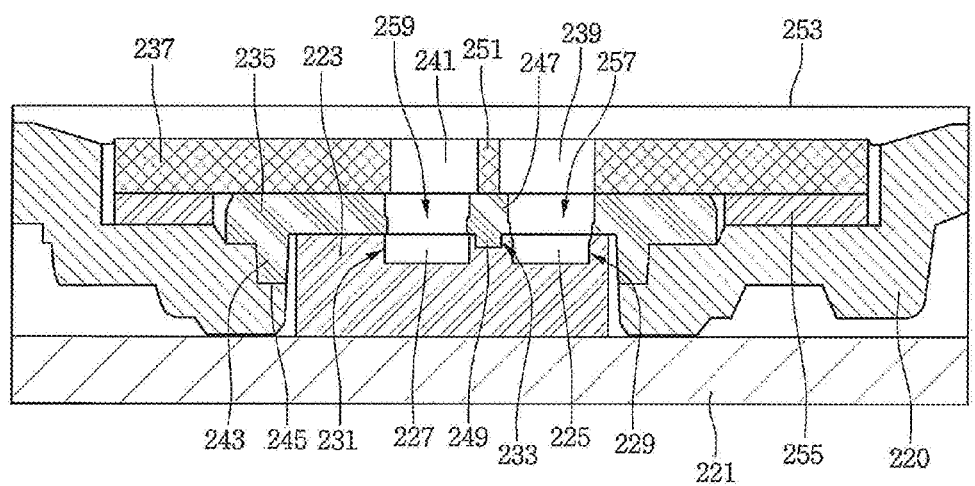
FIGS. 6(a), 6(b) and 6(c) are views illustrating a heartbeat sensor according to a first embodiment of the present invention.
Figure 6B:
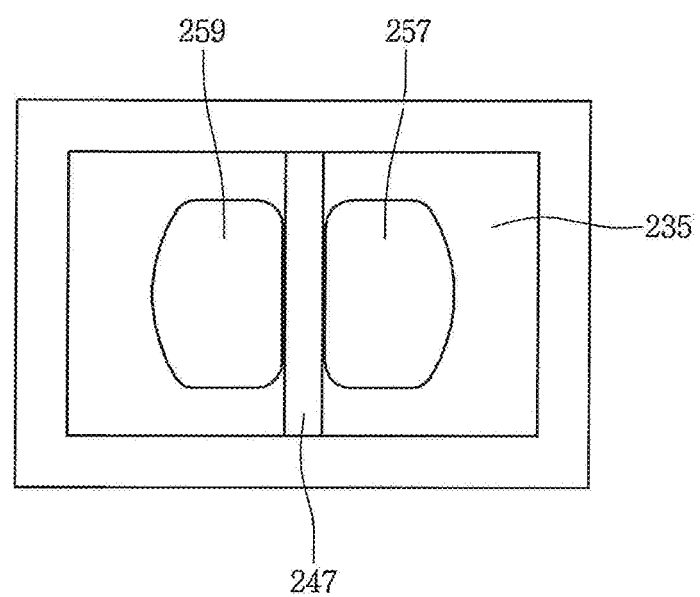
Figure 6C:
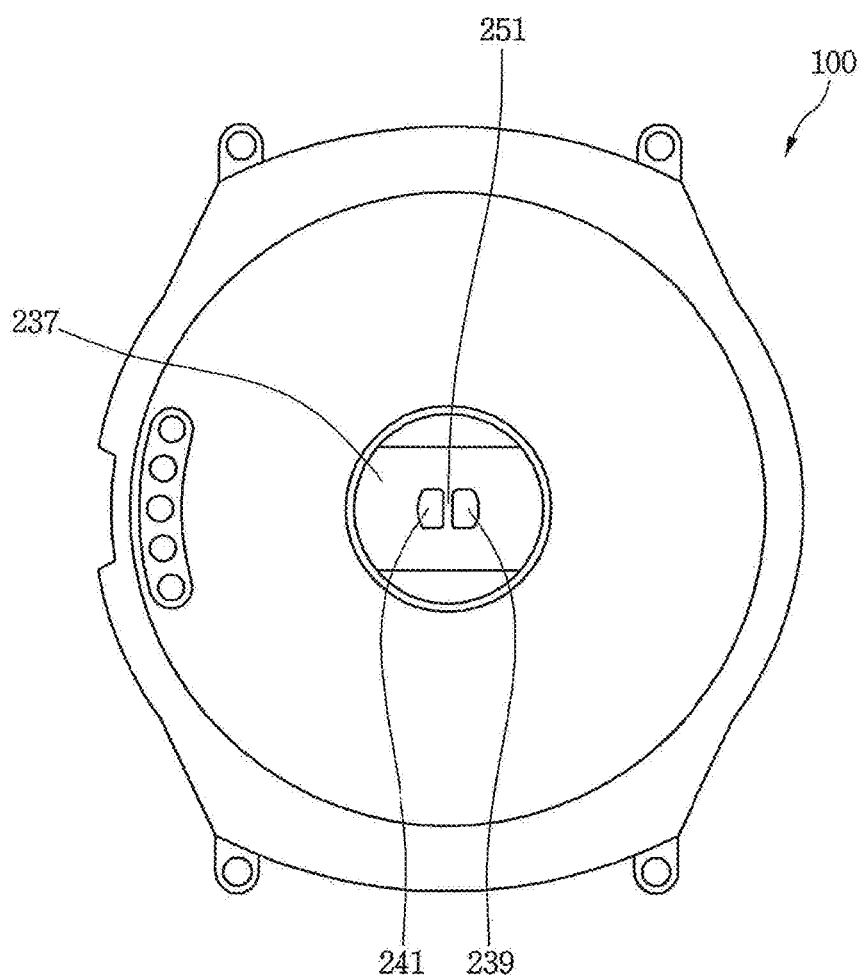

FIG. 6 is a view illustrating a heartbeat sensor according to a first embodiment of the present invention.

Referring to FIG. 6, the heartbeat sensor 144 may include a substrate 221, a main body 223, a light emitting unit 225, a light receiving unit 227, a first layer 235, a second layer 237, a housing 220, and a cover 253.

The light emitting unit 225 and the light receiving unit 227 may be mounted in the main body 223. The main body 223 may be formed of an insulating material having an excellent heat dissipation property such as epoxy or silicone. The light emitting unit 225 may be a red light emitting device and the light receiving unit 227 may be a photo diode.

The main body 223 may be mounted on the substrate 221. Each of the light emitting unit 225 and the light receiving unit 227 may be electrically connected to the substrate 221 through the main body 223. The substrate 221 may include a first conductive pattern electrically connected to the light emitting unit 225 and a second conductive pattern electrically connected to the light receiving unit 227.

The main body 223 may include first to third recesses 229, 231, and 233. For example, the light emitting unit 225 may be inserted and mounted in the first recess 229. For example, the light receiving unit 227 may be inserted and mounted in the second recess 231. For example, a protruding part 249 protruding from the partition 247 of the first layer 235 toward the bottom direction may be seated in the third recess 233.

The depth of the first recess 229 is identical to the thickness of the light emitting unit 225; the depth of the second recess 231 is identical to the thickness of the light receiving unit 227; and the depth of the third recess 233 may be identical to the thickness of the protruding part 249. However, the present invention is not limited thereto.

Each of the first to third recesses 229, 231, and 233 may have a bottom surface and an inner side surface having a predetermined depth from the top surface of the main body 223.

The light emitting unit 225 may be inserted into the first recess 229 and mounted on the bottom surface. The light receiving unit 227 may be inserted into the second recess 231 and mounted on the bottom surface. The protruding part 249 protruding from the partition 247 of the first layer 235 may be inserted into the third recess 233 and mounted on the bottom surface. The side surface of the light emitting unit 225 may contact the inner side surface of the first recess 229; the side surface of the light receiving unit 227 may contact the inner side surface of the second recess 231; and the side surface of the protruding part 249 of the first layer 235 may contact the inner side surface of the third recess 233. However, the present invention is not limited thereto.

The light emitting unit 225 may be attached to the bottom surface and the inner side surface of the first recess 229 by using an adhesive member with an insulating property as a medium; the light receiving unit 227 may be attached to the bottom surface and the inner side surface of the second recess 231 by using an adhesive member with an insulating property as a medium; and the protruding part 249 of the first layer may be attached to the bottom surface and the inner side surface of the third recess 233 by using an adhesive member with an insulating property as a medium. However, the present invention is not limited thereto.

Figure 7A:
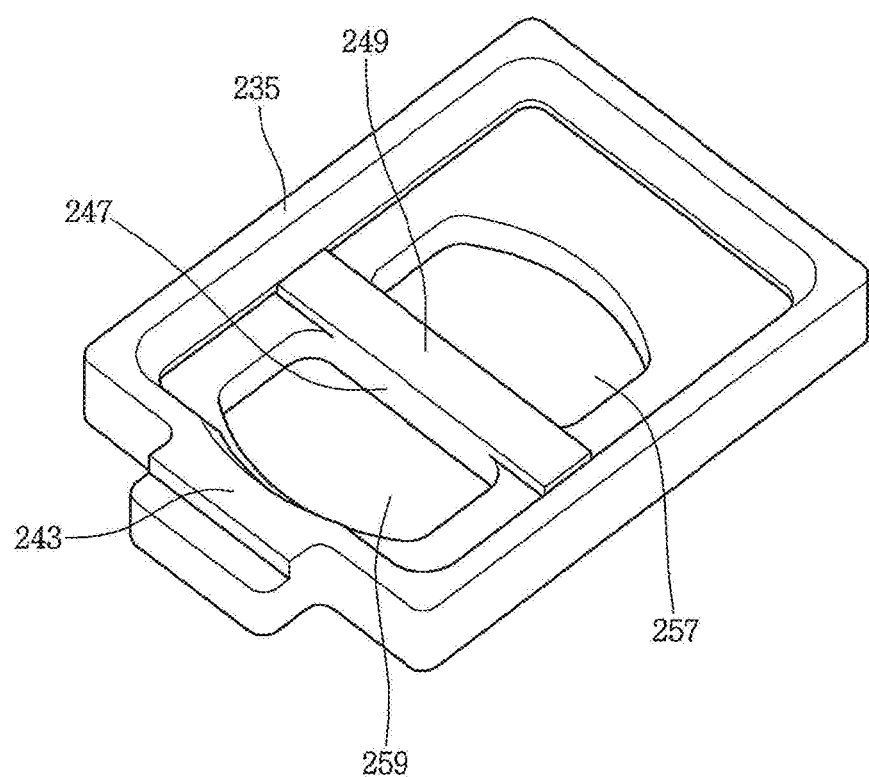
FIGS. 7(a) and 7(b) are views illustrating a first layer in the heartbeat sensor of FIG. 6.
Figure 7B:
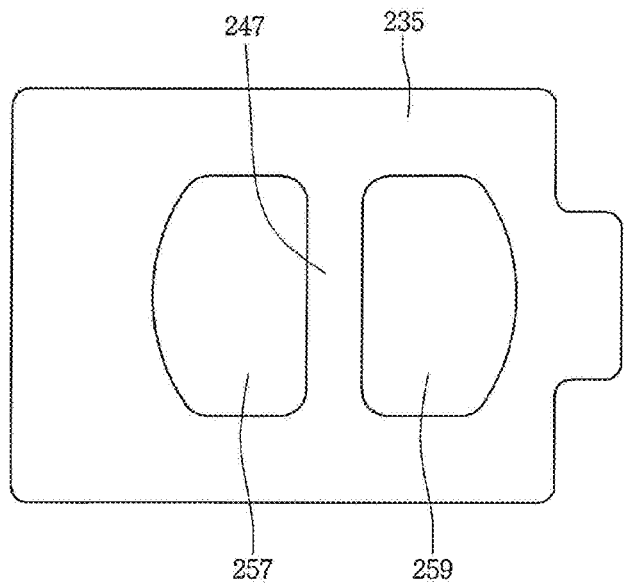

The first layer 235 may be disposed on the main body 223 where the light emitting unit 225 and the light receiving unit 227 are mounted. The first layer 235, as shown in FIGS. 7A and 7B, may include a catching part 243 formed along the frame, a partition 247 formed in the center area, and first and second openings 257 and 259 formed at both sides of the partition 247 on the basis of the partition 247. For example, the first opening 257 may correspond to the size of the top surface of the light emitting unit 225 and the second opening 259 may correspond to the size of the top surface of the light receiving unit 227. Each of the first and second openings 257 and 259 may have a circular, oval, square, or rectangular form, but the present invention is not limited thereto.

As another example, the partition 247 may be an additional member formed of a different material than the first layer 235.

The main body 223 may be covered by the first layer 235. The catching part 243 of the first layer 235 may be fixed at a catching ledge 245 of the housing 220. Accordingly, since the first layer 235 is fixed at the housing 220, the first layer 235 does not move.

The bottom surface of the first layer 235 may contact the top surface of the main body 223 and the protruding part 249 protruding from the partition 247 of the first layer 235 may contact the bottom surface of the third recess 233 of the main body 223. Therefore, since a path between the light emitting unit 225 and the light receiving unit 227 are blocked completely by the partition 247 and the protruding part 249 of the first layer 235, a light from the light emitting unit 225 and reflected by the first window 239 without passing through a user's wrist through the first window 239 is blocked by the partition 247 and the protruding part 249 and thus is not incident to the light receiving unit 227. Accordingly, it is possible to prevent heartbeat measurement errors due to a crosstalk phenomenon in which a light is generated from the light emitting unit 225 and incident to the light receiving unit 227 without passing through a user's wrist, so that the measurement performance of the heartbeat sensor 144 may be enhanced and thus, its reliability may be improved.

The width of the protruding part 249 may be identical to or narrower than the width of the third recess 233. The width of the protruding part 249 may be narrower than the width of the partition 247 of the first layer 235. Accordingly, the protruding part 249 is inserted into the third recess 233, and the remaining bottom surface excluding the protruding part 249 in the bottom surface of the partition 247 contacts the top surface of the central area of the main body 223. Therefore, by the remaining bottom surface excluding the protruding part 249 in the bottom surface of the protruding part 249 and the partition 247, the first layer 235 may be strongly fixed to the main body 223.

The first layer is formed of a material having elasticity and blocking light, for example, rubber, but the present invention is not limited thereto.

The second layer 237 may be disposed on the first layer. The second layer 237 may include first and second windows 239 and 241. The first and second windows 239 and 241 may be a transparent glass or plastic material. Each of the first and second windows 239 and 241 may be a circular or oval form but the present invention is not limited thereto.

The first window 239 may correspond to the size of the top surface of the light emitting unit 225 through the first opening 257 of the first layer and the second window 241 may correspond to the size of the top surface of the light receiving unit 227 through the second opening 259 of the first layer 235.

The partition 251 may be disposed between the first and second windows 239 and 241. The partition 251 may be a part of the second layer 237 but the present invention is not limited thereto.

The width of the partition 251 of the second layer 237 may be formed smaller than the width of the partition 247 of the first layer 235, thereby allowing the more light passing through the first opening 257 of the first layer 235 to progress toward a user's wrist and allowing the more light reflected by a user's wrist to be incident to the light receiving unit 227 through the second opening 259 of the first layer 235.

The partition 251 may have an integrated form formed of the same material as the second layer 237 or may be an additional member formed of a different material than the second layer 237.

The second layer may be formed of a material for blocking light, for example, a plastic material or rubber, but the present invention is not limited thereto.

Each of the first and second windows 239 and 241 may be surrounded by the second layer 237 and the partition 251.

When the size of the second layer 237 is greater than the size of the first layer 235 and the center point of the first layer 235 and the center point of the second layer 237 match, a peripheral area of the second layer 237 may extend from the end of the first layer 235 toward the outside direction. In such a case, a support part 255 is disposed between a peripheral area of the second layer 237 and the housing 220 in order to prevent the peripheral area of the second layer 237 from sagging down. That is, the bottom surface of the support part 255 may contact the housing 220 and the top surface of the support part 255 may contact the peripheral area of the second layer 237. The support part 255 may be attached to the top surface of the housing 220 and the bottom surface of the second layer 237 by using an adhesive material as a medium.

The light generated from the light emitting unit 225 may be emitted to the outside through the first opening 257 of the first layer 235 and the first window 239 of the second layer 237. The light reflected by a user's wrist may be incident to the light receiving unit 227 through the second window 241 of the second layer 237 and the second opening 259 of the first layer 235. In such a way, by the partition 247 and the protruding part 249 of the first layer 235 and the partition 251 of the second layer 237, only the light generated from the light emitting unit 225 and reflected by a user's wrist is incident to the light receiving unit 227 so that heartbeat measurement errors due to a crosstalk phenomenon may be prevented.

A cover 253 may be disposed on the second layer 237. The cover 253 may be formed of a plastic material but the present invention is not limited thereto. The cover 253 may be transparent or may not be transparent.

A peripheral area of the cover 253 may be fixed at or coupled to the housing 220.

Figure 8:
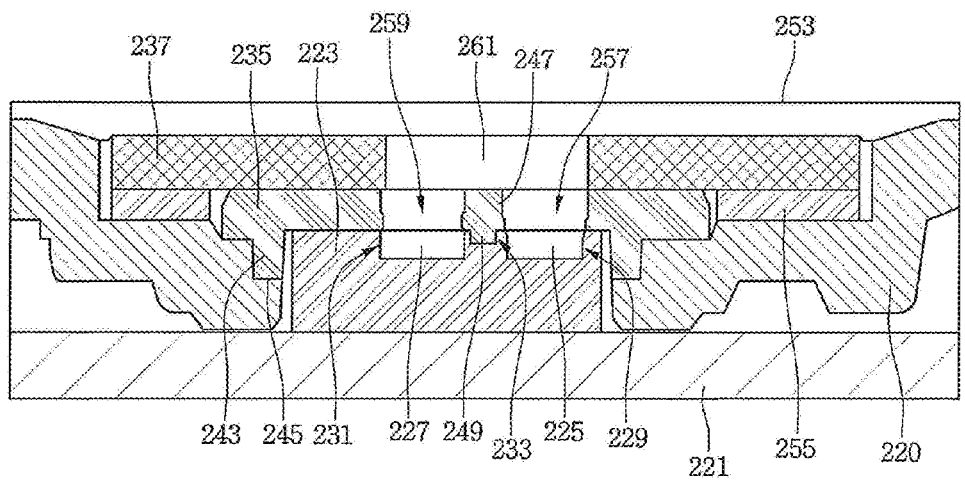
FIG. 8 is a view illustrating a heartbeat sensor according to a second embodiment of the present invention.

FIG. 8 is a view illustrating a heartbeat sensor according to a second embodiment of the present invention.

Except that the partition 251 of the second layer 237 is removed and the first and second windows 239 and 241 are integrally formed in the first embodiment, the second embodiment is similar to the first embodiment. In the second embodiment, the same reference numerals are assigned to components having the same structure, form, and function as the components of the first embodiment, and detailed description thereof will be omitted.

As shown in FIG. 8, the second layer 237 may be disposed on the first layer. The second layer 237 may include a window 261. The window 261 may be surrounded by the second layer 237. The window 261 may be a circular or oval form but the present invention is not limited thereto.

The size of the window 261 may be at least greater than the sum of the size of the first opening 257 of the first layer 235, the size of the second opening 259, and the size of the partition 247. Accordingly, the light generated from the light emitting unit 225 and passing through the first opening 257 of the first layer 235 may progress toward a user's wrist through the window 261 without loss. Moreover, the light reflected by a user's wrist may be incident to the light receiving unit 227 through the window 261 and the second opening 259 of the first layer 235.

Figure 9:
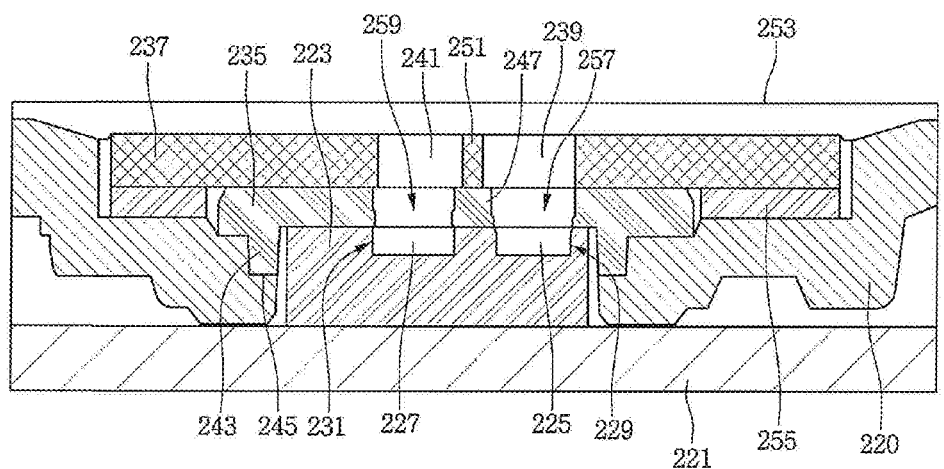
FIG. 9 is a view illustrating a heartbeat sensor according to a third embodiment of the present invention.

FIG. 9 is a view illustrating a heartbeat sensor according to a third embodiment of the present invention.

Except that the protruding part 249 of the first layer 235 is removed and the third recess 233 of the main body 223 where the protruding part 249 of the first layer 235 is inserted is removed in the first embodiment, the third embodiment is similar to the first embodiment. In the third embodiment, the same reference numerals are assigned to components having the same structure, form, and function as the components of the first embodiment, and detailed description thereof will be omitted.

As shown in FIG. 9, the top surface of a main body 223 may include first and second recesses 229 and 231. A light emitting unit 225 may be inserted and mounted into the first recess 229 and a light receiving unit 227 may be inserted and mounted into the second recess 231.

In the top surface of the center area of the main body 223 between the first recess 229 and the second recess 231, that is, the area where the third recess 233 is formed in the first embodiment, the top surface of a peripheral area of the main body 223 may have the same position.

The bottom surface of each of the first recess 229 and/or the second recess 231 may have a lower position by a depth set from the center area of the main body 223 and/or the top surface of a peripheral area of the main body 223.

The predetermined depth may be identical to the thickness of the light emitting unit 225 and/or the light receiving unit 227 but the present invention is not limited thereto.

The first layer 235 may be disposed on the main body 223 where the light emitting unit 225 and the light receiving unit 227 are mounted. The first layer 235 may include first and second openings 257 and 259, a partition 247 formed between the first and second openings 257 and 259, and a catching part 243 extending from a peripheral area of the first layer 235 toward the bottom direction.

The thickness of the partition 247 may be identical to the thickness of the first layer 235 but the present invention is not limited thereto.

The bottom surface of the partition 247 of the first layer 235 contacts the top surface of the center area of the main body 223, thereby preventing the light of the light receiving unit 225 from being incident to the light receiving unit 227. For this, a pressure applied in the bottom direction occurs by the cover 253 and this pressure is applied to the second layer 237. By the pressure applied to the second layer 237, the partition 247 of the first layer 235 is pressed in the bottom direction so that the partition 247 of the first layer 235 may easily contact the top surface of the center area of the main body 223.

As another example, the bottom surface of the first layer 235 may be attached to the top surface of the main body 223 by using an adhesive member as a medium. By such an adhesive, the bottom surface of the partition 247 of the first layer 235 strongly contacts the top surface of the center area of the main body 223, thereby stably maintaining the contact state.

In consideration of this, like the first embodiment, the protruding part 249 is provided on the first layer 235 so that the protruding part 249 is inserted and mounted into the third recess 233 of the main body 223 and also in a structure where the partition 251 is provided at the second layer 237 between the first and second windows 239 and 241, the removal rate of the crosstalk phenomenon is 100% so that the crosstalk phenomenon may be completely removed.

As above, since the crosstalk phenomenon is completely removed by the heartbeat sensor 144 according to the first to third embodiments, heartbeat measurement errors due to the crosstalk phenomenon are prevented so that the measurement performance of the heartbeat sensor 144 may be enhanced and thus, its reliability may be improved.

Figure 10:
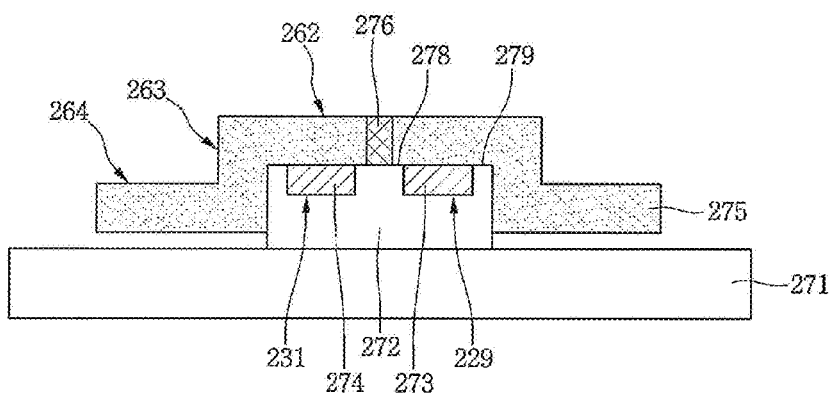
FIG. 10 is a view illustrating a heartbeat sensor according to a fourth embodiment of the present invention.
Figure 11:
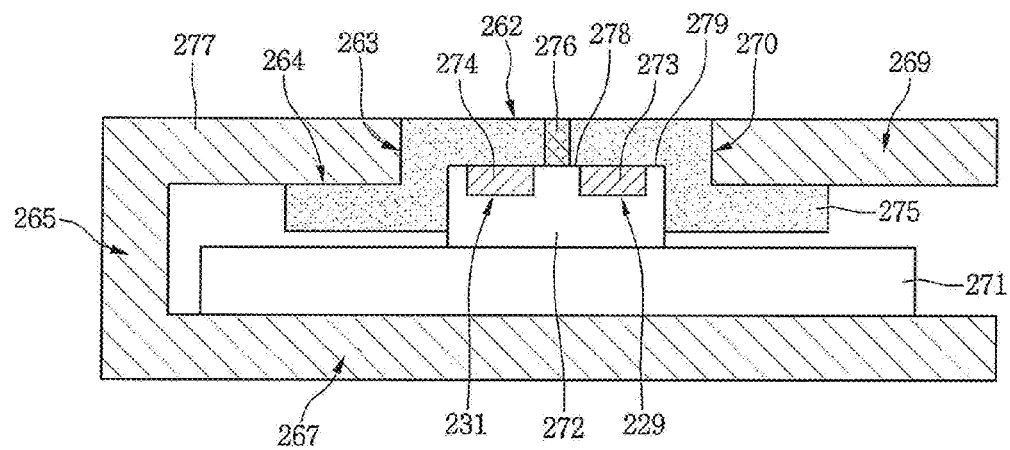
FIG. 11 is a view illustrating a heartbeat sensor according to a fifth embodiment of the present invention.

FIGS. 10 and 11 illustrate a heartbeat sensor for preventing a crosstalk phenomenon without using a first layer included in the heartbeat sensors of the first to third embodiments.

FIG. 10 is a view illustrating a heartbeat sensor according to a fourth embodiment of the present invention.

Referring to FIG. 10, a main body 272 is mounted on a substrate 271 and a light emitting 273 and a light receiving unit 274 may be spaced apart from each other and mounted in the main body 272.

The main body 272 may have a center area and a peripheral area. First and second recesses 229 and 231 may be formed between the center area of the main body 272 and the peripheral area of the main body 272.

The top surface of the center area of the main body 272 and the top surface of the peripheral area of the main body 272 may have the same position but the present invention is not limited thereto.

Each of the first and second recesses 229 and 231 may have a bottom surface and an inner side surface having a predetermined depth from the top surface of the main body 272.

The light emitting unit 273 may be inserted into the first recess 229 and mounted on the bottom surface. The light receiving unit 274 may be inserted into the second recess 231 and mounted on the bottom surface. The side surface of the light emitting unit 273 may contact the inner side surface of the first recess 229 and the side surface of the light receiving unit 274 may contact the inner side surface of the second recess 231. However, the present invention is not limited thereto.

The light emitting unit 273 may be attached to the bottom surface and the inner side surface of the first recess 229 by using an adhesive member with an insulating property as a medium; and the light receiving unit 274 may be attached to the bottom surface and the inner side surface of the second recess 231 by using an adhesive member with an insulating property as a medium. However, the present invention is not limited thereto.

A cover 275 may be disposed on the main body 272. The cover 275 may be formed to surround the main body 272. In more detail, the cover 275 may contact the top surface of the main body 272 and also may contact a side surface of the main body 272.

In the drawings, in consideration of a tolerance margin between the bottom surface of the cover 275 and the top surface of the substrate 271, the bottom surface of the cover 275 and the substrate 271 may be spaced apart from each other but the bottom surface of the cover 275 may contact the top surface of the top surface of the substrate 271.

The cover 275 may include first to third areas 262, 263, and 264. The first area 262 of the cover 275 may contact the top surface of the main body 272. The second area 263 of the cover 275 may be bent from the end of the first area 262 of the cover 275 toward the bottom direction to contact a side surface of the main body 272. The third area 264 of the cover 275 may extend from the end of the second area 263 of the cover 275 toward the outside direction and may be formed.

As another example, the third area 264 may be removed and the cover 275 including the first and second areas 262 and 263 may be provided.

As another example, the second and third areas 263 and 264 may be formed of a material for blocking light, for example, a plastic material. Accordingly, loss may be prevented when the light generated from the light emitting unit 273 and incident to the cover 275 does not progress toward a user's wrist or the light reflected by a user's wrist and incident to the cover 275 is not incident to the light receiving unit 274 and progresses along the second and third areas 263 and 264 of the cover 275.

The cover 275 may be formed of a transparent material having an excellent transmittance, for example, a glass or plastic material. Accordingly, the light generated from the light emitting unit 273 or the light reflected by a user's wrist may freely pass through the cover 275.

A partition 276 may be provided to the cover 275. In more detail, the partition 276 may be disposed at a position corresponding to the center area of the main body 272 between the light emitting unit 273 and the light receiving unit 274. The partition 276 may be inserted and fixed to the cover 275 through molding processing. The partition 276 may be formed of a material for blocking light, for example, a plastic material.

For example, when the cover 275 is formed of glass and the partition 276 is formed of a plastic material, by forming an opening at the cover 275 and injecting a plastic material for forming the partition 276 into the opening and then curing it, the cover 275 with the partition 276 may be manufactured. When seen from the top, the partition 276 may have a rectangular form but the present invention is not limited thereto.

The partition 276 may be surrounded by the cover 275.

The bottom surface of the partition 276 may contact the top surface of the center area of the main body 272. Since the width of the partition 276 is formed narrower than the width of the center area of the main body 272, the more light generated from the light emitting unit 274 is incident to a user's wrist through the cover 275 and the more light reflected by a user's wrist may be incident to the light receiving unit 274 through the cover 275.

Although not shown in the drawing, the cover 275 or the partition 276 may contact the main body 272 by using an adhesive member as a medium but the present invention is not limited thereto.

According to the fourth embodiment, as the partition 276 is provided to the cover 275, the cover 275 is disposed to directly contact the main body 272 so that like the first to third embodiments, a crosstalk phenomenon may be prevented without an additional first layer with the partition 276.

FIG. 11 is a view illustrating a heartbeat sensor according to a fifth embodiment of the present invention.

Except for the housing 277, the fifth embodiment is identical to the fourth embodiment.

As shown in FIG. 11, the substrate 271, the main body 272, and the cover 275 may be received and fixed by the housing 277. The housing 277 may be formed of a material having excellent elasticity and hardness, for example, a plastic material, but the present invention is not limited thereto.

The housing 277, for example, may have a " ⊏ " form. In more detail, the housing 277 may include first to third areas 265, 267, and 269.

The first area 265 of the housing 277 may be disposed at one sides of the substrate 271 and the cover 275. Although it is shown in the drawing that the inner side surface of the first area 265 is spaced apart from the side surface of the substrate 271, the inner side surface of the first area 265 may contact the side surface of the substrate 271.

The second area 267 of the housing 277 may extend from one end of the first area 265 in the horizontal direction and may be formed. The second area 267 of the housing 277 may contact the bottom surface of the substrate 271. In more detail, the second area 267 of the housing 277 may be attached to the bottom surface of the substrate 271 by using an adhesive member as a medium.

The third area 269 of the housing 277 may extend from the other end of the first area 265 in the horizontal direction and may be formed. The third area 269 of the housing 277 may have an opening 270. The size of the opening 270 is formed to be identical to the size of the first area 262 of the cover 275 so that the first area 262 of the cover 275 may be inserted into the opening 270 of the housing 277. The third area 269 of the housing 277 may be attached to the second area 263 and the third area 264 of the cover 275 by using an adhesive member as a medium.

According to the fifth embodiment, since the housing 277 fixes the substrate 271 disposed below the main body 272 where the light emitting unit 273 and the light receiving unit 274 are mounted and the cover 275 disposed over the main body 272, this may enhance the product robustness of a heartbeat sensor.

Figure 12A:
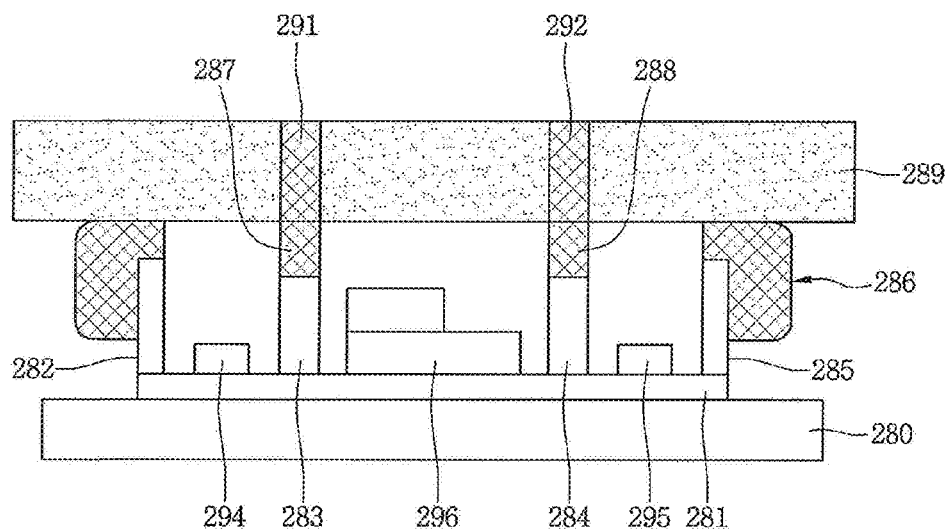
FIGS. 12(a) and 12(b) are views illustrating a heartbeat sensor according to a sixth embodiment of the present invention.
Figure 12B:
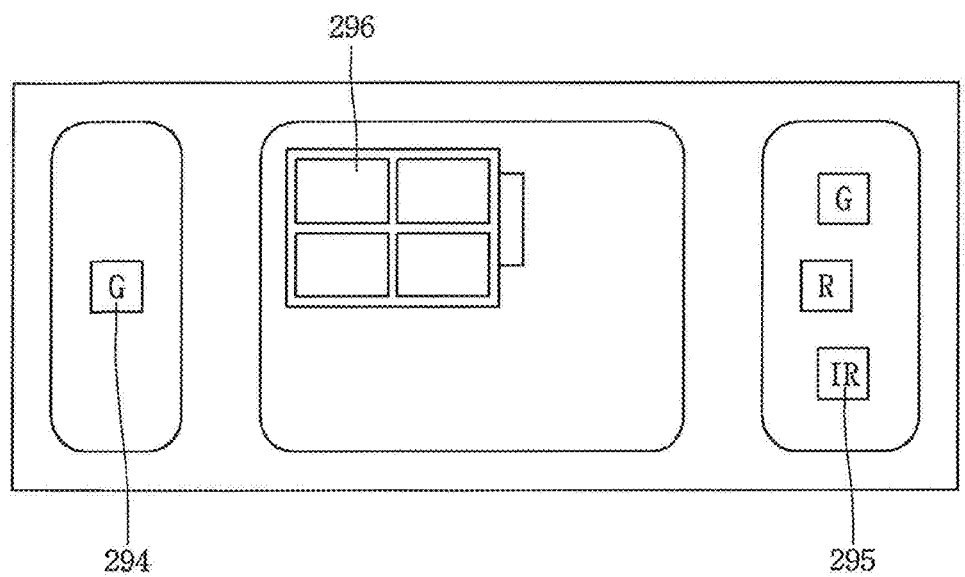
Figure 13:
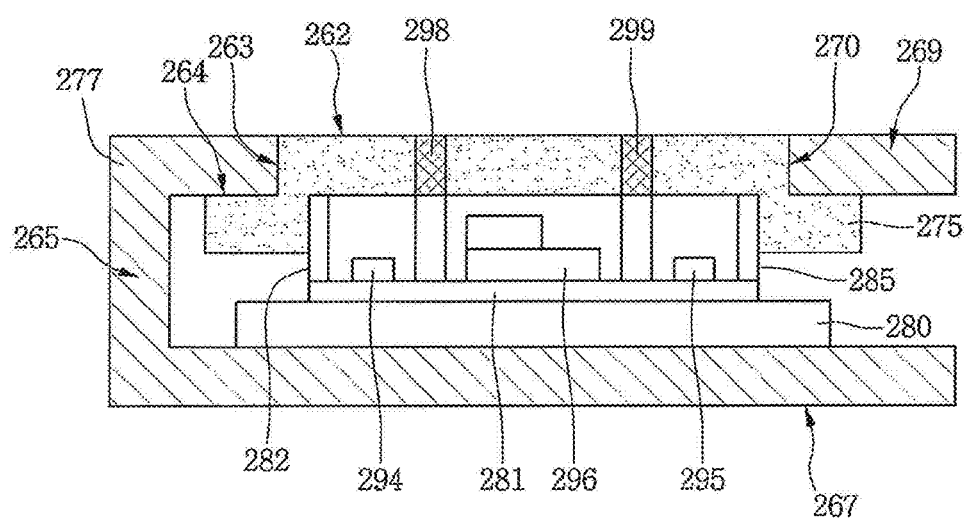
FIG. 13 is a view illustrating a heartbeat sensor according to a seventh embodiment of the present invention.

FIGS. 12 and 13 illustrate a heartbeat sensor where light emitting units are disposed at both sides of a light receiving unit.

FIG. 12 is a view illustrating a heartbeat sensor according to a sixth embodiment of the present invention.

Referring to FIG. 12, a heartbeat sensor 144 according to the sixth embodiment may include one or more light emitting units 294 and 295 and a light receiving unit 296.

For example, the first light emitting unit 294 may be disposed at one side of the light receiving unit 296 and the second light emitting unit 295 may be disposed at the other side of the light receiving unit 296.

The first light emitting unit 294 may include at least one light emitting device. For example, the first light emitting unit 294 may include a green light emitting device.

The second light emitting unit 295 may include a plurality of light emitting devices. For example, the second light emitting unit 295, for example, an infrared light emitting device, a red light emitting device, and a green light emitting element. A red light emitting device may be disposed between an infrared light emitting device and a green light emitting device but the present invention is not limited thereto.

Since the red light of a red light emitting device penetrates a skin further deeply in comparison to the green light of a green light emitting device, for example, the red light emitting device may be used to measure the heartbeat of a user's wrist of a relatively thin skin and the green light emitting device may be used to measure the heartbeat of a user's finger of a relatively thick skin. The infrared light emitting device may be used to detect whether an object is close.

The first and second light emitting units 294 and 295 and the light receiving unit 296 may be mounted on the substrate 280. The first and second light emitting units 294 and 295 and the light receiving unit 296 may be electrically connected to the substrate 280. Accordingly, the first and second light emitting units 294 and 295 operate by power so that light may be generated from the first and second light emitting units 294 and 295.

A plurality of partitions 282, 283, 284, and 285 may be disposed on the substrate 280. In more detail, the first and fourth partitions 282 and 285 may be disposed on the both sides of the substrate 280; the second partition 283 may be disposed between the first light emitting unit 294 and the light receiving unit 296; and the third partition 284 may be disposed between the light receiving unit 296 and the second light emitting unit 295.

Each of the first light emitting unit 294 or the second light emitting unit 295 may have a self-luminous radiation angle (hereinafter referred to as a first light emission radiation angle). Each of the first light emitting unit 294 or the second light emitting unit 295 may have a self-luminous radiation angle, for example, a range of about 90° to about 150°.

However, the first light emission radiation angle of each of the first light emitting unit 294 or the second light emitting unit 295 may change into a second light emission radiation angle by the height of each of the partitions 282, 283, 284, and 285.

The second light emission radiation angle may be smaller than the first light emission radiation angle by the height of each of the partitions 282, 283, 284, and 285. That is, even when the first light emission radiation angle is larger than the second light emission radiation angle, the first light emission radiation angle becomes smaller as the second light emission radiation angle by the height of each of the partitions 282, 283, 284, and 285.

For example, the second light emission radiation angle may have a range of about 90° to about 120°. In more detail, the second light emission radiation angle may have about 90°.

As the height of each of the partitions 282, 283, 284, and 285 is higher, the second light emission radiation angle may become smaller, and as the height of each of the partitions 282, 283, 284, and 285 is lower, the second light emission radiation angle may become larger.

In the same manner, the light receiving unit 296 may have a self light reception radiation angle (hereinafter referred to as a first light reception radiation angle). The self light reception radiation angle of the light receiving unit 296, for example, may have a range of about 90° to about 150°.

However, the first light reception radiation angle of the light receiving unit 296 may change into a second light reception radiation angle by the height of the second and/or third partition 283 and/or 284.

The second light reception radiation angle may become smaller than the first light reception radiation angle by the height of the second and/or third partition 283 and/or 284. That is, even if the first light reception radiation angle is larger than the second light reception radiation angle, the first light reception radiation angle becomes smaller as the second light reception radiation angle by the height of the second and/or third partition 283 and/or 284.

For example, the second light reception radiation angle may have a range of about 90° to about 120°. In more detail, the second light reception radiation angle may have about 120°.

As the height of the second and/or third partition 283 and/or 284 becomes higher, the second light reception radiation angle becomes smaller, and as the height of the second and/or third partition 283 and/or 284 becomes lower, the second light reception radiation angle becomes larger.

According to the sizes of the first light emitting unit 294, the second light emitting unit 295, and the light receiving unit 296, intervals between the partitions 282, 283, 284, and 285 may vary. For example, an interval between the second and third partition 283 and 284 may be greater than an interval between the first and second partitions 282 and 283 or an interval between the third and fourth partitions 284 and 285.

The first to fourth partitions 282, 283, 284, and 285 may be integrally formed with the substrate 280 or may be formed separately from the substrate 280.

The height of the second and/or third partition 283 and/or 284 may be lower than the height of the first and/or fourth partition 282 and/or 285. That is, the thickness of the second and/or third partition 283 and/or 284 may be thinner than the thickness of the first and/or fourth partition 282 and/or 285.

A layer 286 may be disposed on the first to fourth partitions 282, 283, 284, and 285.

The layer 286 is formed of a material having elasticity and blocking light, for example, rubber, but the present invention is not limited thereto.

The layer 286 may cover at least a part of the top surfaces of the first to fourth partitions 282, 283, 284, and 285 and the side surfaces of the first and fourth partitions 282 and 285. In more detail, the first area of the layer 286 may cover the second partition 283 and the second area of the layer 286 may cover the third partition 284. Herein, the first area of the layer 286 is referred to as the first partition 287 and the second area of the layer 286 is referred to as the second partition 288.

As another example, the first partition 287 and the second partition 288 may be formed as an additional member different from the layer 286. In such a case, the first and second partitions 287 and 288 may be formed of a material for blocking light, for example, a rubber or plastic material.

Each of the first and second partitions 287 and 288 may include a protruding area protruding from the bottom surface of the layer 286 toward the bottom direction. The bottom surface of the protruding area may contact each of the second and third partitions 283 and 284. As mentioned above, since the height of the second and/or third partition 283 and/or 284 is lower than the height of the first and/or fourth partition 282 and/or 285, a protruding area protruding from the bottom surface of the layer 286 toward the bottom direction by the lowered height may be formed.

As another example, the heights of all the first to fourth partitions 282 to 285 may be identical to each other. In such a case, the thickness of the first and second partitions 287 and 288 may be identical to the thickness of the layer 286.

A cover 289 may be disposed on the layer 286. The cover 289, as a transparent material, may be a plastic material or glass.

The cover 289 may include the first and second partitions 291 and 292. The first partition 291 of the cover 289 is disposed on the first partition 291 of the layer 286 and the second partition 292 of the cover 289 may be disposed on the second partition 292 of the layer 286.

The first and second partitions 291 and 292 may be inserted into the cover 289 and formed through molding processing.

The width of each of the first and second partitions 291 and 292 of the cover 289 may be identical to the width of each of the first and second partitions 287 and 288 of the layer 286 but the present invention is not limited thereto.

The first and second partitions 291 and 292 may be formed of a light blocking member for blocking light.

The first and second partitions 291 and 292 of the cover 289 and the first and second partitions 287 and 288 of the layer 286 may include the same material but the present invention is not limited thereto.

The bottom surfaces of the first and second partitions 291 and 292 of the cover 289 may respectively contact the top surfaces of the first and second partitions 287 and 288 of the layer 286. In more detail, the bottom surfaces of the first and second partitions 291 and 292 of the cover 289 may be respectively attached to the top surfaces of the first and second partitions 287 and 288 of the layer 286 by using an adhesive member as a medium.

FIG. 13 is a view illustrating a heartbeat sensor according to a seventh embodiment of the present invention.

A cover 275 and a housing 277 shown in FIG. 13 may be identical to the cover 275 and the housing 277 shown in FIG. 11.

As shown in FIG. 13, the cover 275 may contact the top surfaces of the first to fourth partitions 282 to 285 and the side surfaces of the first and fourth partitions 282 and 285. The first to fourth partitions 282, 283, 284 and 285 are fixed by the cover 275 and a crosstalk phenomenon may be prevented by the first and second partitions 298 and 299 of the cover 275.

The cover 275 may include the first to third areas 262, 263, and 264. The second area 263 of the cover 275 may extend from both ends of the first area 262 of the cover 275 toward the bottom direction and may be formed, and the third area 264 of the cover 275 may extend from the end of the second area 263 of the cover 275 toward the outside direction and may be formed.

In more detail, the first and second partitions 298 and 299 may respectively contact the second and third partitions 283 and 284; the first area 262 of the cover 275 may contact the top surfaces of the first and fourth partitions 282 and 285; and the second area 263 of the cover 275 may contact the side surfaces of the first and fourth partitions 282 and 285.

The cover 275 and the substrate 280 may be fixed by the housing 277. The housing 277 may be attached to the substrate 280 and the cover 275 by using an adhesive member as a medium. The housing 277 may be attached to the bottom surface of the substrate 280 and may be attached to the second area 263 and the third area 264 of the cover 275.

The housing 277 may include first to third areas 265, 267, and 269. The second area 267 of the housing 277 may extend from one end of the first area 265 of the housing 277 toward the horizontal direction and may be formed, and the third area 269 of the housing 277 may extend from the other end of the first area 265 of the housing 277 toward the horizontal direction and may be formed.

The second area 267 of the housing 277 may contact the bottom surface of the substrate 280. In more detail, the second area 267 of the housing 277 may contact the bottom surface of the substrate 280 by using an adhesive member as a medium. Furthermore, the third area 269 of the housing 277 may be attached to the second area 263 and the third area 264 of the cover 275 by using an adhesive member as a medium.

The third area 269 of the housing 277 may have an opening 270. The size of the opening 270 is formed to be identical to the size of the first area 262 of the cover 275 so that the first area 262 of the cover 275 may be inserted into the opening 270 of the housing 277.

According to the sixth and seventh embodiments, in a heartbeat sensor where the first and second light emitting units 294 and 295 are disposed at both sides of the light receiving unit 296, a crosstalk phenomenon is prevented by using the partitions 283, 284, 287, 288, 291, and 292 and thus product reliability may be improved.

Hereinafter, embodiments relating to control method that is to be implemented for the watch type device 100 configured in such a manner are described with reference to the accompanying drawings. It is apparent to those skilled in the art that the present invention may be specified in a different specific form without departing from the scope and essential features of the present invention.

The watch type device 100 may detect a wearing state of the watch type device 100 by a user and may execute a corresponding function according to a detection result, that is, not-wearing, wrist wearing, and hand gripping. Herein, not-wearing is referred to as a first mode; wrist wearing is referred to as a second mode; and hand gripping is referred to as a third mode.

For example, in the first mode and/or the third mode, a black screen or an ambient screen may be displayed.

For example, a standby screen may be displayed in the second mode.

In terms of power consumption, a black screen is displayed in the sleep mode; an ambient screen is displayed in the ambient mode; and a standby screen may be displayed in the normal mode.

In the sleep mode, as a screen off state, the power of the power supply unit 190 is not supplied to the screen so that a black screen may be displayed. In this case, since power is supplied a touch sensor provided at the display unit 151, touch recognition is possible.

In the standby mode, as a screen on state, the power of the power supply unit 190 is supplied to the screen so that a standby screen may be displayed.

Although the ambient mode is the screen on state, power lower than the power supplied to the standby screen is supplied to the screen so that the ambient screen having a lower brightness than the standby screen may be displayed.

In the ambient mode, a function not interfering with information delivery to a user while reducing power consumption, for example, providing a simple notification information, may be performed. Such a function may include missed call notification, schedule notification, calendar notification, remaining battery capacity notification, and weather notification but the present invention is not limited thereto.

In the normal mode, a function using power normally, for example, data transmission/reception, telephone calls, and video streams in addition to a watch function, may be performed.

For example, the standby screen may be displayed in the normal mode. The standby screen may include a digital watch screen, an analog watch screen, and a home screen including a plurality of icons. In more detail, in the normal mode, since a standby screen such as a digital watch screen, an analog watch screen, or a home screen is displayed by the power of the power supply unit 190, information in the high level of brightness may be displayed on the standby screen.

The wearing state of the watch type device 100 may be detected by the heartbeat sensor 144 and the acceleration sensor 143 provided at the watch type device 100.

The acceleration sensor 143 may detect a motion of the watch type device 100. The acceleration sensor 143 may generate an absolute motion detection (AMD) signal (for example, a first sensing signal) indicating a relatively small motion and a relative motion detection (RMD) signal (for example, a second sensing signal) indicating a relatively large motion.

Each of the AMD signal and the RMD signal may have "0" or "1". "0", as an inactive signal, may indicate no motion. "1" may be an active signal. When the AMD signal is "1", it indicates that a small motion is detected and when the RMD signal is "1", it indicates that there is a large motion.

For example, when the watch type device 100 is laid on a floor or a desk, since the watch type device 100 does not move, the acceleration sensor 143 of the watch type device 100 may output the AMD signal of "0" and the RMD signal of "0".

For example, when the watch type device 100 is worn by a user, since the watch type device 100 is shaking frequently, the acceleration sensor 143 of the watch type device 100 may output the AMD signal of "1" but may output the RMD signal of "0" or "1" according to the degree of shaking of the watch type device 100. That is, when the watch type device 100 has a relatively small shaking, the RMD signal of "0" may be outputted and when the watch type device 100 has a relatively large shaking, the RMD signal of "1" may be outputted. Since the AMD signal of "1" indicates that the watch type device 100 has a relatively small shaking, at this point, the RMD signal may be "0" or "1". On the other hand, when the RMD signal is "1", since this indicates that the watch type device 100 has a relatively large shaking, at this point, the AMD signal may be always "1".

TABLE 1

| AMD signal | RMD signal | State |
|---|---|---|
| 0 | 0 | Not-wearing |
| 1 | 0 | Wearing |
| 1 | 1 | Wearing |

As shown in Table 1, a distinction between not-wearing and wearing is possible by the acceleration sensor 143 but it is difficult to distinguish wrist wearing from hand gripping during wearing.

Wrist wearing and hand gripping may be distinguished by the heartbeat sensor 144.

Figure 14:
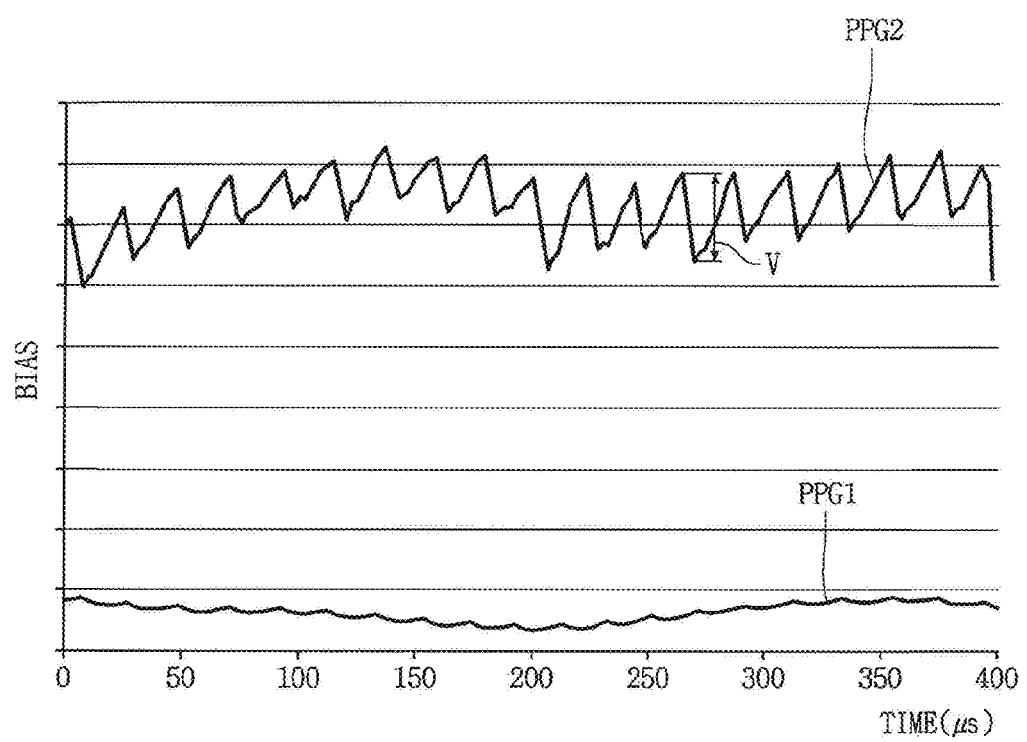
FIG. 14 is a view illustrating a waveform of a touch interrupt signal generated from a heartbeat sensor.

The heartbeat sensor 144 may generate a touch interrupt signal on the basis of the amount of light reflected by a user. A touch interrupt signal generated from the heartbeat sensor 144 may have a signal variation v and a bias as shown in FIG. 14. Herein, the bias may be the size of a touch interrupt signal.

For example, a first touch interrupt signal PPG1 has almost no signal change and a less bias. On the other hand, a second touch interrupt signal PPG2 has a relatively large signal variation v and a large bias.

The first touch interrupt signal PPG1 is a signal detected by a user's wrist and the second touch interrupt signal PPG2 is a signal detected by a user's finger.

As shown in FIG. 14, the size of a signal variation of the second touch interrupt signal PPG2 detected from a finger may be 15 to 20 times greater than the size of a signal variation of the first touch interrupt signal PPG1 detected from a wrist. Furthermore, a bias of the second touch interrupt signal PPG2 detected from a finger is significantly greater than a bias of the first touch interrupt signal PPG1 detected from a wrist.

For example, when the watch type device 100 is gripped by a finger, the second touch interrupt signal PPG2 may be detected from a user's finger.

For example, when the watch type device 100 is worn on a wrist, the first touch interrupt signal PPG1 may be detected from the user's wrist.

Accordingly, where the watch type device 100 is worn may be obtained on the basis of a touch interrupt signal detected from the heartbeat sensor 144.

As waveform information (for example, signal variation and bias) of the first touch interrupt signal PPG1 and waveform information of the second touch interrupt signal PPG2, shown in FIG. 14, are stored in the watch type device 100, a wearing state of the watch type device 100 may be obtained in detail on the basis of a touch interrupt signal detected from the heartbeat sensor 144.

Moreover, a heartbeat signal may be generated by the heartbeat sensor 144 and user authentication may be performed by using the heartbeat signal.

The principle of generating a touch interrupt signal or a heartbeat signal from the heartbeat sensor 144 is the same.

However, a touch interrupt signal or a heartbeat signal may be determined according to in which situation the heartbeat sensor 144 is used.

For example, in a wearing detection situation, a signal generated from the heartbeat sensor 144 may be used as a touch interrupt signal. As mentioned above, a touch interrupt signal may vary depending on whether the watch type device 100 is worn on a wrist or gripped by a hand.

Figure 37:
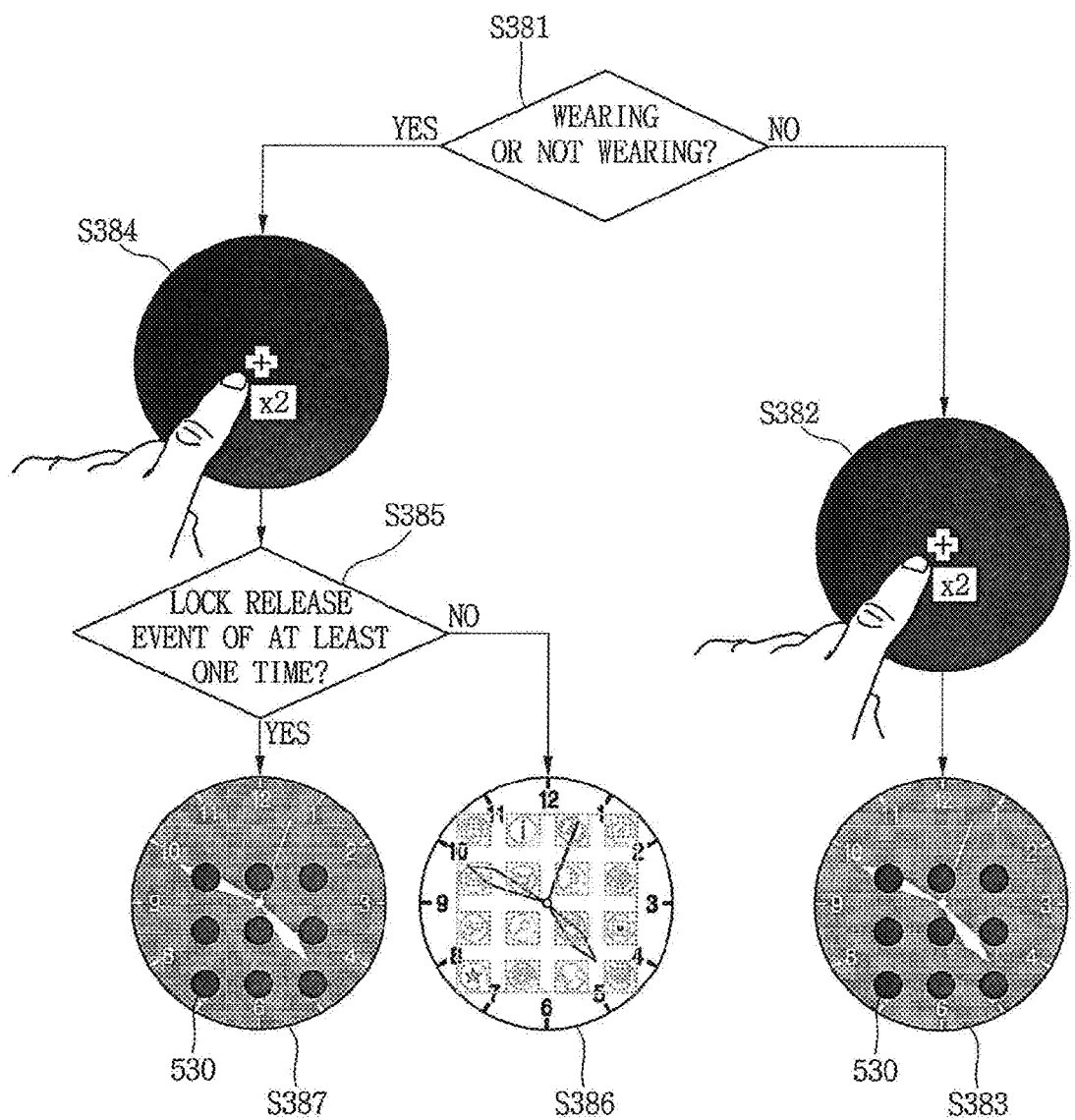
FIG. 37 is a flowchart illustrating a screen activating method and a lock releasing method according to wearing.

For example, in user authentication situation, a signal generated from the heartbeat sensor 144 may be used as a heartbeat signal. In the case of the same user, a heartbeat signal generated from the wrist of the user (that is, the owner) may the same each time it is measured. On the other hand, when the watch type device 100 is worn on another user's wrist, a heartbeat signal different from the heartbeat signal of the user (that is, the owner) may be generated. Accordingly, user authentication may be successfully performed by using different heartbeat signals for each user only if the watch type device 100 is worn on the wrist of a user (that is, an owner), and then subsequent operations may be performed. Such a user authentication process using a heartbeat signal generated from the heartbeat sensor 144 is shown in FIGS. 27 and 37 and this will be described later.

Figure 15:
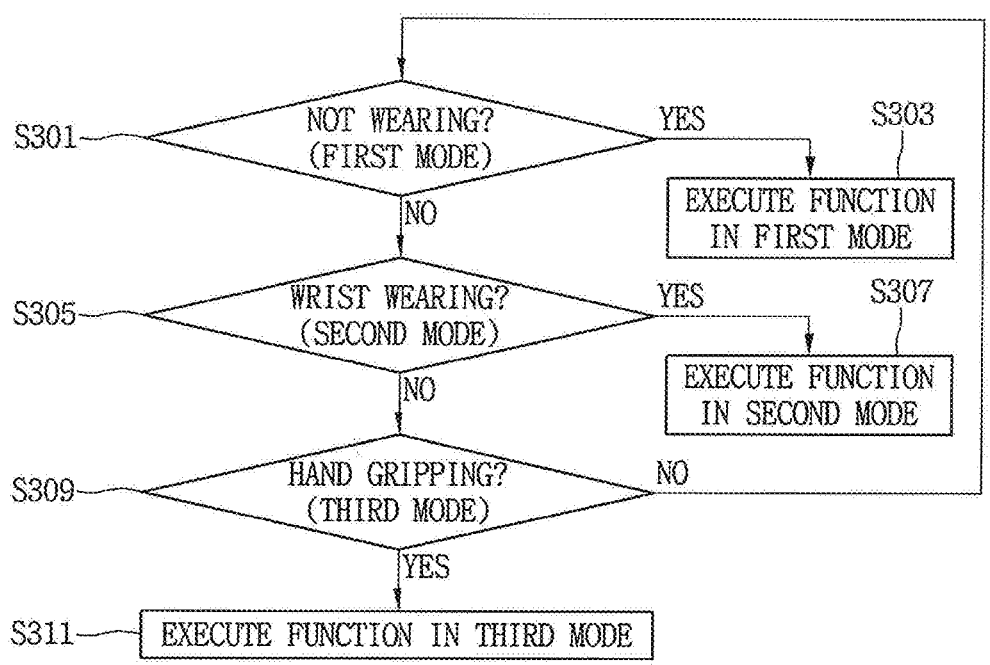
FIG. 15 is a flowchart illustrating a method of detecting whether a watch type device is worn according to an embodiment of the present invention.

FIG. 15 is a flowchart illustrating a method of detecting whether a watch type device is worn according to an embodiment of the present invention.

The watch type device 100 detects whether a user does not wear it (for example, a first mode) in operation S301.

In more detail, the acceleration sensor 143 of the watch type device 100 detects a shaking of the watch type device 100. The control unit 180 of the watch type device 100 may check whether the watch type device 100 is worn on the basis of a detection result of the acceleration sensor 143 of the watch type device 100.

When the AMD signal of "0" and the RMD signal of "0" are inputted from the acceleration sensor 143 of the watch type device 100 on the basis of a detection result, the control unit 180 of the watch type device 100 may determine that a user does not wear the watch type device 100.

When the RMD signal of "1" is inputted from the acceleration sensor 143 of the watch type device 100 on the basis of a detection result, the control unit 180 of the watch type device 100 may determine that a user wears the watch type device 100. Whether the AMD signal is "0" or "1" does not affect wearing state detection. That is, a value of the AMD signal is irrelevant to wearing state detection.

Although not shown in the drawings, when the RMD signal of "1" is inputted from the acceleration sensor 143 of the watch type device 100 and the RMD signal of "1" is maintained for more than 4 sec, the control unit 180 of the watch type device 100 may determine that the watch type device 100 is worn by a user, but the present invention is not limited thereto.

Although not shown in the drawing, it is determined whether an object is close by using an infrared light emitting device of the heartbeat sensor 144 shown in FIGS. 12 and 13. A not-wearing state or a wearing state may be detected by using an infrared light emitting device of the heartbeat sensor 144.

Although not shown in the drawings, a wearing state or a not-wearing state may be detected more accurately by using infrared light emitting devices of the acceleration sensor 143 and the heartbeat sensor 144.

As mentioned above, the acceleration sensor 143 of the watch type device 100 only distinguishes wrist wearing from not-wearing and cannot distinguish wrist wearing from hand gripping during wearing.

Referring to FIG. 15, when it is determined that the watch type device 100 is not worn by a user, the control unit 180 of the watch type device 100 executes a function of the watch type device 100 during not-wearing, that is, a function in the first mode, in operation S303.

For example, a black screen (see FIGS. 1 6A) may be displayed on the display unit 151 of the watch type device 100 during not-wearing. The black screen, as mentioned above, as a screen off state, may mean that power is not supplied to a screen. Separately, power is supplied to a touch sensor provided at the display unit 151 so that touch recognition is possible. In such a way, power is not supplied to a screen during not-wearing so that power consumption may be reduced.

For example, an ambient screen may be displayed on the display unit 151 of the watch type device 100 during not-wearing.

Moreover, a black screen or an ambient screen may be displayed during not-wearing and not all components are activated. That is, a minimum of components, for example, only the control unit 180, the sensing unit 140, the input unit 120, the wireless communication unit 110, and the output unit 150, may be activated.

If it is determined that the watch type device 100 is worn by a user, the control unit 180 of the watch type device 100 supplies (or activates) power to the heartbeat sensor 144 to operate the light emitting unit 225 and the light receiving unit 227.

The heartbeat sensor 144 of the watch type device 100 may generate a touch interrupt signal on the basis of the amount of light reflected from a user. The control unit 180 of the watch type device 100 may check a specific wearing state on the basis of a detection result of the heartbeat sensor 144, for example, wrist wearing and hand gripping.

As shown in FIG. 14, a signal variation and a bias of a touch interrupt signal detected from the heartbeat sensor 144 correspond to a signal variation and a bias of a first touch interrupt signal PPG1, the control unit 180 of the watch type device 100 may determine that the watch type device 100 is worn on a user's wrist.

Furthermore, a signal variation and a bias of a touch interrupt signal detected from the heartbeat sensor 144 correspond to a signal variation and a bias of a second touch interrupt signal PPG2, the control unit 180 of the watch type device 100 may determine that the watch type device 100 is gripped by a user's hand.

Referring to FIG. 15, the control unit 180 of the watch type device 100 detects whether a user wears the watch type device 100 by a wrist (for example, a second mode) in operation S305.

In more detail, when the AMD signal of "1" is outputted from the acceleration sensor 143 of the watch type device 100 and when a touch interrupt signal generated from the heartbeat sensor 144 of the watch type device 100 corresponds to a first touch interrupt signal PPG1 shown in FIG. 14, the control unit 180 of the watch type device 100 may determine that the watch type device 100 is worn on a user's wrist.

When it is determined that the watch type device 100 is worn by a user's wrist, the control unit 180 of the watch type device 100 executes a function of the watch type device 100 during wrist wearing, that is, a function in the second mode, in operation S307.

For example, a predetermined screen may be displayed on the display unit 151 of the watch type device 100 during wrist wearing. The predetermined screen, for example, may include an analog watch screen (see FIG. 16B), a digital watch screen (see FIG. 16C), a home screen including a plurality of icons, and simple notification information. Alternatively, a predetermined screen may be a black screen or an ambient screen.

The simple notification information may include numbers, characters, and images, or icons representing text message notification, SNS notification, e-mail notification, and so on. The simple notification information does not include detailed information of each notification, for example, when, from who, and what content. In order to view detailed information of each notification, after simple notification information is displayed, an additional event (or gesture) is performed or an authentication process is performed.

In the analog watch screen, it may be set that only hands and dials are represented with a white grayscale and the background is represented with a black grayscale to turn off its power. In the digital watch screen, it may be set that only time related numbers are represented with a white grayscale and the background is represented with a black grayscale to turn off its power. In such a way, since the background that occupies most of an analog watch screen or a digital watch screen does not require power supply, power consumption may be reduced.

Accordingly, even when an analog watch screen or a digital watch screen is displayed, since there is almost no power consumption, as long as a user wears the watch type device 100 by the wrist, the analog watch screen or the digital watch screen may be always displayed without turning off the screen. This is called an "always-on function".

As another example, a lock screen is displayed before a predetermined screen is displayed on the display unit 151 during wrist wearing and when lock release is performed on the lock screen, the predetermined screen may be displayed on the display unit 151.

As another example, when a predetermined screen displayed on the display unit 151 is a home screen including a plurality of icons during wrist wearing, a lock screen may be displayed before the predetermined screen is displayed on the display unit 151 and the home screen may be displayed when lock release is performed on the lock screen.

As another example, when a predetermined screen is a digital watch screen or an analog watch screen during wrist wearing, a lock screen may not be displayed before the predetermined screen is displayed. That is, since a digital watch screen or an analog watch screen does not require security, a lock release process is not required.

Referring to FIG. 15, the control unit 180 of the watch type device 100 detects whether a user grips the watch type device 100 by a hand (for example, a third mode) in operation S309.

In more detail, when the RMD signal of "1" is outputted from the acceleration sensor 143 of the watch type device 100 and when a touch interrupt signal of the watch type device 100 corresponds to a second touch interrupt signal PPG2 shown in FIG. 14, the control unit 180 of the watch type device 100 may determine that the watch type device 100 is gripped by a user's hand.

When it is determined that the watch type device 100 is gripped by a user's hand, the control unit 180 of the watch type device 100 executes a function of the watch type device 100 during hand gripping, that is, a function in the third mode, in operation S311.

For example, while the watch type device 100 is gripped by a hand, a black screen or an ambient screen may be displayed on the display unit 151 of the watch type device 100. In the black screen, as a screen off state, power is not supplied to a screen. In the ambient screen, as a screen on state, power lower than the power of the power supply unit 190 is supplied to the display unit 151, so that power consumption may be reduced.

In such a way, when the watch type device 100 is gripped by a hand, a black screen in a screen off state is displayed or an ambient screen in an on state is displayed while power lower than the power of the power supply unit 190 is supplied so that power consumption may be reduced.

As another example, when the watch type device 100 is gripped by a hand, an ambient screen including simple notification information may be displayed on the display unit 151 of the watch type device 100. Accordingly, a user may check simple notification information by gripping the watch type device 100 without wearing it by a wrist.

The simple notification information may include numbers, characters, images, or icons representing text message notification, SNS notification, e-mail notification, and so on. The simple notification information does not include detailed information of each notification, for example, when, who, and what content. In order to view detailed information of each notification, after simple notification information is displayed, an additional event (or gesture) is performed or an authentication process is performed.

In brief, the watch type device 100 may determine a first mode (for example, not-wearing), a second mode (for example, wrist wearing), and a third mode (for example, hand gripping) by using the acceleration sensor 143 and the heartbeat sensor 144 and may execute a function in the determined mode.

For example, a black screen may be displayed on the display unit 151 in the first mode.

For example, a black screen or an ambient screen may be displayed on the display unit 151 in the third mode.

For example, a standby screen instead of a black screen or an ambient screen may be displayed on the display unit 151 in the second mode. The standby screen may include an analog watch screen, a digital watch screen, and a home screen including a plurality of icons.

Hereinafter, wearing detection shown in FIG. 15 is described in detail.

Figure 17:
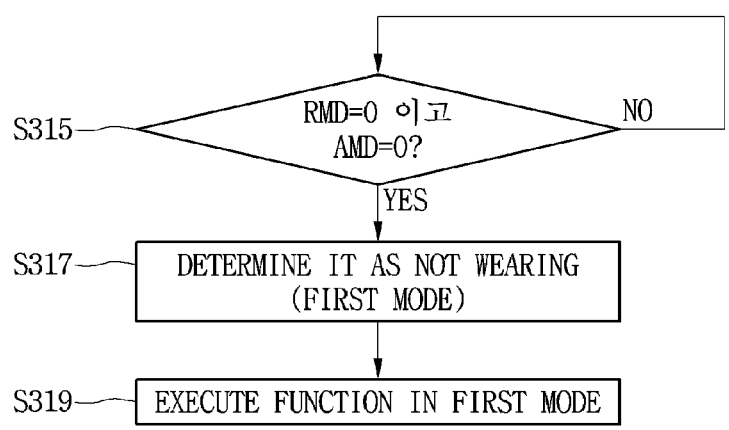
FIG. 17 is a flowchart illustrating a method of detecting a not-wearing state of the watch type device of FIG. 15 according to an embodiment of the present invention.

FIG. 17 is a flowchart illustrating a method of detecting a not-wearing state of the watch type device of FIG. 15 according to an embodiment of the present invention. FIG. 17 is a view embodying operations S301 and S303 of FIG. 15.

Referring to FIG. 17, the control unit 180 of the watch type device 100 checks whether the RMD signal outputted from the acceleration sensor 143 is "0" and the AMD signal is "0" in operation S315. When the RMD signal is "0" and the AMD signal is "0", the control unit 180 of the watch type device 100 determines it as not-wearing (that is, the first mode) in operation S317 and executes a function in the first mode in operation S319.

In determining a not-wearing state, the heartbeat sensor 144 may not be used. That is, a not-wearing state may be determined by using only the acceleration sensor 143 without using the heartbeat sensor 144.

Figure 16A:
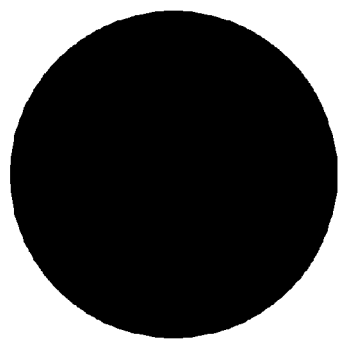
FIGS. 16(a), 16(b) and 16(c) are views illustrating a screen type.

For example, a black screen shown in FIG. 16A may be displayed on the display unit 151 in the first mode.

Figure 18:
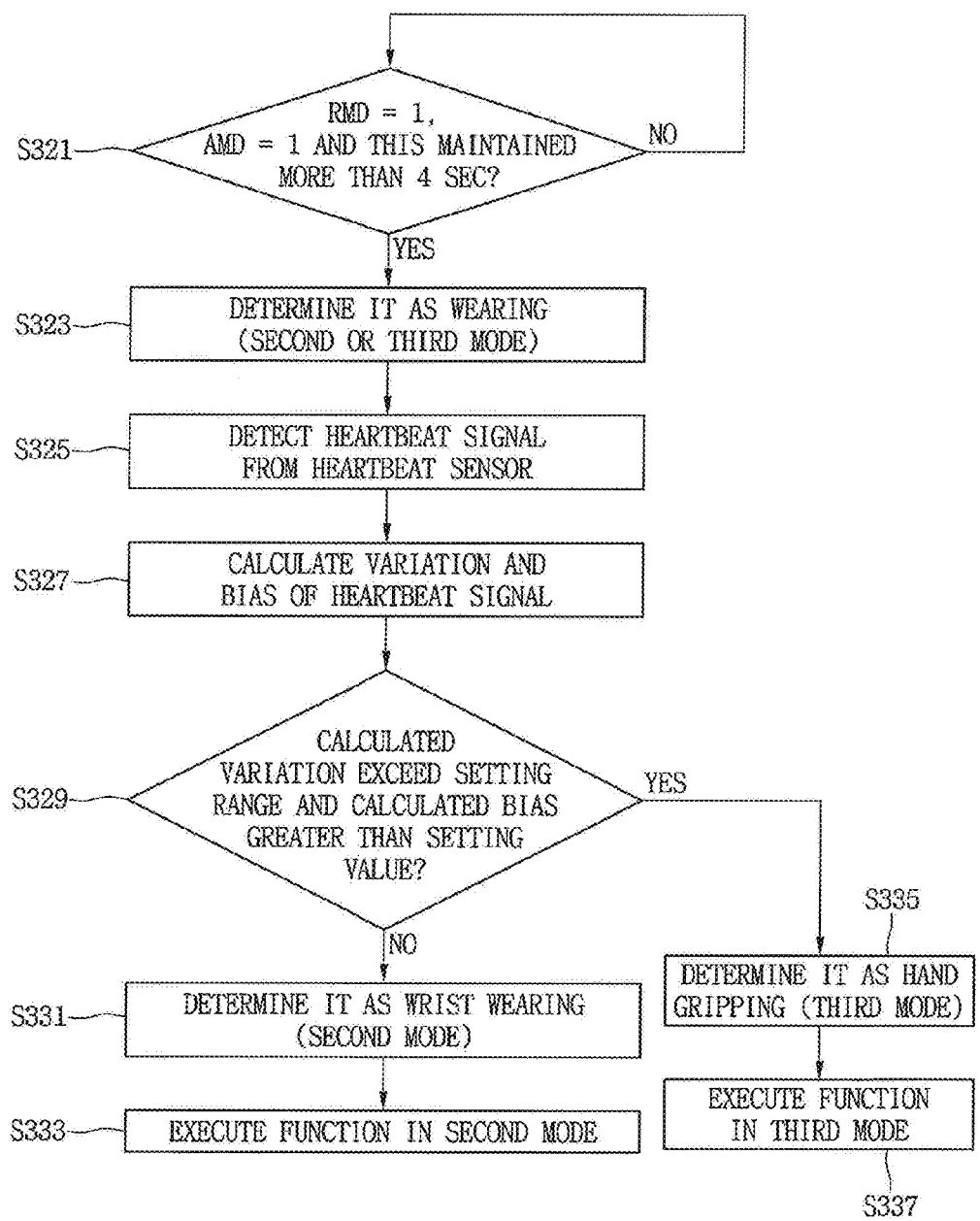
FIG. 18 is a flowchart illustrating a method of detecting a wearing state of the watch type device of FIG. 15 according to an embodiment of the present invention.

FIG. 18 is a flowchart illustrating a method of detecting a wearing state of the watch type device of FIG. 15 according to an embodiment of the present invention.

FIG. 18 is a view embodying operations S305 to S311 of FIG. 15.

Referring to FIG. 18, the control unit 180 of the watch type device 100 checks whether the RMD signal outputted from the acceleration sensor 143 is "1" and the AMD signal is "1".

As mentioned above, when the RMD signal is "1", since the AMD signal is always "1", the control unit 180 of the watch type device 100 may not be necessary to check whether the AMD signal is "0" or "1" and may only check whether the RMD signal is "1".

Then, the control unit 180 of the watch type device 100 checks whether the RMD signal of "1" and the AMD signal of "1" are maintained for more than 4 sec in operation S321. Herein, 4 sec is one exemplary threshold value for convenience of description and such a threshold value may vary according to a manufacturer or a user.

When the RMD signal of "1" and the AMD signal of "1" are maintained for more than 4 sec, the control unit 180 of the watch type device 100 determines it as a wearing state (for example, a second or third mode) in operation S323.

Herein, the second mode may mean a state where the watch type device 100 is worn on a user's wrist and the third mode may mean a state where the watch type device 100 is gripped by a user's hand.

As mentioned above, only a wearing state and a not-wearing state may be determined by the RMD signal and the AMD signal outputted from the acceleration sensor 143.

Accordingly, in order to distinguish wrist wearing from hand gripping during wearing, the heartbeat sensor 114 may be used.

That is, the control unit 180 of the watch type device 100 performs a control on the heartbeat sensor 144 in order to generate a touch interrupt signal from the heartbeat sensor 144 in operation S325.

The heartbeat sensor 144 may prevent a crosstalk phenomenon as shown in FIGS. 6 to 13 in order to improve reliability.

The control unit 180 of the watch type device 100 calculates a signal variation and a bias from the generated touch interrupt signal in operation S327.

The signal variation may represent a waveform variable width of a touch interrupt signal and the bias may represent an average value of touch interrupt signals but the present invention is not limited thereto.

The control unit 180 of the watch type device 100 checks whether the calculated signal variation exceeds a predetermined setting range and the calculated bias is greater than a predetermined setting value in operation S329.

Herein, the predetermined setting range and the setting value may respectively correspond to the signal variation and the bias of the first touch interrupt signal PPG1 shown in FIG. 14.

When the calculated signal variation exceeds the predetermined setting range and the calculated bias is greater than the predetermined setting value, that is, they correspond to the second touch interrupt signal PPG2 shown in FIG. 14, the control unit 180 of the watch type device 100 determines it as hand gripping (that is, the third mode) in operation S335 and executes a function in the third mode in operation S337.

For example, the black screen shown in FIG. 16A or an ambient screen may be displayed on the display unit 151 in the third mode. The ambient screen may have a lower brightness than the standby screen in order to reduce power consumption.

When the calculated signal variation is within the predetermined setting range and the calculated bias is the predetermined setting value, the control unit 180 of the watch type device 100 determines it as wrist wearing (that is, the second mode) in operation S331 and executes a function in the second mode in operation S333.

For example, in the second mode, the analog watch screen (see FIG. 16B), the digital watch screen (see FIG. 16C), or a standby screen such as a home screen may be displayed on the display unit 151.

As another example, a signal variation and a bias of the first touch interrupt signal PPG1 shown in FIG. 14 are stored as first setting information and a signal variation and a bias of the second touch interrupt signal PPG2 shown in FIG. 14 are stored as second setting information. In such a case, it is checked that to which one of the first setting information and the second setting information the signal variation and the bias calculated in operation S327 correspond. If they correspond to the first setting information, it is determined as wrist wearing (for example, the second mode) and if they correspond to the second setting information, it is determined as hand gripping (for example, the third mode).

Moreover, a green light emitting device used as the light emitting unit 225 may be provided to the heartbeat sensor 144. As the heartbeat sensor 144 always operates and thus the green light emitting device flashes, this causes disruption to users or other people and a waste of power occurs.

Accordingly, it is desirable that the heartbeat sensor 144 operates only when it contacts a user's wrist or hand.

A method of reducing power consumption without disturbing users or other people by operating the heartbeat sensor 144 in a specified situation is described with reference to FIG. 19.

Figure 19:
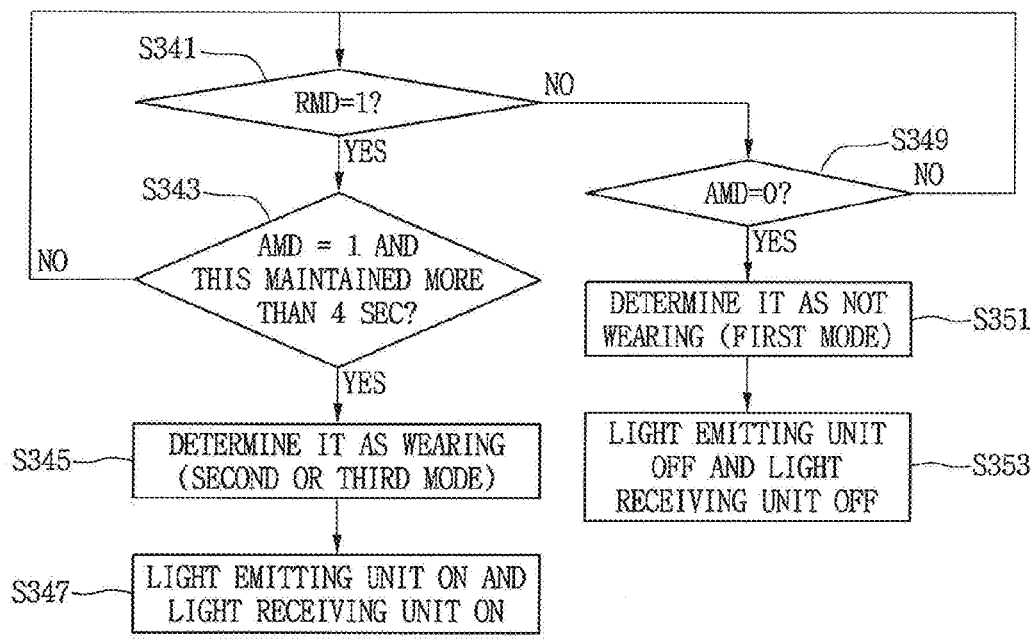
FIG. 19 is a flowchart illustrating a method of operating a heartbeat sensor depending on whether a watch type device is worn according to an embodiment of the present invention.

FIG. 19 is a flowchart illustrating a method of operating the heartbeat sensor 144 depending on whether a watch type device is worn according to an embodiment of the present invention.

Referring to FIG. 19, the control unit 180 of the watch type device 100 checks whether the RMD signal outputted from the acceleration sensor 143 is "1" in operation S341.

If the RMD signal is not "1", that is, the RMD signal is "0", the control unit 180 of the watch type device 100 checks whether the AMD signal is "0" in operation S349.

If the AMD signal is "0", the control unit 180 of the watch type device 100 determines it as not-wearing (that is, the first mode) in operation S351 and turns off both the light emitting unit 225 and the light receiving unit 227 of the heartbeat sensor 144 in operation S353. Accordingly, since power is not applied to both the light emitting unit 225 and the light receiving unit 227 of the heartbeat sensor 144, green light is not generated from the light emitting unit 225 and the light receiving unit 227 may not receive light.

When the AMD signal is "1", the control unit 180 of the watch type device 100 checks whether the AMD signal of "1" is maintained for more than 4 sec in operation S343. Herein, 4 sec is one exemplary threshold value for convenience of description and such a threshold value may vary according to a manufacturer or a user.

If the AMD signal of "1" is maintained for more than 4 sec, the control unit 180 of the watch type device 100 determines it as wearing (that is, the second or third mode) in operation S345 and activates the heartbeat sensor 144 to turn on both the light emitting unit 225 and the light receiving unit 227 of the heartbeat sensor 144 in operation S347. Accordingly, since power is applied to both the light emitting unit 225 and the light receiving unit 227 of the heartbeat sensor 144, green light is generated from the light emitting unit 225 and the light receiving unit 227 receives light so that when a user's hand or wrist contacts the heartbeat sensor 144, a touch interrupt signal may be generated from the heartbeat sensor 144.

Accordingly, in a not-wearing state, the heartbeat sensor 144 does not operate so that it is prevented that light is generated unnecessarily to disturb users or surrounding users and power is wasted.

A function that is currently executed in the second mode (or wrist wearing) or the third mode (or hand gripping) may change into another function execution by a gesture of the watch type device 100, for example, a tilt gesture. The tilt gesture may be a rotation movement clockwise or counterclockwise or may be a horizontal movement in a horizontal direction or a vertical direction.

Figure 20A:
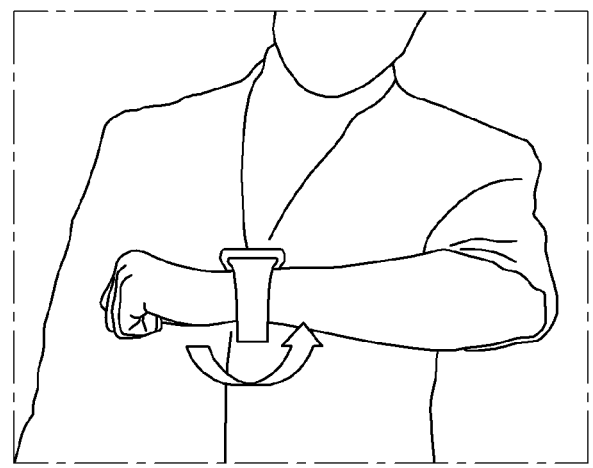
FIGS. 20(a) and 20(b) are views illustrating a tilt when a watch type device is worn on a wrist and gripped by a hand.

For example, when the watch type device 100 is worn on a user's wrist, the analog watch screen (see FIG. 16B) may be displayed. In such a case, as shown in FIG. 20A, when a tilt gesture for the watch type device 100 is inputted, an analog watch screen is changed into a home screen including a plurality of icons and displayed.

Figure 20B:
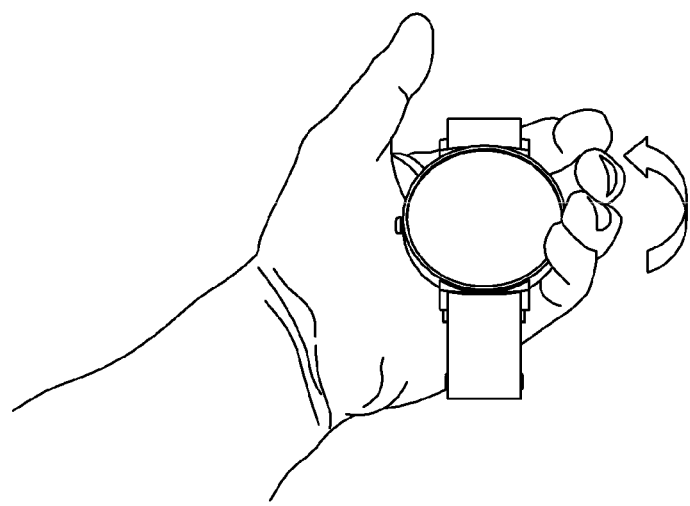

For example, when the watch type device 100 is gripped by a user's hand, the black screen (see FIG. 16A) may be displayed. In such a case, as shown in FIG. 20B, when a tilt gesture for the watch type device 100 is inputted, the current screen may be changed into a standby screen such as the analog watch screen (see FIG. 16B), the digital watch screen (see FIG. 16C), or a home screen including a plurality of icons and displayed.

Each time a tilt gesture is inputted, the standby screen may be changed into a predetermined function. For example, when a first tilt gesture is inputted, the most recently received phone number is displayed and when a second tilt gesture is inputted, a call signal is transmitted to the displayed phone number so that it is possible to make a call with the other party of the phone number.

FIG. 21 is a flowchart illustrating a lock releasing method depending on whether a watch type device is worn according to an embodiment of the present invention.

Referring to FIG. 21, the control unit 180 of the watch type device 100 checks whether the watch type device 100 is worn on a wrist in operation S361.

As mentioned above, when the RMD signal outputted from the acceleration sensor 143 is "1", it is determined that the watch type device 100 is worn and in more detail, the heartbeat sensor 144 may operate in order to determine whether the watch type device 100 is gripped by a hand or worn on a wrist. By comparing a touch interrupt signal generated from the heartbeat sensor 144 with predetermined setting information, it is determined whether the watch type device 100 is worn on a wrist.

When it is determined as wrist wearing, the control unit 180 of the watch type device 100 checks a lock state in operation S363.

When the watch type device 100 is not lock-released at least once after it is worn on a wrist, the control unit 180 of the watch type device 100 may maintain a lock state. In such a case, the control unit 180 of the watch type device 100 executes a lock state mode to display a lock screen on the display unit 151.

When a lock release command is inputted from a user, the watch type device 100 executes lock release to display a standby screen on the display unit 151 in operation S365. The standby screen may include an analog watch screen, a digital watch screen, or a home screen including a plurality of icons.

As one example, when knock code inputted on a lock screen corresponds to predetermined knock code, a lock state may change into a lock release state.

As another example, a touch interrupt signal of the heartbeat sensor 144, which is measured from a user's wrist, corresponds to a predetermined touch interrupt signal, a lock state may change into a lock release state.

If a lock release is failed predetermined times, a lock screen may be no longer displayed and an input screen for inputting pin code may be displayed. A pin code for lock release is set in advance and when a pin code corresponding to a predetermined pin code is inputted from a user through the input screen, lock may be released.

The control unit 180 of the watch type device 100 checks whether wrist wearing is released in operation S367.

For example, when the AMD signal outputted from the acceleration sensor 143 is "0" or when a touch interrupt signal having a signal variation and a bias is not generated from the heartbeat sensor 144, the control unit 180 of the watch type device 100 may recognize that wrist wearing is released.

When wrist wearing is released, the control unit 180 of the watch type device 100 may change a lock release state into a lock state in operation S369. When wrist wearing is released, every time a screen is turned on, a lock screen may be displayed on the display unit 151. As wrist wearing is released, even if a lock state is released on a lock screen, if a screen is turned on again after turned off, the lock screen may be displayed.

As shown in FIG. 21, a lock release method may vary according to a not-wearing state and a wearing state.

TABLE 2

|  | Wearing | Not-wearing |
| --- | --- | --- |
| Lock state --> release state | Knock code | Knock code |
| Lock release state --> lock state | N/A | Move to ambient mode or sleep mode |

As shown in Table 2, a lock state may change into a lock release state by using a knock code during both wearing and not-wearing.

If lock is released once while wearing, even when a standby screen is changed into a black screen or an ambient screen with less power consumption, it does not change into a lock state after one time lock release.

Figure 16B:
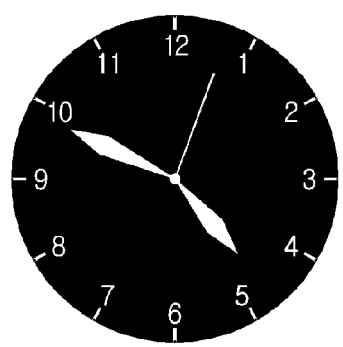
Figure 16C:

For example, a knock code command is inputted on an ambient screen in a lock state during wearing, a lock state is changed into a lock release state and lock is released. As shown in FIG. 16B, an ambient screen may be changed into a standby screen such as a watch screen and is displayed. Since the brightness of a standby screen is higher than that of an ambient screen, power consumption in the standby screen is greater than that in the ambient screen.

As shown in FIG. 22A, after a predetermined time elapses, if no gesture is inputted to a standby screen that is lock-released by using a knock code, as shown in FIG. 22B, a standby screen for reducing power consumption may be changed into an ambient screen. At this point, the ambient screen may be in a lock release state instead of a lock state. In such a case, when a double tap for the ambient screen is inputted, as shown in FIG. 16B, the ambient screen is immediately changed into a standby screen and displayed. In such a manner, a function that lock is released according to an input of a double tap gesture is referred to as a knock on function.

On the other hand, even when lock is released once during not-wearing, if a standby screen is changed into a black screen or an ambient screen, it is changed into a lock state so that lock release may be performed by using a knock code again.

On the other hand, a detection amount of a touch interrupt signal of the heartbeat sensor 144 varies according to a user's color skin.

Figure 23:
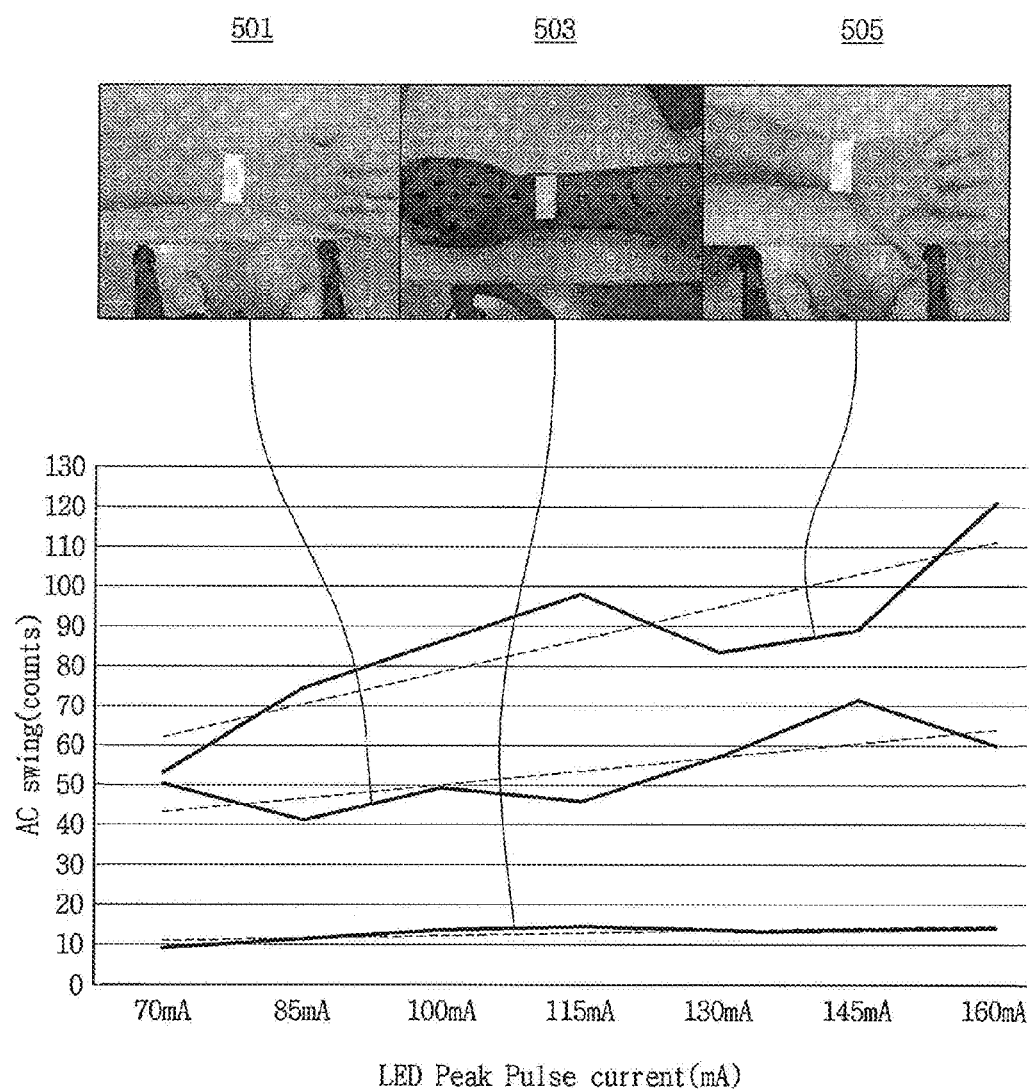
FIG. 23 is a view illustrating the detection amount of a touch interrupt signal according to race.

As shown in FIG. 23, in comparison to the white people 505 or the yellow people 501, it shows that a detection amount of a touch interrupt signal of the black people 503 is significantly low. This is because a significant amount of light from a light emitting device of the heartbeat sensor 144 is absorbed by the skin of the black people 503.

In such a case, on the basis of the same threshold value, in the case of the white people 505, a detection amount of a touch interrupt signal exceeds a threshold value and this is determined as wearing but in the case of the black people 503, a detection amount of a touch interrupt signal is less than a threshold value and this is determined as not-wearing. As a result, heartbeat measurement errors may occur.

A method of accurately measuring a touch interrupt signal regardless of a user's skin color is described.

Figure 24:
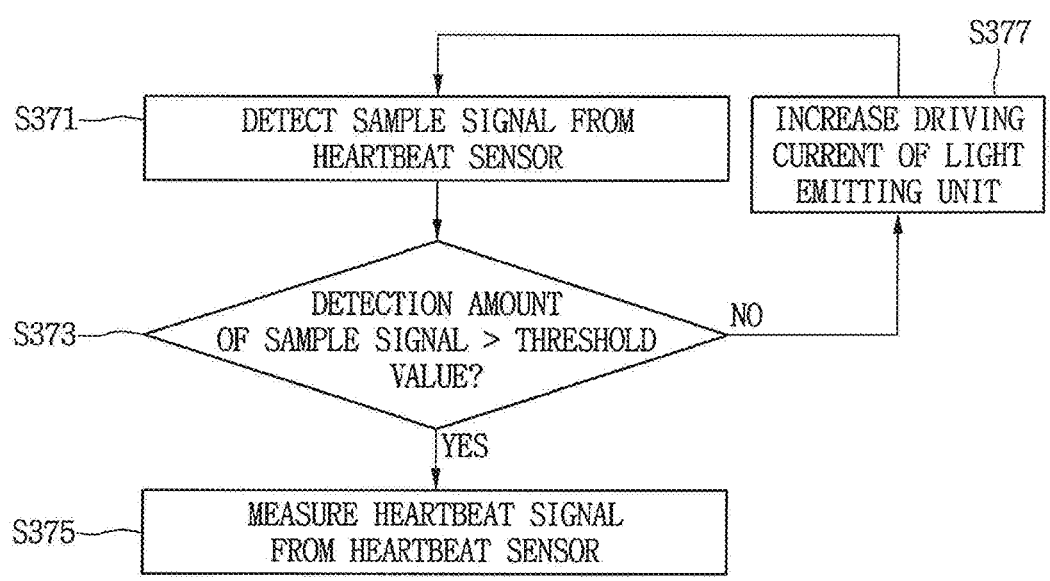
FIG. 24 is a flowchart illustrating a heartbeat measurement method according to a skin in a watch type device according to an embodiment of the present invention.

FIG. 24 is a flowchart illustrating a heartbeat measurement method according to a skin in a watch type device according to an embodiment of the present invention.

Referring to FIG. 24, the control unit 180 of the watch type device 100 performs a control on the heartbeat sensor 144 in order to detect a sample signal from the heartbeat sensor 144 in operation S371. The sample signal may be a plurality of pulse lights that are periodically emitted from the light emitting unit 225 of the heartbeat sensor 144. For example, first to third pulse lights are generated periodically from the light emitting unit 225 and are reflected by a user's skin to be detected as first to third sample signals by the light receiving unit 227.

The control unit 180 of the watch type device 100 calculates a detection amount of a sample signal and checks whether the detection amount is greater than a threshold value in operation S373. The threshold value may be set by a user or a manufacturer.

If the detection amount of a sample signal is greater than the threshold value, the control unit 180 of the watch type device 100 recognizes that there is no error in a detection capability of the heartbeat sensor 144 and thus performs a control on the heartbeat sensor 144 to measure a touch interrupt signal in operation S375.

If the detection amount is less than the threshold value, the control unit 180 of the watch type device 100 performs a control on the heartbeat sensor 144 to increase a driving current of the light emitting unit 225 included in the heartbeat sensor 144 in operation S377. That is, the control unit 180 of the watch type device 100 increases a driving current of the light emitting unit 225 by increasing the power applied to the light emitting unit 225 included in the heartbeat sensor 144. Accordingly, the amount of light generated from the light emitting unit 225 may be increased. The increased amount of light may be reflected by a user's skin and detected as a sample signal by the light receiving unit 227. If the detection amount of a sample signal is less than a threshold value, the method proceeds to operation S377 so that a driving current of the light emitting unit 225 may be increased. Such an operation may be repeated until the detection amount of a sample signal becomes greater than a threshold value.

Hereinafter, various user interfaces using the acceleration sensor 143 and the heartbeat sensor 144 are described.

FIG. 25 is a screen view according a detailed setting of wearing detection.

Figure 25A:
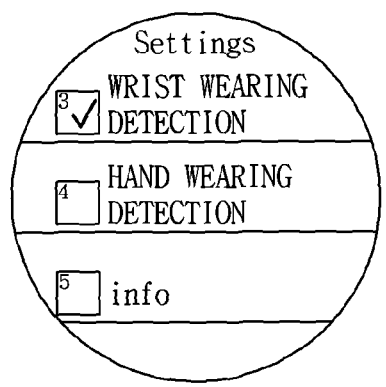
FIGS. 25(a), 25(b), 25(c) and 25(d) are screen views according a detailed setting of wearing detection.

As shown in FIG. 25A, a wrist wearing detection and a hand wearing detection may be displayed on a setting screen and a selection command for one of them may be inputted.

Figure 25B:
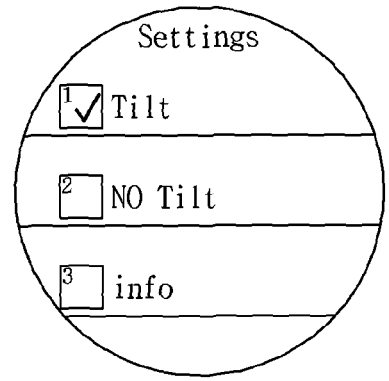

If a selection command for wrist wearing detection is inputted, as shown in FIG. 25B, tilt and no tilt may be displayed and a selection command for one of them may be inputted.

Figure 25C:
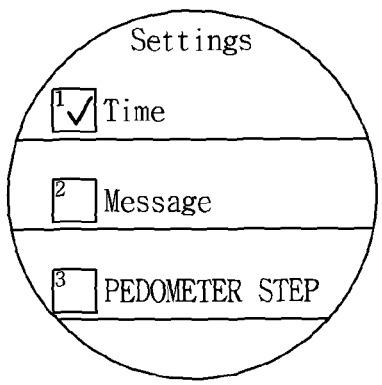

If a selection command for tilt is inputted, as shown in FIG. 25C, time, message, or pedometer may be displayed and a selection command for one of them may be inputted.

Figure 25D:
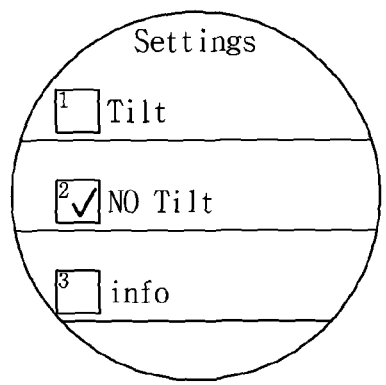

Accordingly, as shown in FIG. 25D, a screen according to tilt or no tilt in the wrist wearing detection or the hand wearing detection may be set.

For example, when the wrist wearing detection, the tilt, and the time are selected and set, as a tilt gesture is inputted in a state of wearing the watch type device 100 on a wrist, a screen having a watch may be displayed on the display unit 151 of the watch type device 100.

When a selection command for no tilt is inputted, a screen according to no tilt in the wrist wearing detection may be set.

In such a case, when wrist wearing is detected, even if no tilt gesture is inputted, a predetermined screen, for example, an analog watch screen, may be displayed on the display unit 151.

FIG. 26 is a screen view illustrating a message checking method in a hand gripping state.

In a not-wearing state, when a screen of the watch type device 100 is turned on, for example, an analog watch screen may be displayed.

When the watch type device 100 is gripped by a hand, an analog watch screen may be displayed.

In such a case, if there is a missed message, a text notification "missed message" may be displayed on the display unit 151.

Figure 26A:
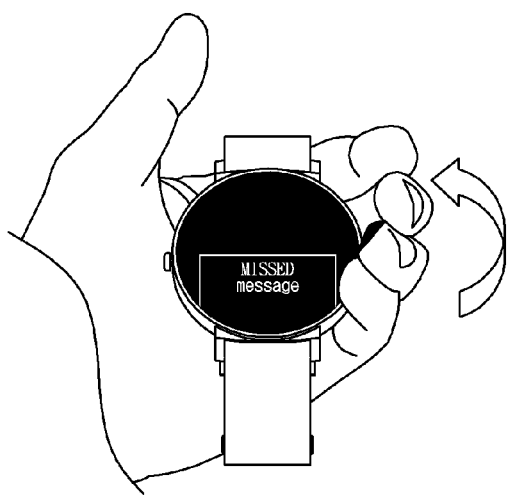
FIGS. 26(a), 26(b) and 26(c) are screen views illustrating a message checking method in a hand gripping state.

In such a case, if a tilt gesture for the watch type device 100 is inputted as shown in FIG. 26a in a state where the watch type device 100 is gripped by a user's hand, source information of a missed message may be displayed. The source information may include numbers, characters, images, or icons representing text message, SNS, e-mail, and so on.

As another example, while the screen of the watch type device 100 is displayed as a black screen in a not-wearing state, if a user grips the watch type device 100, this is recognized so that the screen of the watch type device 100 may be changed from the black screen into an analog screen. At this point, since source information of a missed message in addition to the analog screen may be displayed, a tilt gesture is not required.

Figure 26B:
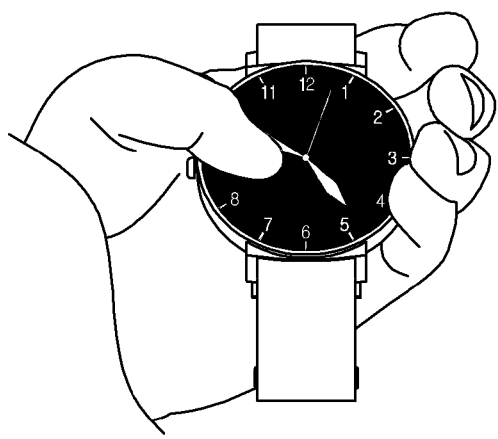
Figure 26C:

As shown in FIG. 26B, when a knock code command is inputted on a screen, as shown in FIG. 26C, detailed content of the source may be displayed.

A knock code refers to a technique for dividing a screen into a plurality of areas and matching each area with a number in order to release a lock state with a number combination corresponding to an area that a user selects.

For example, when three source information is displayed, if a knock code command is inputted, detailed content of first received source information among the three source information is displayed and each time a tilt gesture is inputted, detailed content of the next received source information may be displayed.

As another example, without displaying source information of a missed message by an input of a tilt gesture, detailed information of a missed message may be displayed by an input of a knock code command for a standby screen.

FIG. 27 is a screen view illustrating a message checking method in a wrist wearing state.

It is assumed that the message checking method of FIG. 27 relates a case that lock is released once in a wrist wearing state.

Figure 27A:
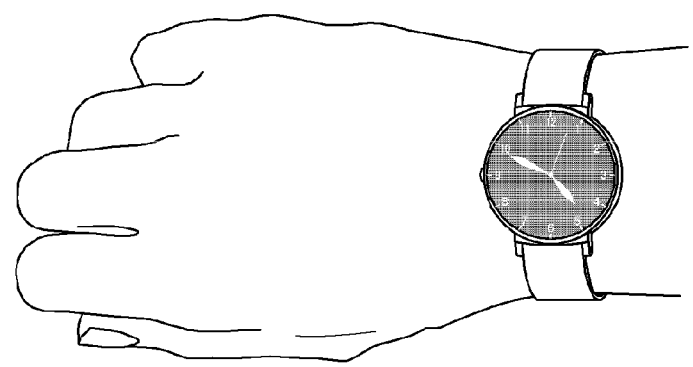
FIGS. 27(a), 27(b), 27(c) and 27(d) are screen views illustrating a message checking method in a wrist wearing state.

As shown in FIG. 27A, if there is no specific gesture for a predetermined time after lock is released once in a state where the watch type device 100 is worn on a wrist, a standby screen may be changed into an ambient screen and displayed. Since the background of an ambient screen has a lower grayscale brightness than the background of a standby screen, power consumption may be reduced further in the ambient screen than the standby screen. Both the ambient screen and the standby screen may include an analog watch.

Figure 27B:
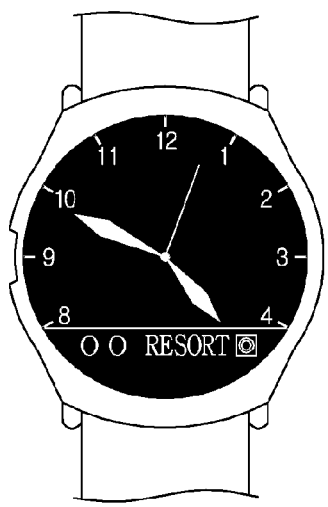

As shown in FIG. 27b, when a tilt gesture for the watch type device 100 is inputted, an ambient screen is changed into a standby screen and displayed. Furthermore, specific information may be displayed on the changed standby screen. The specific information may be provided from a specific content provider but the present invention is not limited thereto. For example, the specific information may include travel information and shopping mall information.

Figure 27C:
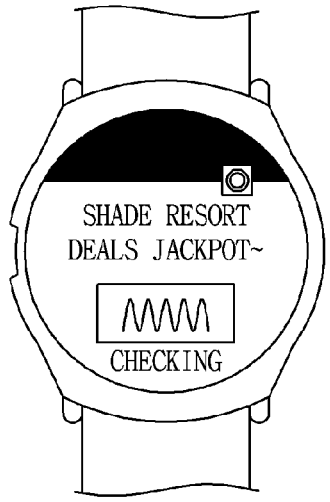

As shown in FIG. 27C, as the heartbeat sensor 144 operates, a heartbeat signal may be detected and user authentication may be performed by the heartbeat signal. In such a case, entire content of specific information may be displayed on a screen.

Figure 27D:

When user authentication using a heartbeat signal is successful, as shown in FIG. 27D, detailed content of specific information may be displayed.

FIG. 28 is a screen view illustrating a setting screen displaying method in a wearing state.

In a not-wearing state, a black screen may be displayed on the display unit 151 (see FIG. 16A). The not-wearing state may be a state where the watch type device 100 is disposed in a specific place.

When a not-wearing state becomes a wearing state, a black screen may be changed into a standby screen and displayed. In such a case, since power is not supplied to the display unit 151, power consumption does not occur.

Although a standby screen including hands, dials, and a background is shown in the drawing, the present invention is not limited thereto.

In order for a user to set a specific function, when tap or flick touch is inputted for a specific area of a standby screen, for example, hands, dials, and a background, as shown in FIG. 28, the standby screen may be changed into a setting screen and displayed. For example, flick touch may be inputted from the 12 o'clock dial to the center area of the standby screen but the present invention is not limited thereto.

A specific function may be set by using heat, connectivity, and security included on the setting screen.

FIG. 29 is a screen view illustrating a method of setting heat displayed on a setting screen in a wearing state.

In a wearing state, a standby screen may be displayed.

In such a case, when tap or flick touch for a specific area of a standby screen is inputted from a user, as shown in FIG. 29A, a setting screen including heat, security, and connectivity may be displayed. For example, flick touch may be inputted from the 12 o'clock dial to the center area of the standby screen but the present invention is not limited thereto.

When a selection command for heat is inputted from a user, as shown in FIG. 29B, a heat user interface (heat UI) and a heat control may be displayed.

The heat UI may relates to a method of controlling heat by using a UI and the heat control may relate to a method of controlling heat systematically.

Low temperature burns have become an issue recently. Low temperature burns refer to burns occurring when a user is exposed to more than a warm temperature for a long time instead of a high temperature causing a pain to a user. Especially, in comparison to high temperature burns, low temperature burns cause burns further deep inside a skin and are more dangerous than high temperature burns.

Figure 30:
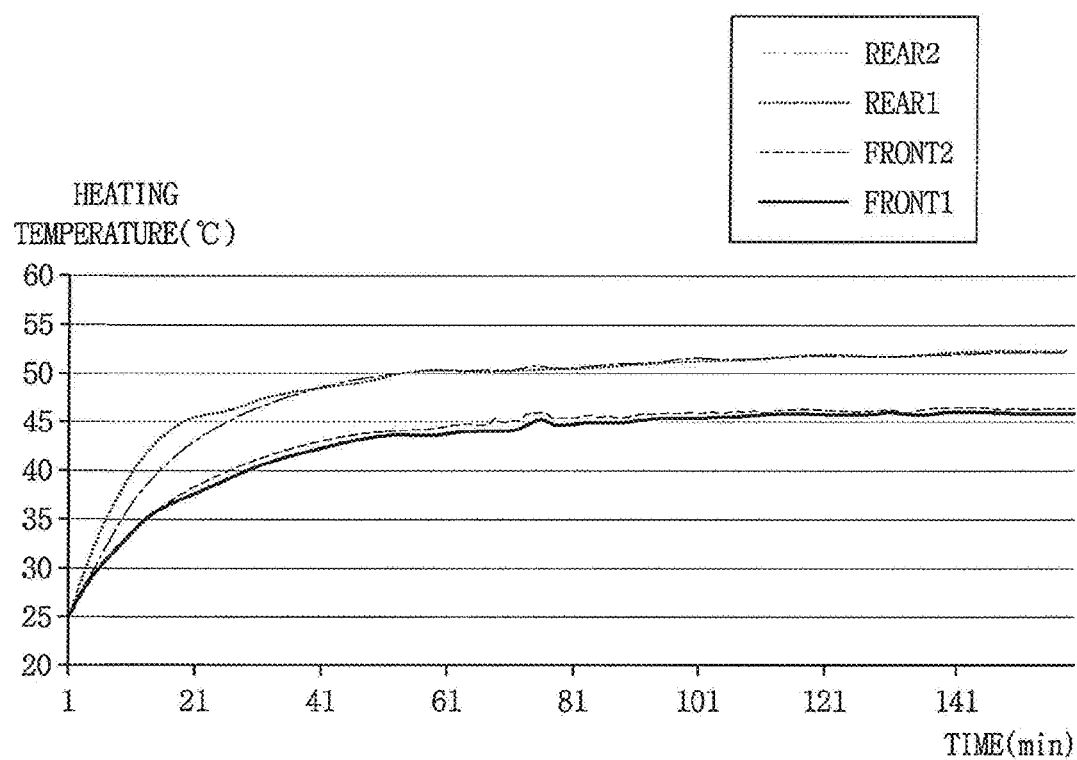
FIGS. 30(a) and 30(b) are graphs obtained by measuring a heating temperature at each of the front and rear of a watch type device.

As shown in FIG. 30, the heating temperature of the rear of the watch type device 100 is higher than that of the front. The heating temperature of the rear is drastically increased as the watch type device 100 operates, and then exceeds 40° C. after 30 min.

Accordingly, if a user is exposed for a long time at a heating temperature of more than 40° C., a user is most likely to be damaged by low temperature burns.

FIG. 31 is a screen view illustrating a pop-up message notifying method according to heating temperature.

When the watch type device 100 is in a not-wearing state and its heating temperature is greater than a predetermined heating temperature, for example, 40° C., one of a charging stop message, a power off alarm message, and a power off message may be displayed.

Figure 31A:
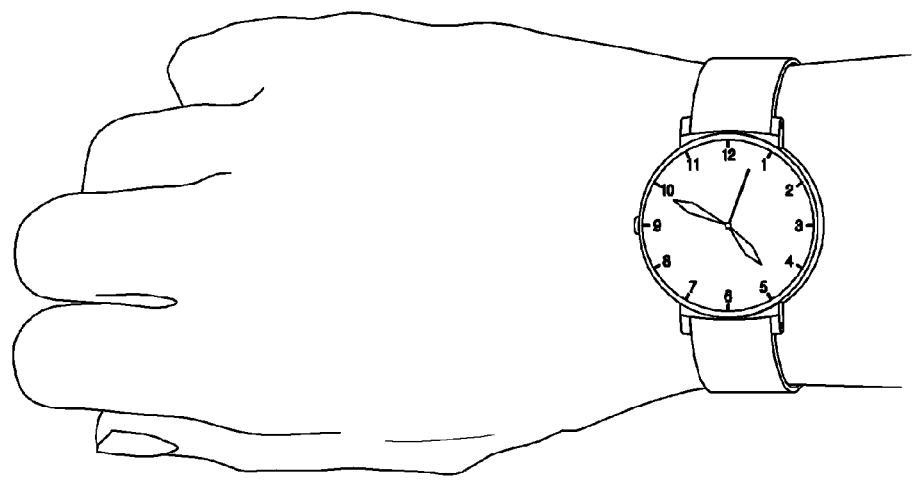
FIG. 31 is a screen view illustrating a pop-up message notifying method according to heating temperature.
Figure 31B:
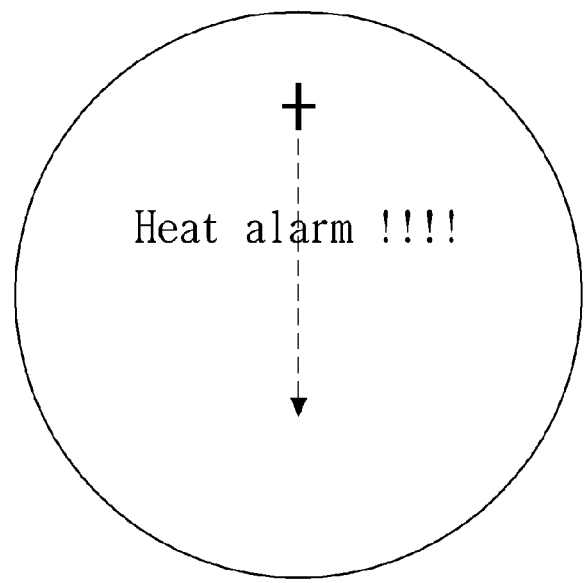

On the other hand, as shown in FIG. 31A, when the watch type device 100 is in a wearing state and its heating temperature is greater than a predetermined heating temperature, for example, 40° C., as shown in FIG. 31B, a heat alarm message may be displayed.

If the watch type device 100 is in a wearing state continuously, a guide message "low temperature burns may occur if keeping an existing state continuously" may be displayed.

As another example, when a drag touch to a specific direction is inputted for the heat alarm message shown in FIG. 31B, a guide message may be displayed.

When the watch type device 100 is in a wearing state continuously, one of a charging stop message, a power off alarm message, and a power off message may be displayed.

Moreover, when a selection command for heat UI is inputted (see FIG. 29B), a background color and a circle indicator may be displayed.

Figure 32A:
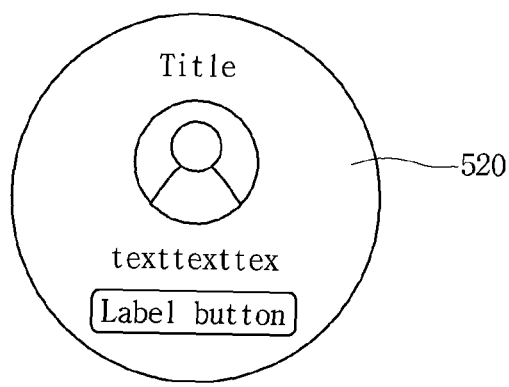
FIGS. 32(a), 32(b) and 32(c) are screen views illustrating a method of changing the background color of a screen according to a heating temperature.

If a selection command for a background color is inputted in order to set the background color, as shown in FIG. 32, a different background color may be displayed according to a heating temperature.

For example, as shown in FIG. 31A, when a heating temperature of the watch type device 100 is less than a predetermined heating temperature, for example, 35° C., the background of a screen displayed on the display unit 151 may have white color or black color 520.

Figure 32B:
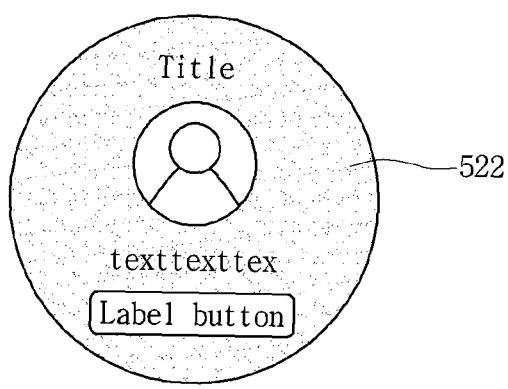

When a heating temperature of the watch type device 100 is increased and is greater than 35° C. and less than 45° C., as shown in FIG. 32B, the background of the screen may be changed from white color or black color 520 to yellow color 522 and displayed.

Figure 32C:
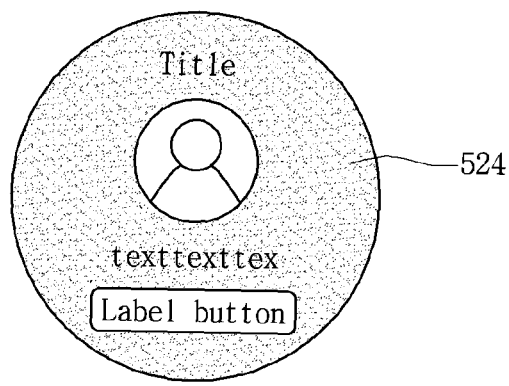

When a heating temperature of the watch type device 100 is increased and is greater than 45° C., as shown in FIG. 32C, the background of the screen may be changed from yellow color 522 to red color 524 and displayed.

When a screen having a background of red 524 is displayed, it may give a warning to a user by sound or vibration.

Herein, 35° C. is a first setting heating temperature and 45° C. is a second setting heating temperature. 35° C. and 45° C. are just examples and such a setting heating temperature may vary according to a user or a manufacturer.

If a selection command for a circle indicator is inputted in order to set the circle indicator (see FIG. 29), as shown in FIG. 33, a different background color may be displayed according to a heating temperature.

Figure 33A:
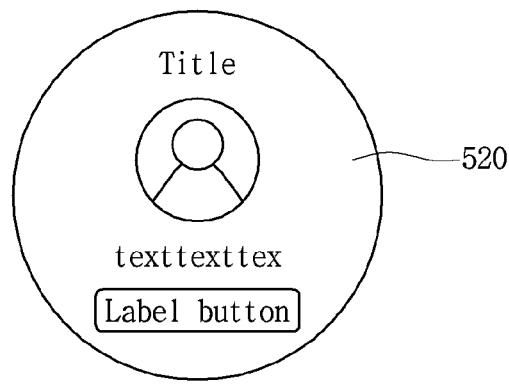
FIGS. 33(a), 33(b) and 33(c) are screen views illustrating a method of changing the color of an indicator displayed on a screen according to a heating temperature.

For example, as shown in FIG. 33A, when a heating temperature of the watch type device 100 is less than a predetermined heating temperature, for example, 35° C., no indicator is displayed at the frame of a screen displayed on the display unit 151.

Figure 33B:
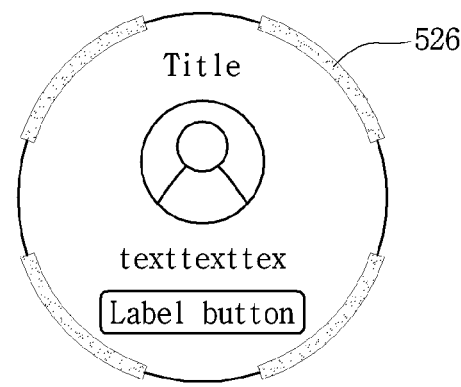

When a heating temperature of the watch type device 100 is increased and is greater than 35° C. and less than 45° C., as shown in FIG. 33B, at least one indicator 526, which is spaced apart from each other along the frame of a screen and has yellow color, may be displayed. At least one indicator 526 may have yellow color.

Figure 33C:
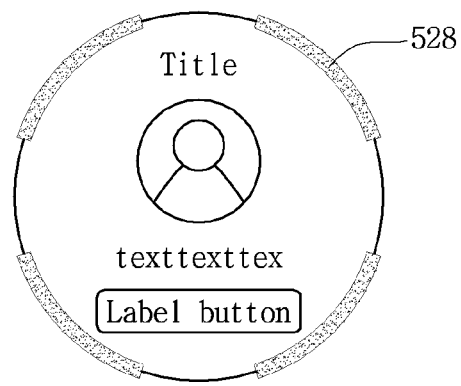

When a heating temperature of the watch type device 100 is increased and is greater than 45° C., as shown in FIG. 33C, at least one indicator 528, which is spaced apart from each other along the frame of a screen and has red color, may be displayed.

That is, while an indicator is not displayed on a screen, if a heating temperature of the watch type device 100 is greater than 35° C., an indicator 526 with yellow color may be displayed and if a heating temperature of the watch type device 100 is greater than 45° C., an indicator 528 of which color is changed from yellow to red may be displayed.

When a screen having a red indicator 528 is displayed, it may give a warning to a user by sound or vibration.

FIG. 34 is a screen view illustrating a method of lowering a heating temperature according to a heat control set in FIG. 29.

Figure 34A:
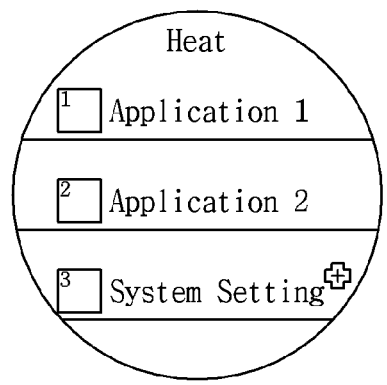
FIGS. 34(a) and 34(b) are screen views illustrating a method of lowering a heating temperature according to a heat control set in FIG. 29.
Figure 34B:
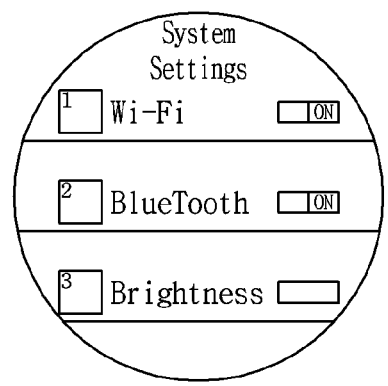

When a screen having the red indicator 528 by a heating temperature of more than 45° C. is displayed, as shown in FIGS. 34A and 34B, a setting for lowering such a heating temperature may be required.

For example, when a drag touch is inputted from the red indicator 528 to the center area of a screen (see FIG. 33C), as shown in FIG. 34A, a plurality of applications Application 1 and Application 2 and a system setting may be displayed.

If a selection command for system setting is inputted, as shown in FIG. 34B, Wi-Fi, Bluetooth, and Brightness may be displayed. According to an additional input of a selection command of a user, Wi-Fi and Bluetooth may be set to be activated (or ON) or deactivated (or OFF) or a level of brightness may be changed into a low level.

Moreover, when a selection command for a specific application (for example, Application 1) is inputted, a window for checking the deletion of the specific application may be displayed. When a selection command for the deletion is inputted, the specific application may be deleted.

Figure 35:
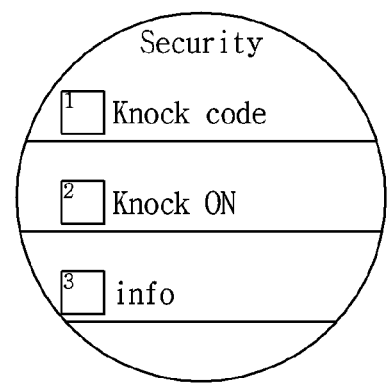
FIG. 35 is a screen view illustrating a method of setting security displayed on a setting screen in a wearing state.

FIG. 35 is a screen view illustrating a method of setting security displayed on a setting screen in a wearing state.

When a selection command for security is inputted from a user (see FIG. 28), as shown in FIG. 35, Knock code and Knock ON may be displayed.

As mentioned above, Knock code refers to a technique for dividing a screen into a plurality of areas and matching each area with a number in order to release a lock state with a number combination corresponding to an area that a user selects.

Knock ON refers to a gesture of knocking a screen twice.

Figure 36:
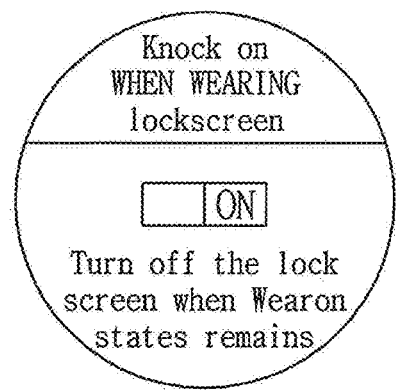
FIG. 36 is a screen view illustrating a subsequent setting method when Knock On is selected in FIG. 35.

FIG. 36 is a screen view illustrating a subsequent setting method when Knock On is selected in FIG. 35.

When a selection command for Knock ON is inputted (see FIG. 35), as shown in FIG. 36, a window for checking whether to turn off a lock screen when a wearing state is maintained may be displayed.

If it is set to turn off a lock screen, as the watch type device 100 is worn and lock is released once, after that, a predetermined specific screen may be displayed immediately without an additional lock release process. The specific screen may be an ambient screen or a standby screen.

This is described in more detail with reference to FIG. 37.

FIG. 37 is a flowchart illustrating a screen activating method and a lock releasing method according to wearing.

Referring to FIG. 37, the control unit 180 of the watch type device 100 checks whether the watch type device 100 is worn in operation S381. Herein, the wearing refers to wearing the watch type device 100 by a wrist instead of gripping the watch type device 100 by a hand.

If it is determined that the watch type device 100 is in a not-wearing state, the control unit 180 of the watch type device 100 displays a black screen on the display unit 151 in operation S382.

In relation to the black screen, power is not applied to the display unit 151 and thus power is not consumed.

When a Knock ON function is executed on a black screen in order to switch to an ambient screen or a standby screen, that is, double tap for the black screen is inputted, a lock screen may be displayed on a watch screen in operation S383. A lock pattern 530 may be displayed on the lock screen.

Once a gesture for lock release is inputted from a user, if the inputted gesture corresponds to a predetermined pattern, lock is released so that an ambient screen or a standby screen may be displayed.

If it is determined that the watch type device 100 is in a wearing state, the control unit 180 of the watch type device 100 displays a black screen on the display unit 151 in operation S384.

When a Knock ON function is executed on a black screen in order to switch to an ambient screen or a standby screen, that is, double tap for the black screen is inputted, the control unit 180 of the watch type device 100 checks whether there is a lock release event of at least one time previously in a wearing state in operation S385.

If there is a lock release event of at least one time previously in a wearing state on the basis of a check result, without an additional lock release process, a watch screen and a home screen including icons on the watch screen may be displayed to overlap each other in operation S386. At this point, icons of a home screen may be changed from a transparent state into an opaque state.

If a selection command for a home screen is inputted by a user, a watch screen may disappear and only the home screen may be displayed. For example, a selection command for a home screen may be a tilt gesture but the present invention is not limited thereto.

If there is no lock release event of at least one time previously in a wearing state, a lock screen having a lock pattern 530 may be displayed on a watch screen in operation S387.

Once a gesture for lock release is inputted from a user, if the inputted gesture corresponds to a predetermined pattern, lock is released so that an ambient screen or a standby screen may be displayed.

Although not shown in the drawing, a user authentication by a heartbeat signal using the heartbeat sensor 144 may be used.

For example, if lock has been released before, a user authentication by a heartbeat signal may be used instead of double tap. User authentication may take about 3 sec. When double tap is inputted during user authentication, regardless of whether the user authentication is successful, an ambient screen or a standby screen may be displayed immediately.

As another example, if lock is never released before, a lock release using a user authentication by heartbeat signal and a lock pattern may be used. In such a case, the user authentication by heartbeat signal may be performed before double tap is inputted or may be performed together when double tap is inputted but the present invention is not limited thereto.

A method of displaying a standby screen by lock release during not-wearing is described with reference to FIG. 37.

Referring to FIG. 37, when the watch type device 100 is not worn by a user (that is, not-wearing), if a double tap (for example, knock on) for a black screen in operation S382 is inputted, a lock screen having a lock pattern 530 in operation S383 may be displayed.

When a lock release command using lock pattern is inputted, a home screen including a plurality of icons 532 may be displayed as a standby screen. Instead of the home screen, an analog watch screen or a digital watch screen may be displayed.

Accordingly, a black screen where no power is applied by a touch tap input and a lock release may be changed into an activated standby screen.

If a predetermined time elapses, the displayed standby screen may be chanted into a black screen and displayed.

In such a case, in order to change to the standby screen again, a double tap input process in operation S382 and a lock release process in operation S383 need to be performed.

That is, each time a standby screen is changed into a black screen during not-wearing, in order to change the changed black screen into the standby screen, a lock release process needs to be performed each time.

When a user does not have the watch type device 100 in the user's hand during not-wearing, this makes security vulnerable. Therefore, by displaying a standby screen each time through lock release, the security during not-wearing may be enhanced.

Hereinafter, a method of displaying a standby screen by first lock release during wearing is described with reference to FIG. 37.

Referring to FIG. 37, when the watch type device 100 is worn by a user, that is, when it is worn on a wrist or gripped by a hand, a black screen may be displayed on the display unit 151 in operations S381 and S384.

When double tap for a black screen displayed in operation S384 is inputted, a lock screen having a lock pattern in operation S387 may be displayed.

When a lock release command using lock pattern is inputted, an analog watch screen may be displayed as a standby screen. Instead of the analog watch screen, a digital watch screen or a home screen may be displayed.

Although not shown in the drawing, when the watch type device 100 is worn by a user, that is, when it is worn on a wrist or gripped by a hand, instead of the black screen in operation S384, the lock screen in operation S387 may be immediately displayed. Accordingly, a double tap input process for activating the black screen as the standby screen may be omitted.

Although not shown in the drawing, user authentication by a heartbeat signal using the heartbeat sensor 144 may be performed before double tap input or may be performed simultaneously with double tap input. In such a way, as user authentication using the heartbeat sensor 144 is added, the security may be further enhanced.

As above, during a first lock release, a lock may be released by using a lock pattern on a lock screen.

Hereinafter, a method of displaying a standby screen by after first lock release during wearing is described with reference to FIG. 37.

If a predetermined time elapses, an analog watch screen that is lock-released first and displayed is changed into a black screen for reducing power consumption and displayed.

In such a case, when double tap for a black screen is inputted, an analog watch screen may be displayed as a standby screen.

That is, if lock is released at least once during wearing, without a lock releasing process after that, each time double tap is inputted from a user, a black screen may be changed into a standby screen at any time. Accordingly, the trouble of releasing the lock each time a black screen is changed into a standby screen during wearing may be eliminated.

Figure 38:
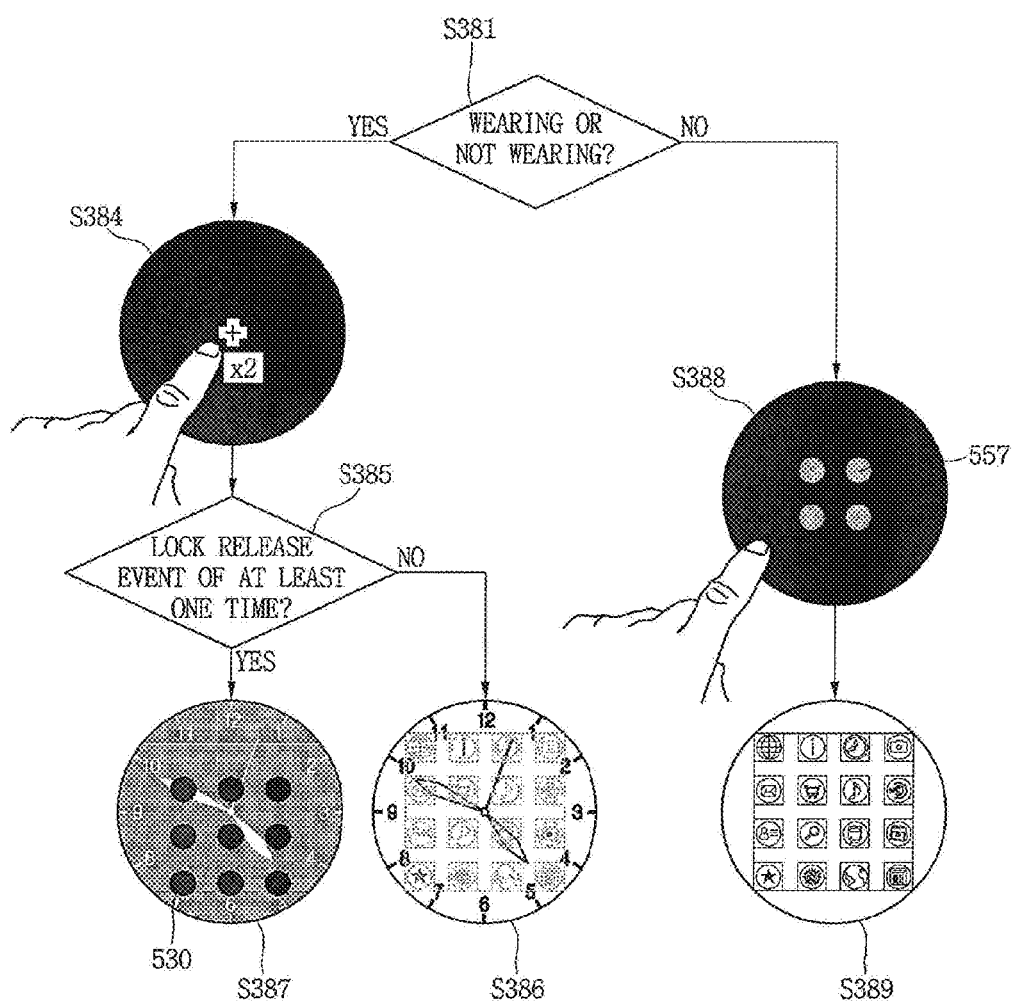
FIG. 38 is another flowchart illustrating a screen activating method and a lock releasing method according to wearing.

FIG. 38 is another flowchart illustrating a screen activating method and a lock releasing method according to wearing.

Referring to FIG. 38, unlike FIG. 37, a method of releasing a lock by using knock code instead of a lock screen in operation S383 is described.

In a not-wearing state, a black screen having a displayed knock code area 557 may be displayed on the display unit 151 in operation S388.

A standby screen such as a home screen may be displayed in operation S389 through lock release by using a plurality of knock code areas 557 that are virtually allocated on the black screen.

Although lock is released using knock code and a standby screen is displayed, after a predetermined time elapses, the standby screen may be changed into a black screen or an ambient screen again and also a lock release state may be changed into a lock state. Accordingly, in order for lock release again, a lock release process using knock code needs to be performed.

It is illustrated that a knock code area is visible to the naked eye but actually, it is not visible to the naked eye. Accordingly, a user may release a lock by touching a black screen in the order that a user presets.

Instead of the home screen, an analog watch screen, a digital watch screen, or another type of a standby screen may be displayed.

FIG. 39 is a screen view illustrating a method of releasing lock by using a heartbeat signal.

Figure 39A:
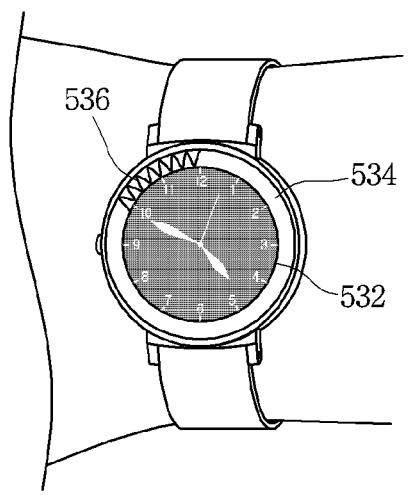
FIGS. 39(a) and 39(b) are screen views illustrating a method of releasing lock by using a heartbeat signal.
Figure 39B:
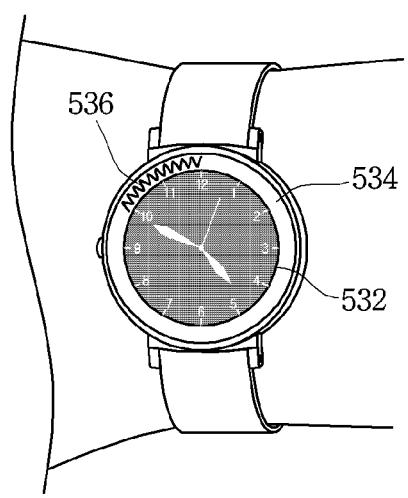

As shown in FIG. 39A, when a black screen 532 is displayed, if a user's hand or wrist contacts the heartbeat sensor 144 of the watch type device 100, a heartbeat signal may be generated from the heartbeat sensor 144.

The generated heartbeat signal 536 may be displayed at the frame of the black screen 532. That is, when recognizing the contact of a user's hand or wrist, the control unit 180 of the watch type device 100 may perform a control to operate the heartbeat sensor 144. In such a way, when recognizing the contact of a user's hand or wrist, the control unit 180 of the watch type device 100 allocates the frame of the black screen 532 as the heartbeat display area 534. The generated heartbeat signal 536 may be displayed on the allocated heartbeat display area 534.

When the generated heartbeat signal 536 is within a predetermined range, the control unit 180 of the watch type device 100 releases a lock, and changes the black screen 532 into a standby screen and displays it.

The predetermined range may vary according to each user. Accordingly, a setting range that a user of the watch type device 100 registers previously may be the unique identifier of the user of the watch type device 100.

If the generated heartbeat signal 536 is out of a predetermined range (see FIG. 39B) or no heartbeat signal is displayed in the heartbeat display area 534 because no heartbeat signal is generated, lock is not released.

Moreover, when a selection command for security is inputted (see FIG. 28), knock code or knock on may be displayed.

When a selection command for knock code is inputted, a knock code gesture may be displayed.

It may be set to activate a knock code gesture by an ON selection command for the knock code gesture.

A method of utilizing a knock code gesture is described with reference to FIG. 40.

FIG. 40 is a screen view illustrating a method of utilizing a knock code gesture.

Figure 40A:
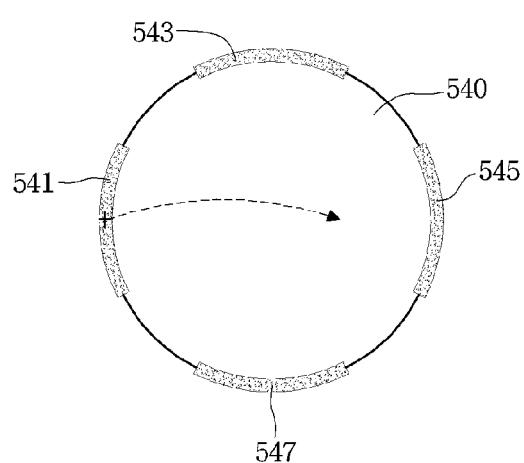
FIGS. 40(a), 40(b), 40(c) and 40(d) are screen views illustrating a method of utilizing a knock code gesture.

As shown in FIG. 40a, a plurality of gesture bars 541, 543, 545, and 547 may be displayed at the frame of the screen 540.

For example, when touch and drag from the first gesture bar 541 toward the center of the screen 540 is inputted from a user, an internet browser application is executed so that a predetermined webpage may be displayed on the display unit 151.

Figure 40B:
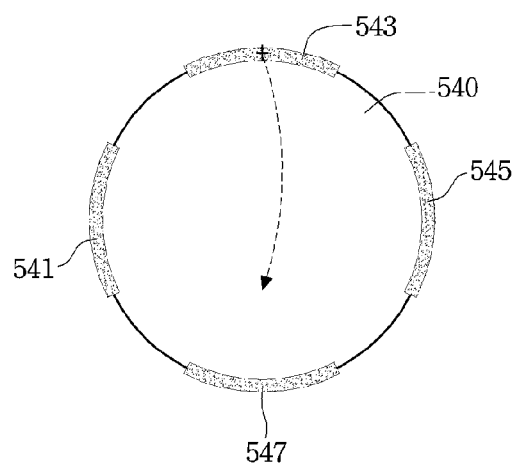

As shown in FIG. 40B, when touch and drag from the second gesture bar 543 toward the center of the screen 540 is inputted from a user, a watch application is executed so that a watch screen may be displayed on the display unit 151.

Figure 40C:
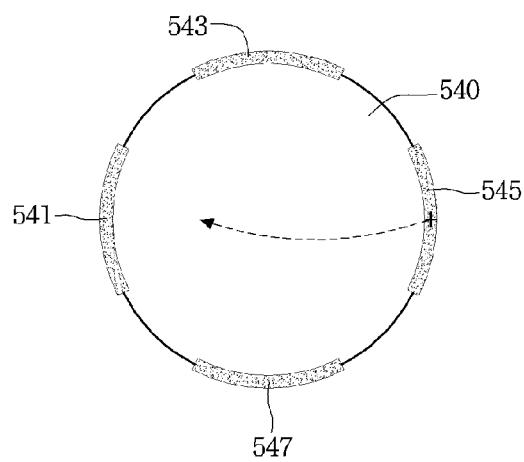
Figure 40D:
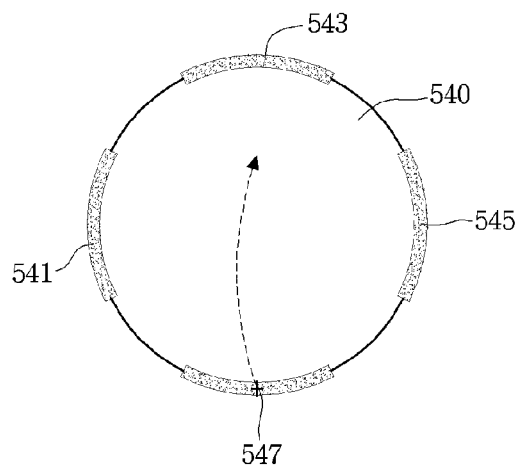

As shown in FIG. 40C, when touch and drag from the third gesture bar 545 toward the center of the screen 540 is inputted from a user, a phone application is executed so that a phone initial screen may be displayed on the display unit 151.

As shown in FIG. 40C, when touch and drag from the fourth gesture bar 547 toward the center of the screen 540 is inputted from a user, a setting application is executed so that a setting initial screen may be displayed on the display unit 151.

FIG. 41 is a screen view illustrating a method of changing dials in a wearing state.

A watch screen of the watch type device 100 may include hands 553 representing hour and minute hands, dials 551 representing time numbers, and a background 555.

Figure 41A:
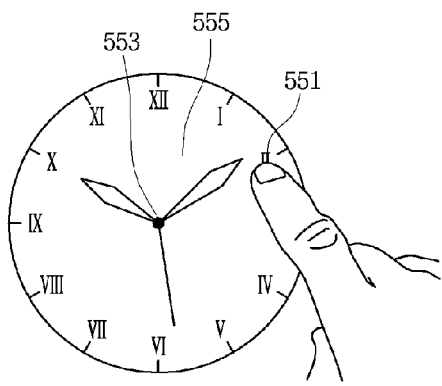
FIGS. 41(a), 41(b), 41(c), 41(d) and 41(e) are screen views illustrating a method of changing dials in a wearing state.
Figure 41B:
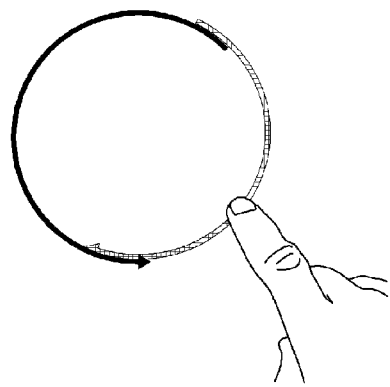
Figure 41C:
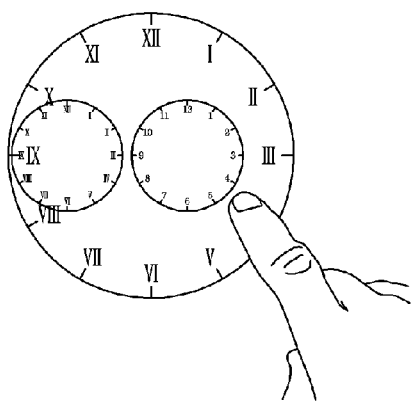

For example, when touch and hold is inputted for a predetermined time, for example, several sec, for a specific dial 551 as shown in FIG. 41A and rotation drag is inputted clockwise or counter-clockwise along an area where the dial 551 is disposed, that is, the frame area of the watch screen as shown in FIG. 41B, the current dial form may be changed into another dial form as shown in FIG. 41C.

Each time rotation drag is inputted clockwise or counter-clockwise, the current dial form may be changed into another dial form. At this point, the changed dial form is not yet set as the dial of a watch screen.

Accordingly, an additional gesture may be inputted in order to set the changed dial form as the dial of a watch screen.

Figure 41D:
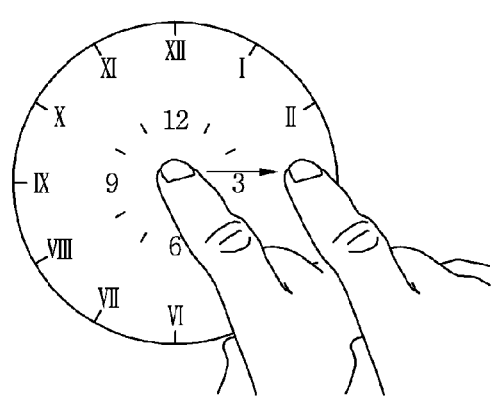
Figure 41E:
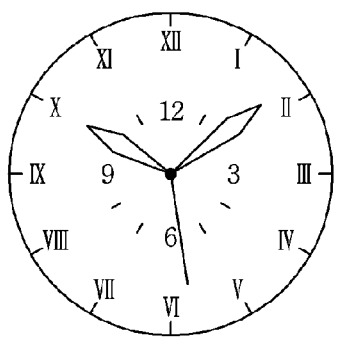

For example, in the case of setting a dial form, after touching an arbitrary point of a dial form shown in FIG. 41C, drag is inputted in one direction shown in FIG. 41D, for example, from the center area of a watch screen to the 3 o'clock direction, as shown in FIG. 41E, the changed dial form is applied to the hands 553 and the background 555 so that a fixed watch screen may be displayed. Accordingly, the dial form of FIG. 41A may be changed into the dial form of FIG. 41E.

Without a drag operation according to one direction shown in FIG. 41D, the changed dial form is applied to the hands 553 and the background 555 immediately by a touch operation on an arbitrary point shown in FIG. 41C so that a fixed watch screen may be displayed as shown in FIG. 41E.

Although not shown in the drawing, the above-described dial changing method is identically applied so that the hands 553 or the background 555 may be changed.

On the other hand, in a wearing state, without an additional lock release process, a simple specific user interface may be executed by a specific gesture.

For example, when double tap for a black screen is inputted, without a lock release process, the black screen may be changed into a standby screen such as a watch screen immediately and displayed.

For example, when rotation drag touch is inputted along one side of the frame 558 of a black screen, without a lock release process, an internet browser application may be immediately displayed, or an internet browser application may be executed so that a predetermined webpage is displayed on the display unit 151.

For example, when rotation drag touch is inputted along the other side of the frame 559 of a black screen, without a lock release process, a setting application may be displayed, or a setting application may be executed so that a predetermined webpage may be displayed on the display unit 151.

Since the watch type device 100 is always present within a user's view in a wearing state, in comparison to a not-wearing state, the security level may be low. Accordingly, in a wearing state, without an additional lock release process, a corresponding user interface may be executed immediately by a specific gesture.

Figure 42:
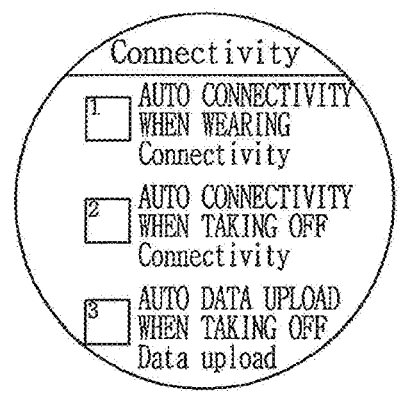
FIG. 42 is a screen view illustrating a method of setting connectivity according to a wearing state.

FIG. 42 is a screen view illustrating a method of setting connectivity according to a wearing state.

When a selection command for connectivity is inputted from a user (see FIG. 28), as shown in a FIG. 42, a setting screen of auto connectivity according to a wearing state may be displayed.

The setting screen may include a setting button for auto connectivity when wearing, a setting button for auto connectivity when taking off, and a setting button for auto data upload when taking off. When theses buttons are selected, auto conductivity when wearing and auto connectivity when taking off may be set. Herein, the taking off refers to taking off the watch type device 100 from a wrist.

Figure 43:
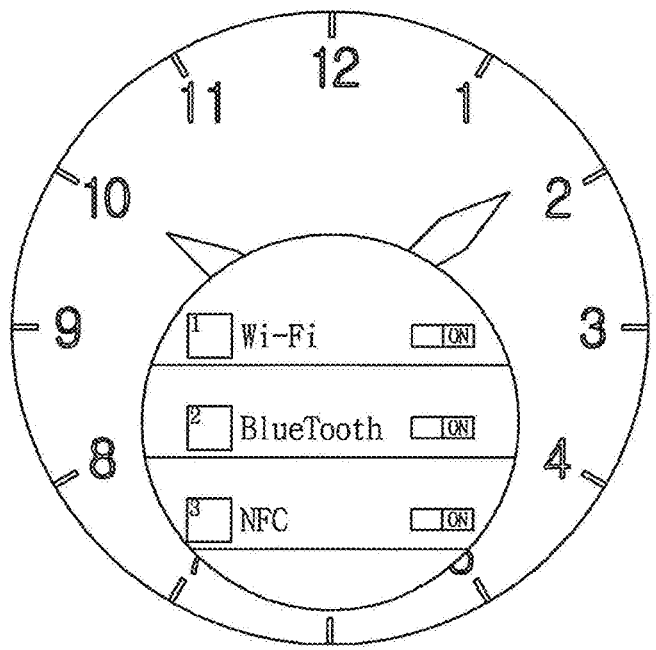
FIG. 43 is a screen view illustrating a screen displaying method when a watch type device is taken off.

FIG. 43 is a screen view illustrating a screen displaying method when a watch type device is taken off.

As shown in FIG. 43, when auto connectivity is set when taking off, as soon as the watch type device 100 is taken off from a user's wrist, without an additional gesture, the type of the currently activated connectivity may be displayed on the display unit 151. The type of connectivity may include Wi-Fi, Bluetooth, and NFC. According to a selection command from a user, Wi-Fi, Bluetooth, and NFC in currently activation may be set to deactivation.

After taking off a watch type device, as Wi-Fi is activated continuously, the present invention may prevent current consumption continuously.

Although not shown in the drawing, when auto connectivity is set when wearing, as soon as the watch type device 100 is taken off from a user's wrist, without an additional gesture, the connectivity types may be displayed on the display unit 151. When a selection command for at least one of the connectivity types is inputted, the selected at least one connectivity type may be activated. For example, a selection command for Bluetooth is inputted from a user, Bluetooth is activated in order to execute a Bluetooth function.

Auto update setting when taking off refers to a setting for performing series of processes to update data or information of the watch type device 100 to another terminal when the watch type device 100 is taken off from a user's wrist.

The other terminal may include a wireless communication system, another watch type device 100, a user's mobile terminal, another user's mobile terminal, an external server, a desktop computer, a notebook computer, and a television.

Figure 44:
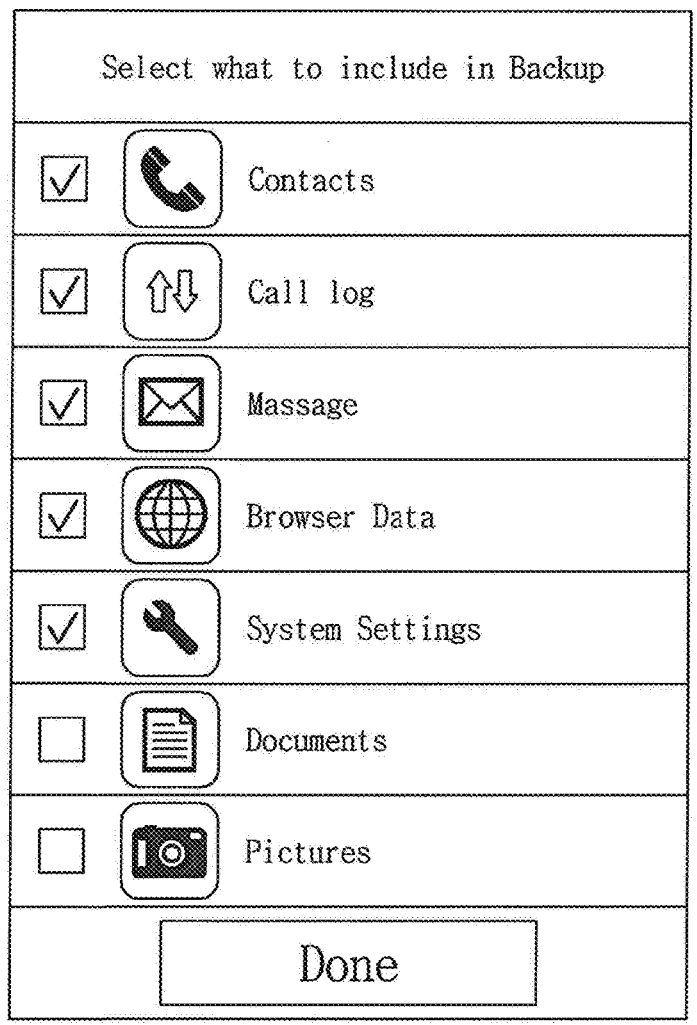
FIG. 44 is another screen view illustrating a screen displaying method when a watch type device is taken off.

In the case of auto data upload when taking off, when the watch type device 100 is taken off from a user's wrist, as shown in FIG. 44, data items to be uploaded to another terminal may be displayed as a pop-up window. As soon as data items are displayed as a pop-up window, data of corresponding data items may be uploaded into a predetermined another terminal.

FIG. 45 is a view illustrating a method of updating an update item manually.

Figure 45A:
FIGS. 45(a), 45(b), 45(c) and 45(d) are views illustrating a method of updating an update item manually.

When a selection command for connectivity is inputted, as shown in FIG. 45A, a setting button for manual update after pop-up alarm when taking off and a setting button for auto update when taking off.

Figure 45B:
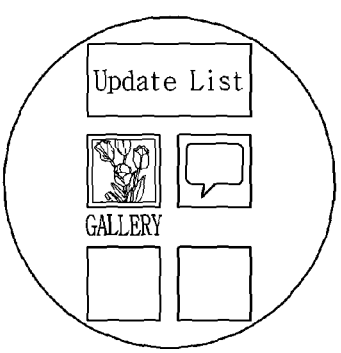

In the case of manual update after pop-up alarm when taking off, when the watch type device 100 is taken off from a user's wrist, as shown in FIG. 45B, update items may be displayed.

Figure 45C:
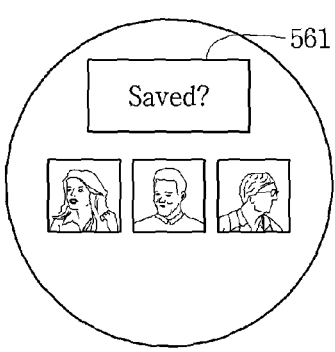
Figure 45D:
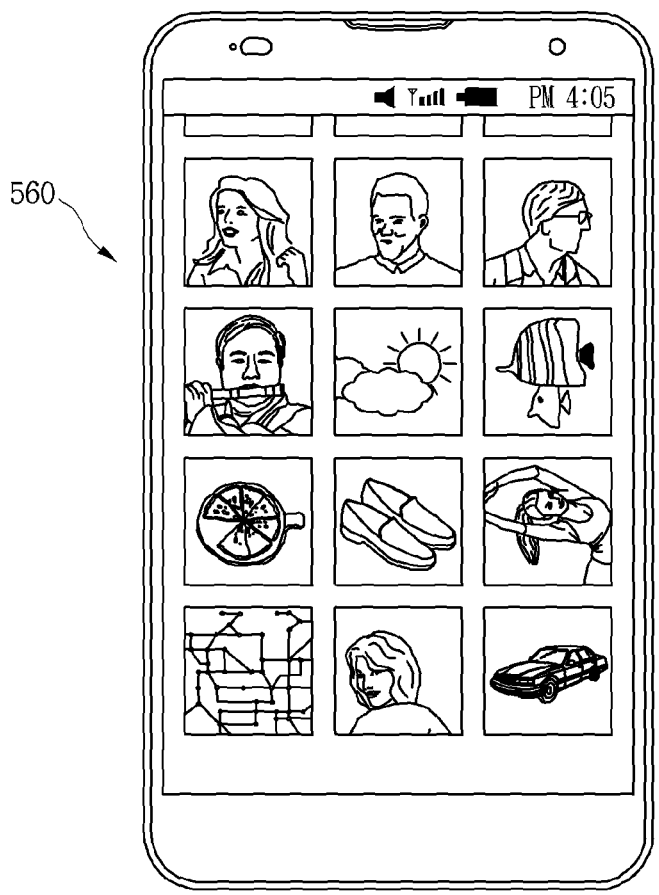

When a selection command for a specific update item is inputted from a user, detailed data of a corresponding update may be displayed. For example, when a selection command for a gallery item is inputted, as shown in FIG. 45C, picture images may be displayed.

In order to update picture images, when a selection command for a save button 561 is inputted, for example, the picture images may be updated in a gallery folder of the mobile terminal 560.

On the other hand, when taking off, update may be performed automatically. In the case of a setting for auto update when taking off, when watch type device 100 is taken off from a user's wrist, update items, for example, may be updated to the mobile terminal 560.

The invention can also be embodied as computer readable codes on a computer readable recording medium. The computer readable recording medium is any data storage device that can store data which can be thereafter read by a computer system. Examples of the computer readable recording medium include magnetic storage media (e.g., ROM, floppy disks, hard disks, etc.) and optical recording media (e.g., CD-ROMs, or DVDs) and carrier waves (e.g., transmission through the Internet). Additionally, the computer may include the control unit 180 of the watch type terminal 100. Accordingly, the detailed description is not construed as being limited in all aspects and should be considered as illustrative. The scope of the invention should be determined by reasonable interpretation of the appended claims, and all modifications within equivalent ranges of the present invention are included in the scope of the present invention.

Effects of a wearable device according to the present invention are described as follows.

According to at least one of embodiments of the present invention, since detailed content of simple notification information can be checked by gripping a watch type device without wearing it, user's convenience may be improved.

According to at least one of embodiments of the present invention, since various states of a watch type device, especially, a hand gripping state, are detected by using an acceleration sensor and a heartbeat sensor and a function according thereto is executed, user's convenience may be improved.

According to at least one of embodiments of the present invention, since a heartbeat sensor does not operate before an acceleration sensor detects wearing, it is prevented that a heartbeat sensor operates unnecessarily to disturb users or other people and power is wasted.

Additionally, according to at least one of embodiments of the present invention, since crosstalk phenomenon is completely removed by a heartbeat sensor including a layer with a partition disposed between a light emitting unit and a light receiving unit, heartbeat measurement errors due to a crosstalk phenomenon may be prevented, so that the measurement performance of a heartbeat sensor is enhanced and the reliability is improved.

Additionally, according to at least one of embodiments of the present invention, after taking off a watch type device, as Wi-Fi is activated continuously, continuous current consumption may be prevented.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A wearable device comprising:
a touch screen configured to display information;
an acceleration sensor configured to generate an acceleration signal;
an optical sensor comprising a light source and configured to generate a touch interrupt signal; and
a control unit configured to:
determine a wearing state of the wearable device based on the acceleration signal or the touch interrupt signal, the wearing state comprising a not-wearing state, a wrist-wearing state, or a hand-gripping state; and
execute a function corresponding to the determined wearing state;
display a first screen representing that the touch screen is turned off if the wearable device is in the not-wearing state,
display a second screen representing a watch screen if the wearable device is in the wrist wearing state, and
display a third screen including notification information if the wearable device is in the hand gripping state,
wherein each of the first screen, the second screen and the third screen is a lock screen or a lock release screen,
the lock screen is a screen for limiting an access of an application in the wearable device, and
the lock release screen is a screen for allowing the access of the application in the wearable device.

2. The wearable device of claim 1, wherein the control unit is further configured to cause the touch screen to change the black screen or the ambient screen to a standby screen when a tilting movement of the wearable device is detected.

3. The wearable device of claim 1, wherein:
the acceleration signal comprises an Absolute Motion Detection (AMD) signal and a Relative Motion Detection (RMD) signal corresponding to different types of movements; and
the control unit is further configured to determine the wearing state based on the AMD signal and the RMD signal.

4. The wearable device of claim 3, wherein the control unit is further configured to determine the wrist-wearing state and the hand-gripping state based on the touch interrupt signal.

5. The wearable device of claim 3, wherein the optical sensor is further configured to generate the touch interrupt signal when the wearing state is determined based on the AMD signal and the RMD signal.

6. The wearable device of claim 1, wherein the control unit is further configured to cause the touch screen to:
display detailed content of the missed message in response to a knock code command input while the standby screen is displayed.

7. The wearable device of claim 1, wherein:
the optical sensor is further configured to generate a heartbeat signal; and
the function corresponding to the wrist-wearing state comprises:
causing the touch screen to display a standby screen;
causing the touch screen to change the standby screen to an ambient screen when a predetermined time elapses after a lock is released;
causing the touch screen to change the ambient screen to a standby screen comprising information provided by a content provider when a tilting movement of the wearable device is detected;
performing user authentication using the heartbeat signal; and
causing the touch screen to display detailed content related to the information provided by the content provider when the user authentication is successful.

8. The wearable device of claim 1, wherein the function corresponding to the wrist-wearing state comprises causing the touch screen to:
display a black screen; and
change the black screen to either an ambient screen in a lock-released state or a standby screen based on a previous occurrence of a one-time lock-release event,
wherein the black screen is changed in response to a double tap input.

9. The wearable device of claim 1, wherein:
the optical sensor is further configured to generate a heartbeat signal; and
the function corresponding to the wrist-wearing state comprises:
causing the touch screen to display a black screen;
performing user authentication using the heartbeat signal; and
causing the touch screen to change the black screen to either an ambient screen in a lock-released state or a standby screen based on whether the user authentication is successful and a previous occurrence of a lock-release event.

10. The wearable device of claim 1, wherein the function corresponding to the non-wearing state comprises causing the touch screen to:
display a black screen; and
change the black screen to a standby screen in response to a knock code or a lock pattern input.

11. The wearable device of claim 1, wherein the function corresponding to the wrist-wearing state comprises:
 causing the touch screen to display a black screen; and
 executing a predetermined application in response to a drag touch along a specific portion of the black screen.

12. The wearable device of claim 1, wherein the control unit is further configured to:
 cause the touch screen to display at least one connectivity type when the wearing state is changed from the wrist-wearing state to the not-wearing state; and
 deactivate a selected one of the at least one connectivity type in response to a selection input to the displayed selected one connectivity type.

13. The wearable device of claim 12, wherein the displayed at least one connectivity type comprises at least Wi-Fi, Bluetooth, or NFC.

14. The wearable device of claim 1, wherein the function corresponding to the wrist-wearing state comprises causing the touch screen to:
 display a standby screen in a lock-released state in response to a lock release operation;
 change the standby screen to an ambient screen in a lock-released state when a predetermined time elapses; and
 change the ambient screen back to the standby screen in the lock-released state in response to a double tap input to the displayed ambient screen;
 wherein the ambient screen is displayed with a lower brightness than the standby screen.

15. The wearable device of claim 1, wherein the optical sensor comprises a heartbeat sensor.

16. A control method of a wearable device, the method comprising:
 determining a wearing state of the wearable device based on an acceleration signal or a touch interrupt signal, the wearing state comprising a not-wearing state, a wrist-wearing state, or a hand-gripping state; and
 executing a function corresponding to the determined wearing state,
 wherein the executing the function comprises
 displaying a first screen representing that the touch screen is turned off if the wearable device is in the not-wearing state,
 displaying a second screen representing a watch screen if the wearable device is in the wrist wearing state, and
 displaying a third screen including notification information if the wearable device is in the hand gripping state,
 wherein each of the first screen, the second screen and the third screen is a lock screen or a lock release screen,
 the lock screen is a screen for limiting an access of an application in the wearable device, and
 the lock release screen is a screen for allowing the access of the application in the wearable device.

17. The method of claim 16, wherein the function corresponding to the wrist-wearing state comprises:
 displaying a standby screen;
 receiving a heartbeat signal;
 changing the standby screen to an ambient screen when a predetermined time elapses after a lock is released;
 changing the ambient screen to a standby screen comprising information provided by a content provider when a tilting movement of the wearable device is detected;
 performing user authentication using the heartbeat signal; and
 displaying detailed content related to the information provided by the content provider when the user authentication is successful.

18. The method of claim 16, wherein the function corresponding to the wrist-wearing state comprises:
 displaying the black screen;
 receiving a heartbeat signal;
 performing user authentication using the heartbeat signal; and
 changing the black screen to either a lock-released ambient screen or a standby screen based on whether the user authentication is successful and a previous occurrence of a lock-release event.

19. The method of claim 16, wherein the function corresponding to the wrist-wearing state comprises:
 displaying a standby screen in a lock-released state in response to a lock release operation;
 changing the standby screen to the ambient screen in a lock-released state when a predetermined time elapses; and
 changing the ambient screen back to the standby screen in the lock-released state in response to a double tap input to the displayed ambient screen;
 wherein the ambient screen is displayed with a lower brightness than the standby screen.

* * * * *